(12) United States Patent
Surolia et al.

(10) Patent No.: US 8,940,691 B2
(45) Date of Patent: Jan. 27, 2015

(54) METHOD FOR TREATING METABOLIC DISORDERS INCLUDING TYPE 1 AND TYPE 2 DIABETES MELLITUS

(71) Applicants: Avadhesha Surolia, New Delhi (IN); Sarika Gupta, New Delhi (IN); Mahendra Pal Singh, New Delhi (IN); Tandrika Chattopadhyay, New Delhi (IN)

(72) Inventors: Avadhesha Surolia, New Delhi (IN); Sarika Gupta, New Delhi (IN); Mahendra Pal Singh, New Delhi (IN); Tandrika Chattopadhyay, New Delhi (IN)

( * ) Notice: Subject to any disclaimer, the term of this patent is extended or adjusted under 35 U.S.C. 154(b) by 0 days.

(21) Appl. No.: 13/845,209

(22) Filed: Mar. 18, 2013

(65) Prior Publication Data

US 2013/0217621 A1   Aug. 22, 2013

Related U.S. Application Data

(62) Division of application No. 12/419,669, filed on Apr. 7, 2009, now Pat. No. 8,426,362.

(30) Foreign Application Priority Data

Apr. 7, 2008 (IN) .............................. 914/DEL/2008

(51) Int. Cl.
*A61K 38/28* (2006.01)
*A61P 3/10* (2006.01)
*A61K 9/00* (2006.01)
*A61K 38/23* (2006.01)

(52) U.S. Cl.
CPC ............... *A61K 9/0002* (2013.01); *A61K 38/28* (2013.01); *A61K 38/23* (2013.01)
USPC ............................... 514/5.9; 514/6.8; 514/6.9

(58) Field of Classification Search
USPC ......................................................... 514/5.9
See application file for complete search history.

(56) References Cited

U.S. PATENT DOCUMENTS 6,506,724 B1   1/2003   Hiles et al. ................. 514/2

OTHER PUBLICATIONS

Bevan, P., "Insulin signalling", *J. Cell Science.*, 114(8):1429-1430 (2001).
Bjorntorp et al., "Differentiation and function of rat adipocyte precursor cells in primary culture", *J. Lipid Res.*, 21:714-723 (1980).
Duckworth et al., "Insulin Degradation: Progress and Potential", *Endocrine Rev.*, 19(5):608-624 (1998).
Dunstan et al., "The Rising Prevalence of Diabetes and Impaired Glucose Tolerance", *Diabetes Care*, 25(5):829-834 (2002).
King et al., "Global Burden of Diabetes, 1995-2025, Prevalence, numerical estimates, and projections", *Diabetes Care*, 21(9):1414-1431 (1998).
Klunk et al., "Quantifying Amyloid by Congo Red Spectral Shift Assay", *Meth. Enzymol.*, 309:285-305 (1999).
LeVine, H., "Quantification of β-Sheet Amyloid Fibril Structures with Thioflavin T", *Meth. Enzymol.*, 309:274-284 (1999).
Nathan et al., "Intensive Diabetes Treatment and Cardiovascular Disease in Patients with Type 1 Diabetes", *N.E. J. Med.*, 353(25):2643-2653 (2005).
Nicol et al., "Amino-Acid Sequence of Human Insulin", *Nature*, 187:483-485 (1960).
Paulsen et al., Insulin resistance caused by massive degradation of subcutaneous insulin, *Diabetes*, 28:640-645 (1979).
Sanz et al., "IL-4-Induced Eosinophil Accumulation in Rat Skin Is Dependent on Endogenous TNF-α and $α_4$ Integrin/VCAM-1 Adhesion Pathways", *J. Immunol.*, 160:5637-5645 (1998).
Schagger et al., "Tricine-Sodium Dodecyl Sulfate-Polyacrylamide Gel Electrophoresis for the Separation of Proteins in the Range from 1 to 100 kDa", *Anal. Biochem.*, 166:368-379 (1987).

*Primary Examiner* — Gyan Chandra
(74) *Attorney, Agent, or Firm* — Klauber & Jackson LLC

(57) ABSTRACT

A supramolecular insulin assembly and supramolecular exendin-4 assembly, which is useful as a protein therapeutic agent for the treatment of metabolic disorders particularly diabetes. The supramolecular assemblies disclosed in the present invention consists of insoluble and aggregated oligomers the protein. The invention also provides pharmaceutical compositions comprising the supramolecular assembly.

12 Claims, 34 Drawing Sheets

TEM micrographs

Induction of Cataract (a) STZ-Treated Rat  (b) Control Rat  (c) Insulin –Treated Rats
(single daily dose)

(d) Insulin –Treated Rats  (e) SIA-
(Twice daily dose)  Treated Rats

METHOD FOR TREATING METABOLIC DISORDERS INCLUDING TYPE 1 AND TYPE 2 DIABETES MELLITUS

CROSS REFERENCE TO RELATED APPLICATIONS

The present application is a Divisional Application of U.S. application Ser. No. 12/419,669, filed on Apr. 7, 2009, which is now U.S. Pat. No. 8,426,362, which in turn, claims priority from Indian Patent Application Serial No. 914/DEL/2008, filed on Apr. 7, 2008. Applicants claim the benefits of 35 U.S.C. §120 as to the said Applications, and the entire disclosures of both applications are incorporated herein by reference in their entireties.

TECHNICAL FIELD

The present invention relates to protein therapeutics for treatment of diabetes and other chronic diseases.

BACKGROUND OF INVENTION

Protein medications are the most rapidly expanding class of therapeutics, serving patients with diabetes, cancer, cardiovascular, renal, gastrointestinal, rheumatologic and neurological diseases, among many others. The therapeutic and commercial value of proteins as therapeutics including insulin, erythropoietin, G-CSF, plasminogen activator, and interferons is undisputed. Improved proteins or their formulations have enhanced the therapeutic efficacy of these parent products, by increasing their potency, time of action, and other properties.

Diabetes is a chronic disease characterized by either the inability of the body to produce insulin (Type I) or the failure to respond to it (Type II) (http://www.who.int/diabetes/en, King, H., Aubert, R. E. & Herman, W. H. Global burden of diabetes, 1995-2025: Prevalence, numerical estimates, and projections. *Diabetes Care* 21, 1414-1431 (1998)). There is an emerging global epidemic of diabetes of both Type I and Type II forms. Nearly 1.1 million diabetics succumbed to death in 2005 (Dunstan, D. W., Zimmet, P. Z., Welborn, T. A., De Courten, M. P., Cameron, A. J., et al. The rising prevalence of diabetes and impaired glucose tolerance: The Australian Diabetes, Obesity and Lifestyle Study. *Diabetes Care* 25, 829-834 (2002)). Its economic consequences are even more staggering as people may live for years with diabetes, their cause of death is often recorded as heart diseases and kidney failures, both arising as a secondary consequence of diabetes. Restoring the normal metabolic milieu by administration of insulin from outside and thereby minimizing the risk of secondary complications has become an essential feature of diabetic treatment. The current therapy involves multiple daily subcutaneous (SC)/intramuscular (IM) injections of insulin, which leads to a heavy burden of compliance on patients. This in turn has led to alternative, less invasive routes of delivery. Attempts to exploit the nasal, oral, gastrointestinal and transdermal routes, have been mostly unsuccessful. Although a conventional insulin regimen for type I diabetes with twice-daily insulin injections is effective in controlling postprandial blood glucose levels, this treatment is of limited value due to its failure to control fasting hyperglycemia. Patients with diabetes mellitus need insulin therapy to boost intrinsic insulin supply once or twice a day. Also, post-prandial glucose homeostasis is maintained through regular insulin injections before each meal. Intensive insulin therapy delays the onset and or slows the progression of secondary complications, yet patients remain at a high risk of fasting hypoglycemia. An insulin formulation which releases insulin in a controlled manner for long periods of time would free the patients from the need to administer multiple doses of insulin daily.

SUMMARY OF THE INVENTION

The invention provides a composition for a prolonged release of insulin and/or exendin-4 for treating diabetes, both type I and II, e.g., protein therapeutics for treatment of diabetes and other chronic diseases. Disclosed herein is a supramolecular insulin assembly, wherein the supramolecular insulin assembly comprises the insoluble and aggregated oligomeric form of insulin and/or exendin-4. The present invention also discloses the supramolecular exendin-4 assembly (SEA).

One aspect of the present invention relates to a supramolecular insulin assembly (SIA), which is useful as a protein therapeutic for the treatment of metabolic disorders selected from the group consisting of type 1, type 2 diabetes mellitus and complications. The assembly comprises insoluble and aggregated oligomeric form of insulin.

Another aspect of the present invention relates to a supramolecular insulin assembly (SIA) useful as protein therapeutics for the treatment of metabolic disorders selected from the group consisting of type 1, type 2 diabetes mellitus and complications thereof, wherein the assembly comprises of insoluble and aggregated oligomeric form of insulin as SIA I, SIA II, SIA III or combination thereof. For example SIA I consists of elongated clusters having pearl like arrangement of insulin monomer, SIA II consists of linear association of elongated clusters having pearl like arrangement of insulin monomer, or SIA III consists of about 90% SIA-II, that is a dense, linear association of insulin oligomers.

Another aspect of the present invention relates to a supramolecular insulin assembly (SIA) useful as a protein therapeutic for the treatment of metabolic disorders selected from the group consisting of type 1, type 2 diabetes mellitus and complications thereof, wherein the assembly comprises insoluble and aggregated oligomeric form of insulin as SIA I, wherein SIA I consists of elongated clusters having pearl like arrangement of insulin monomer.

Yet another aspect of the present invention relates to a supramolecular insulin assembly (SIA) useful as a protein therapeutic for the treatment of metabolic disorders selected from the group consisting of type 1, type 2 diabetes mellitus and complications thereof, wherein the assembly comprises insoluble and aggregated oligomeric form of insulin as SIA II, wherein SIA II consists of linear association of elongated clusters having pearl like arrangement of insulin monomer.

Still another aspect of the present invention relates to a supramolecular insulin assembly (SIA) useful as a protein therapeutic for the treatment of metabolic disorders selected from the group consisting of type 1, type 2 diabetes mellitus and complications thereof, wherein the assembly comprises insoluble and aggregated oligomeric form of insulin as SIA III, wherein SIA III consists dense, linear association of insulin oligomers.

Further aspect of the present invention relates to a supramolecular exendin-4 assembly (SEA) useful as a protein therapeutic for the treatment of diabetes, wherein said assembly comprises insoluble and aggregated oligomeric form of exendin-4.

Another aspect of the present invention relates to a pharmaceutical composition for the treatment of metabolic disorders selected from the group consisting of type 1, type 2 diabetes mellitus and complications thereof, the composition comprising therapeutically effective amount of the supramolecular insulin assembly (SIA) as disclosed in the present invention.

Yet another aspect of the present invention relates to a pharmaceutical composition for the treatment of metabolic disorders selected from the group consisting of type 1, type 2 diabetes mellitus and complications thereof. The composition comprises therapeutically effective amount of the supramolecular insulin assembly-II (SIA-II).

Still another aspect of the present invention relates to a pharmaceutical composition for the treatment of metabolic disorders selected from the group consisting of type 1, type 2 diabetes mellitus and complications thereof. The composition comprises a therapeutically effective amount of the supramolecular insulin assembly (SIA) and supramolecular exendin-4 assembly (SEA).

Still yet another aspect of the present invention relates to a pharmaceutical composition for the treatment of metabolic disorders selected from the group consisting of type 1, type 2 diabetes mellitus and complications thereof, the composition comprising therapeutically effective amount of the supramolecular insulin assembly (SIA) and supramolecular exendin-4 assembly (SEA).

Yet another aspect of the present invention relates to a pharmaceutical composition for the treatment of metabolic disorders selected from the group consisting of type 1, type 2 diabetes mellitus and complications thereof, the composition comprising therapeutically effective amount of supramolecular exendin-4 assembly (SEA).

Another aspect of the present invention relates to a process of preparation of supramolecular insulin assembly (SIA) as disclosed in the present invention, the process comprising; dissolving insulin at a temperature of about 25 to 60° C. in a solution having pH in the range of about 1.5 to 7.8; and incubating the above for a period of about 6 to 48 hours with constant shaking to obtain Supramolecular Insulin Assembly (SIA), wherein SIA comprises insoluble and aggregated oligomeric form of insulin.

Yet another aspect of the present invention relates to a process of preparation of supramolecular exendin-4 assembly. The process comprises dissolving exendin-4 at a temperature of about 25° C. to 60° C. in a solution having pH in the range of about 2.0 to 7.6; and incubating the above for a period of 6 to 192 hours with constant shaking to obtain Supramolecular Exendin-4 Assembly (SEA), wherein SEA comprises insoluble and aggregated oligomeric form of Exendin-4.

Further aspect of the present invention relates to a method for treating metabolic disorders selected from the group consisting of type 1, type 2 diabetes mellitus and complications thereof, wherein the method comprises administering to a subject in need thereof a therapeutically effective amount of the pharmaceutical composition comprising the supramolecular insulin assembly at a dose which is effective for the alleviation of the disorder.

Yet another aspect of the present invention relates to a method for treating metabolic disorders selected from the group consisting of type 1, type 2 diabetes mellitus and complications thereof, wherein the method comprises administering to a subject in need thereof a therapeutically effective amount of the pharmaceutical composition comprising the supramolecular insulin assembly-II (SIA-II), which is effective for the alleviation of the disorder.

Yet another aspect of the present invention relates to a method for treating metabolic disorders selected from the group consisting of type 1, type 2 diabetes mellitus and complications thereof, wherein the method comprising administering to a subject in need thereof a therapeutically effective amount of the pharmaceutical composition comprising the supramolecular exendin-4 assembly, which is effective for the alleviation of said disorder.

Still yet another aspect of the present invention relates to a method for treating metabolic disorders selected from the group consisting of type 1, type 2 diabetes mellitus and complications thereof, wherein the method comprising administering to a subject in need thereof a therapeutically effective amount of the pharmaceutical composition comprising the supramolecular insulin assembly and supramolecular exendin-4 assembly, which is effective for the alleviation of said disorder.

Another aspect of the present invention relates to use of supramolecular insulin assembly for the treatment of metabolic disorders selected from the group consisting of type 1, type 2 diabetes mellitus and complications thereof.

Still yet another aspect of the present invention relates to use of supramolecular exendin-4 assembly for the treatment of metabolic disorders selected from the group consisting of type 1, type 2 diabetes mellitus and complications thereof.

Still yet another embodiment of the present invention relates to use of supramolecular insulin assembly in combination with supramolecular exendin-4 assembly for the treatment of metabolic disorders selected from the group consisting of type 1, type 2 diabetes mellitus and complications thereof.

Polypeptides or other compounds described herein are purified or isolated. A purified or isolated composition (e.g., protein, polypeptide) is at least 60% by weight (dry weight) the compound of interest. Preferably, the preparation is at least 75%, more preferably at least 90%, and most preferably at least 99%, by weight the compound of interest. Purity is measured by any appropriate standard method, for example, by column chromatography, polyacrylaminde gel electrophoresis, or HPLC analysis. The polypeptide is purified from MSC culture media or recombinantly produced.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

BRIEF DESCRIPTION OF THE DRAWINGS

(a) insulin monomer
(b) supramolecular insulin assembly I (alternatively pre-amyloid insulin I) intermediate, pH 7.0 of Bovine insulin,
(c) supramolecular insulin assembly II (alternatively pre-amyloid insulin II), pH 7.0 of Bovine insulin,
(d) supramolecular insulin assembly intermediate III (alternatively pre-amyloid insulin III), pH 7.0 of Bovine insulin,
(e) supramolecular insulin assembly-I, pH 7.0 of rH-insulin,
(f) supramolecular insulin assembly-II, pH 7.0 of rH-insulin,
(g) supramolecular insulin assembly-III, pH 7.0 of rH-insulin,
(h) fully formed fibrils at pH 7.0, (i) shows supramolecular insulin assembly (alternatively pre-amyloid insulin) intermediate formed at 6 hrs, pH 2.0 at 37° C.,
(j) amyloid fibril formed at pH 2.0.

7a: Blood glucose level in response to various dosages of supramolecular insulin assembly-II (bovine) administered both subcutaneously and intramuscularly.

7b: Blood glucose level in response to various dosages of supramolecular insulin assembly-II (r-human) administered both subcutaneously and intramuscularly.

Figure 8A:
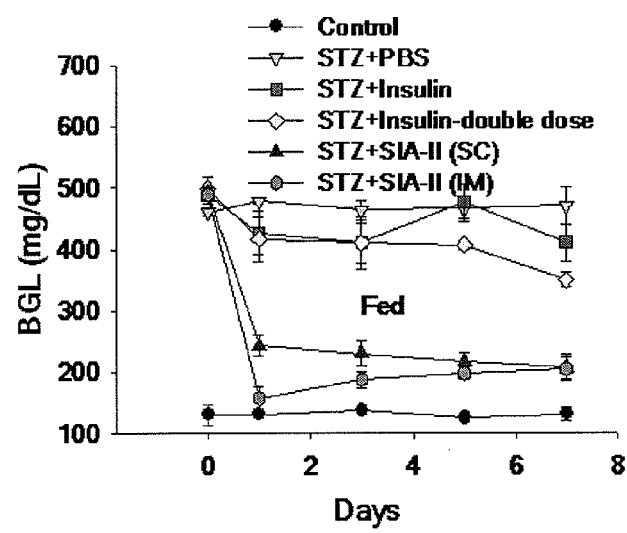
Figure 8A:
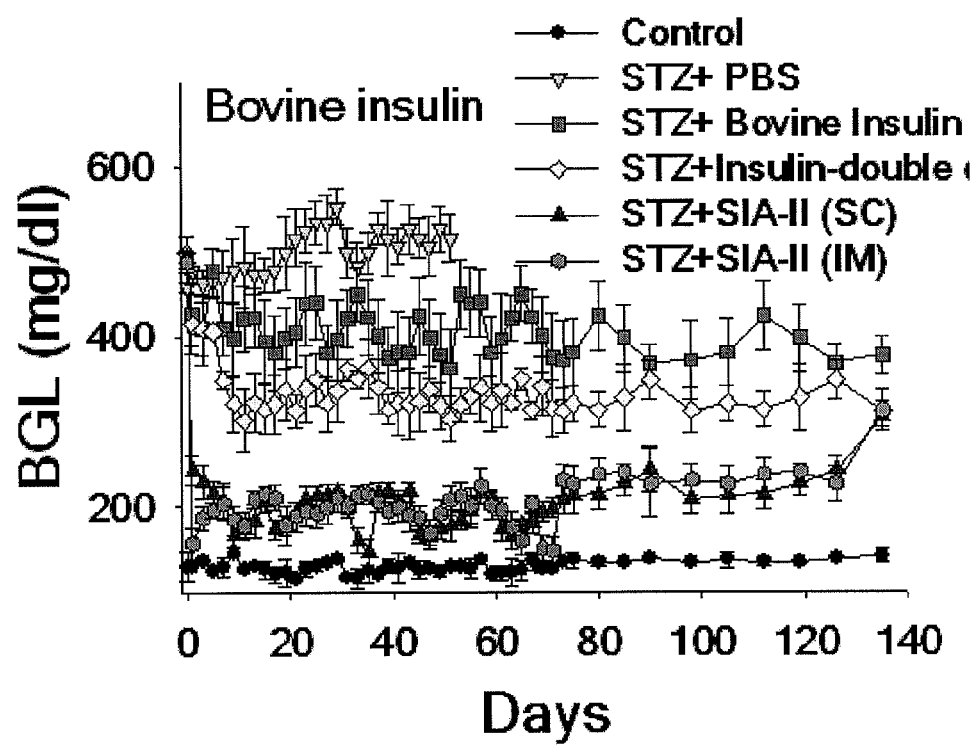
Figure 8B:
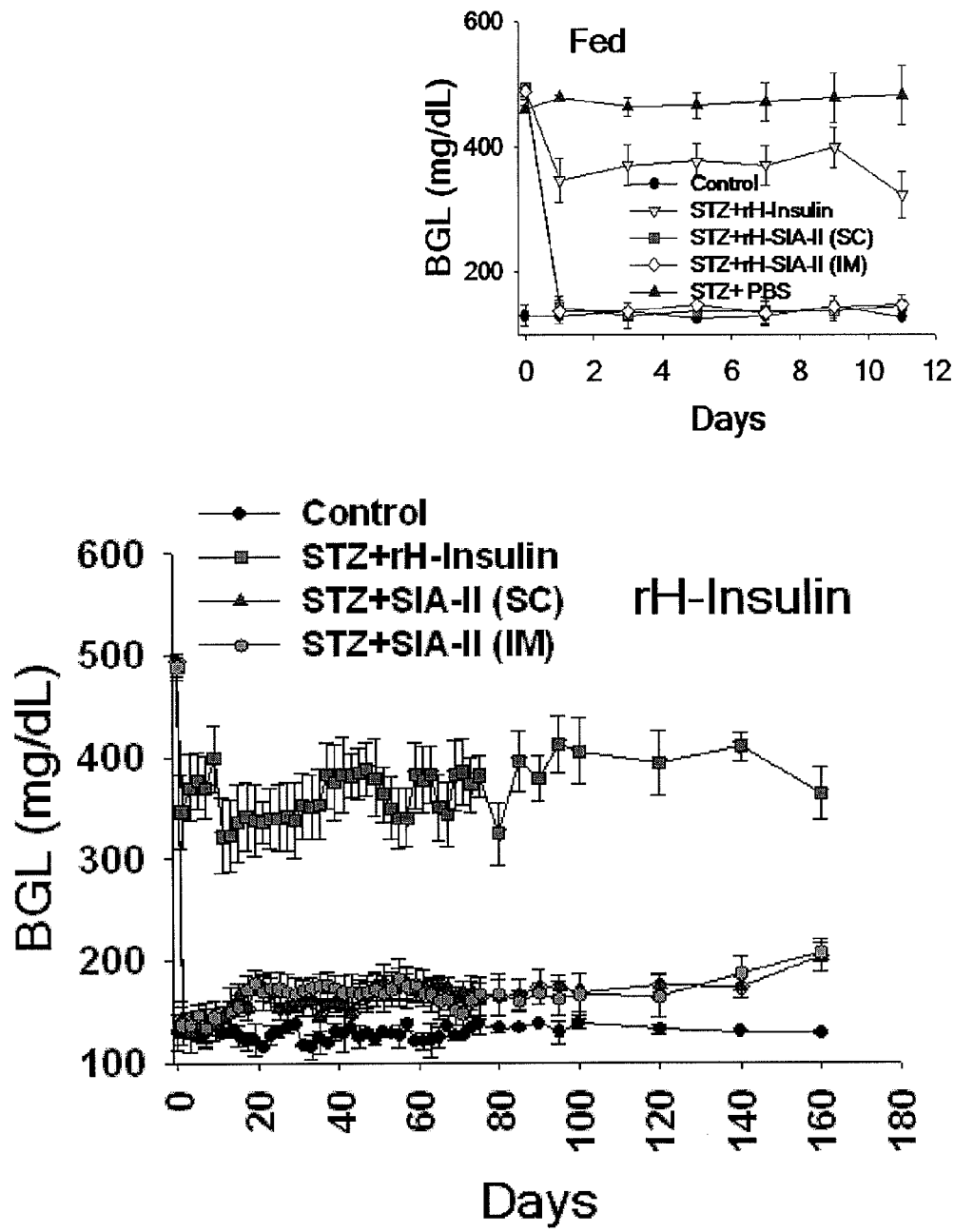

FIGS. 8a-b are line graphs showing post-prandial blood glucose levels monitored over a period of 135 days after administration of bovine SIA-II 8a: Bovine insulin
8b: rH insulin.

Figure 9A:
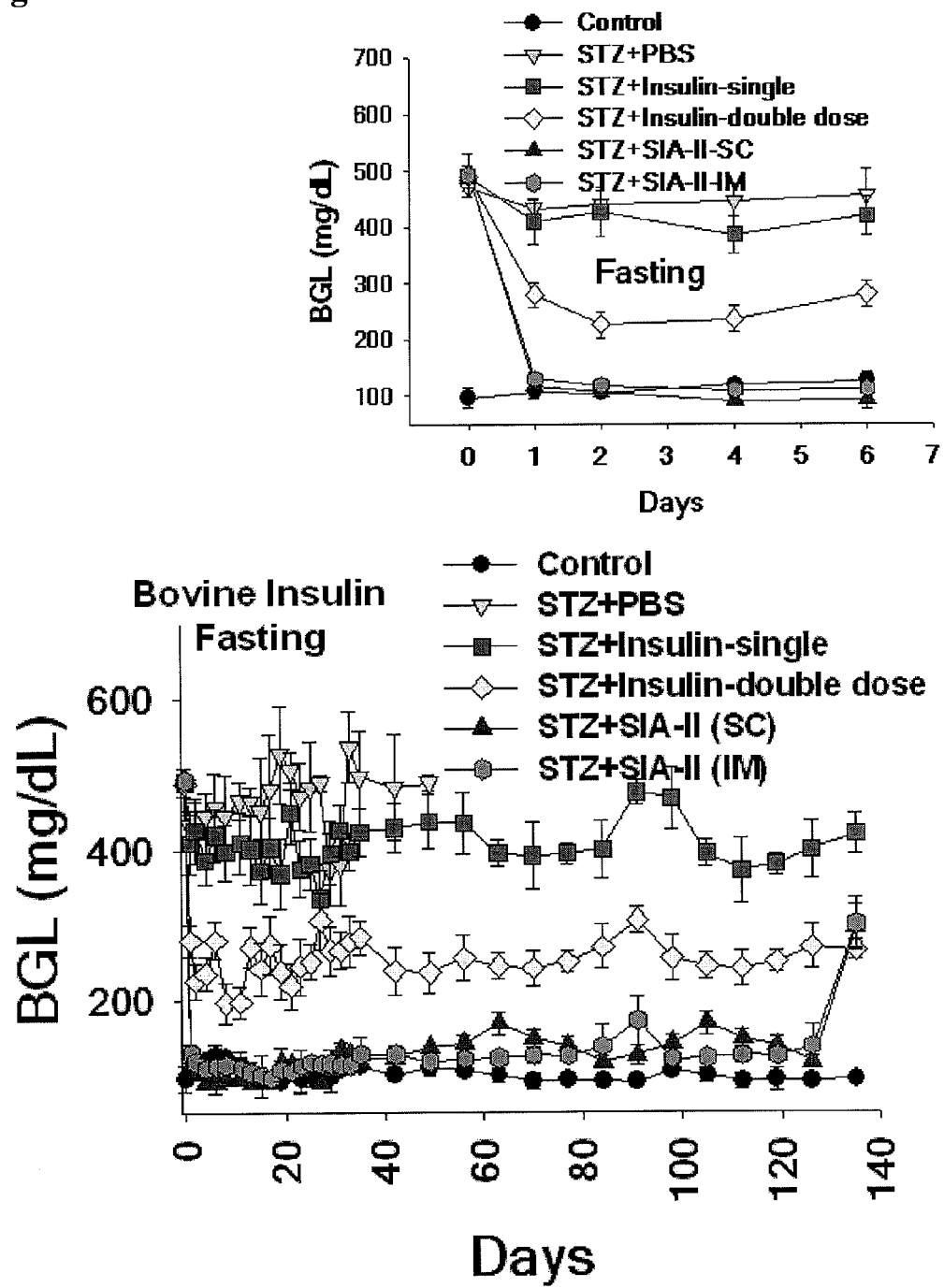
Figure 9B:
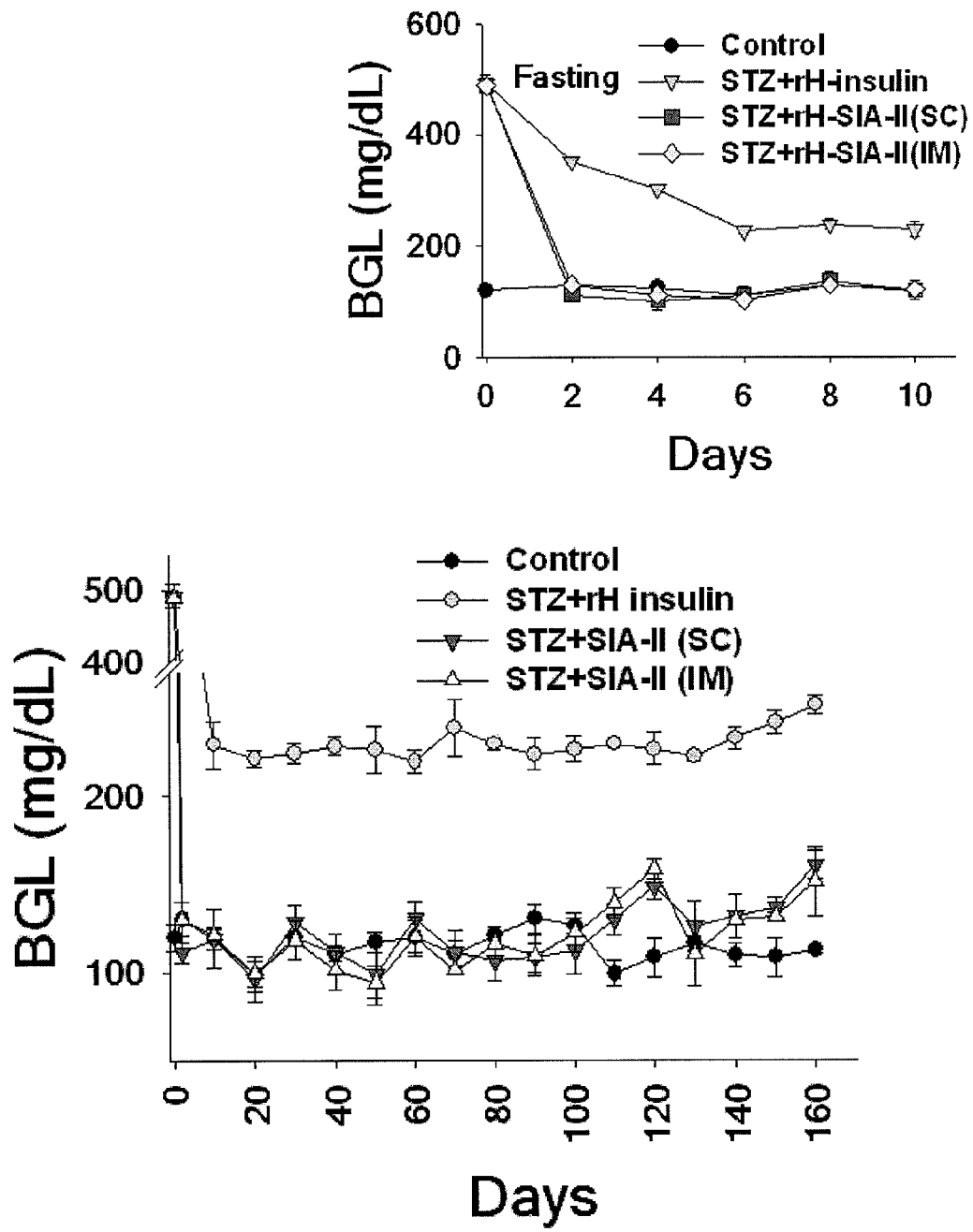

FIGS. 9a-b are line graphs showing pre-prandial blood glucose levels monitored over a period of 160 days after administration of human SIA-II 9a: Bovine insulin
9b: rH insulin.

Figure 10:
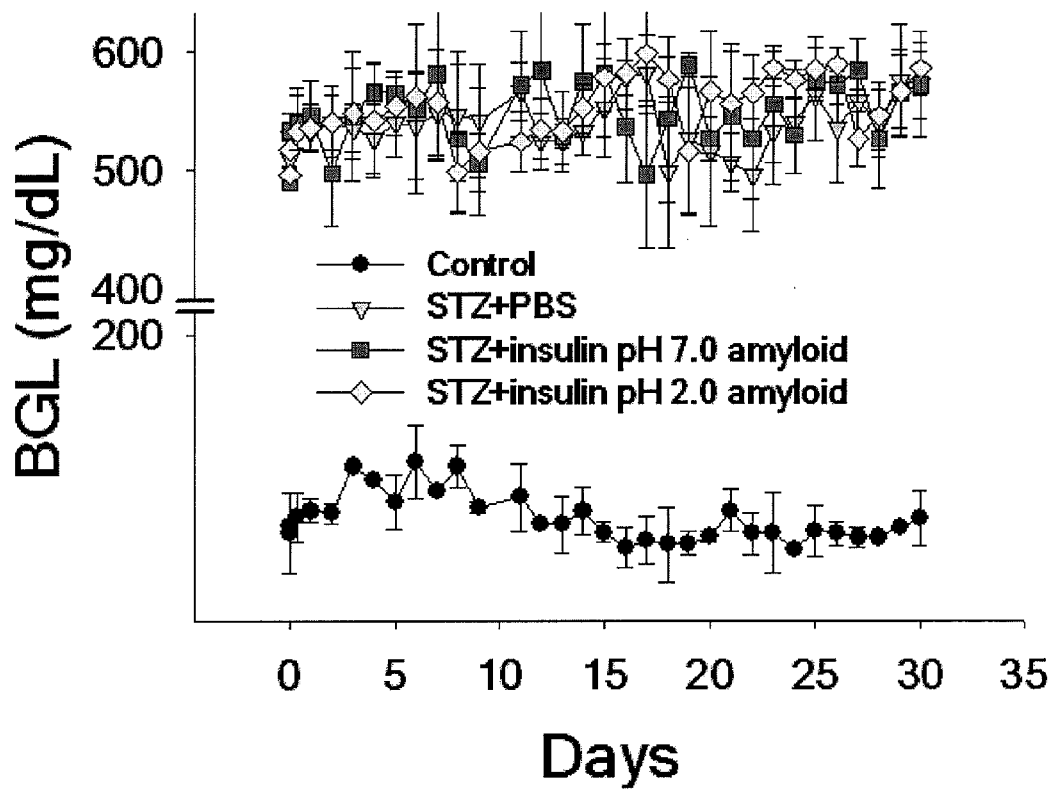

FIG. 10 is a line graph showing blood glucose level monitored after administration of insulin amyloid formed at pH 2.0 and 7.0.

Figure 11:
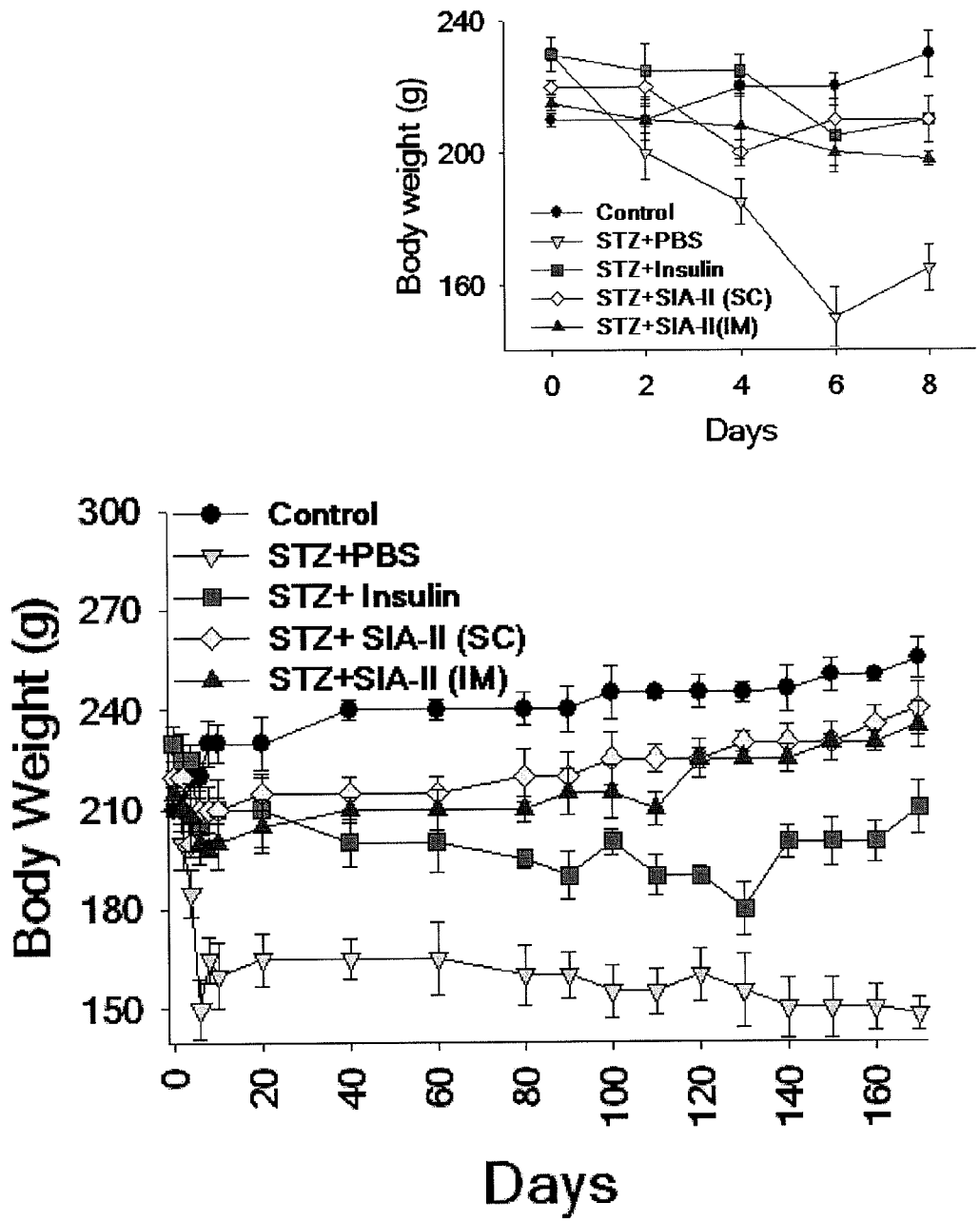

FIG. 11 is a series of line graphs showing body weight profiles of SIA-II treated diabetic rats, diabetic control and non-diabetic control rats.

Figure 12:
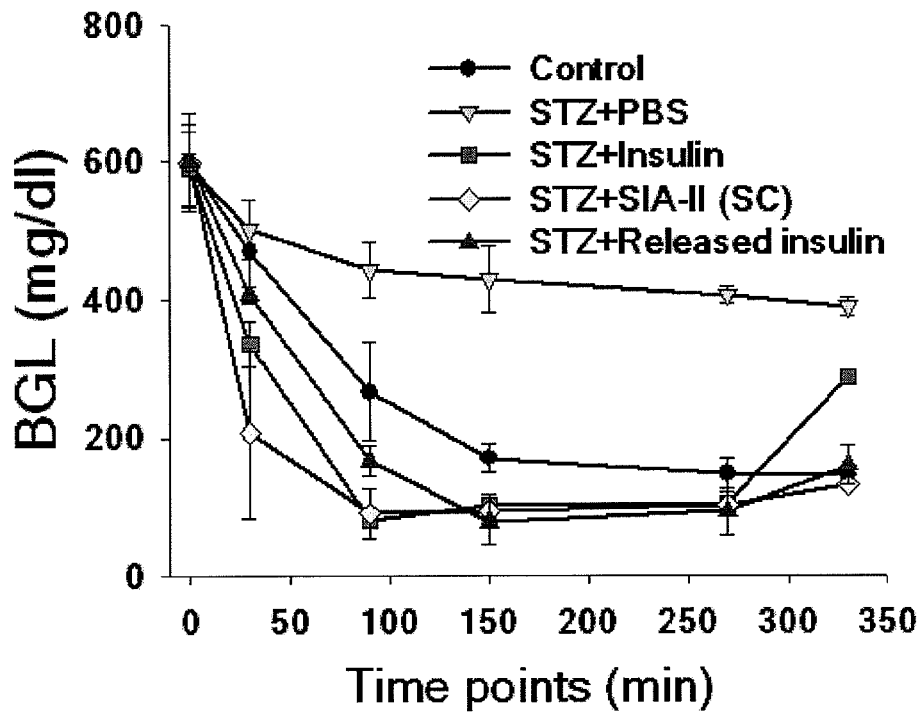

FIG. 12 is a line graph showing blood glucose profiles during intraperitoneal glucose tolerance test (IPGTT)

Figure 13A:
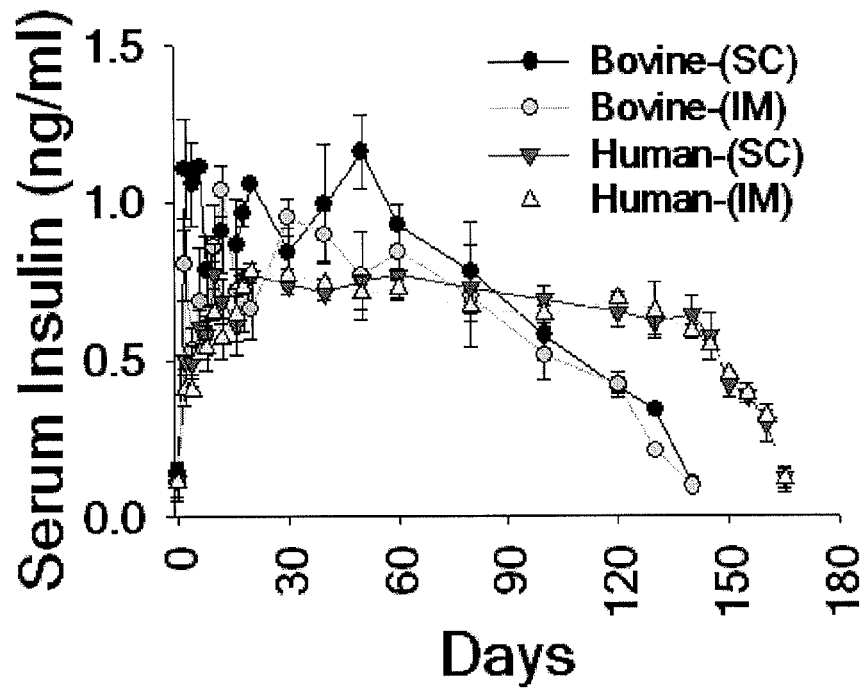

FIG. 13a is a line graph showing quantification of serum rH and bovine insulin released from corresponding SIA-II using solid state ELISA in STZ treated rats in response to supramolecular insulin assembly (alternatively pre-amyloid insulin) injected SC or IM.

Figure 13B:
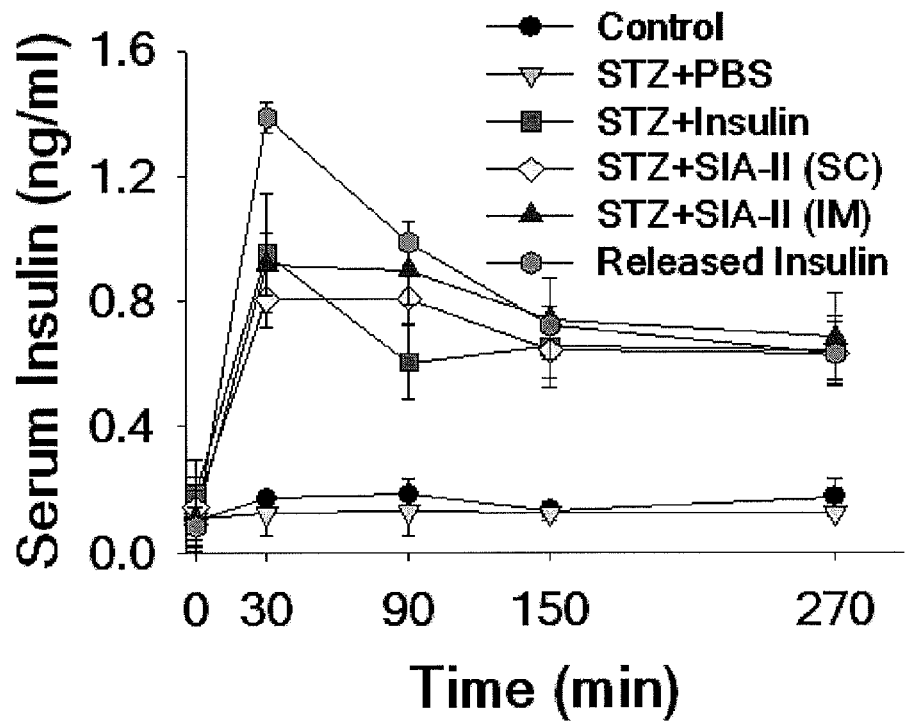

FIG. 13b is a line graph showing quantification of serum bovine insulin during IPGTT experiment.

Figure 13C:
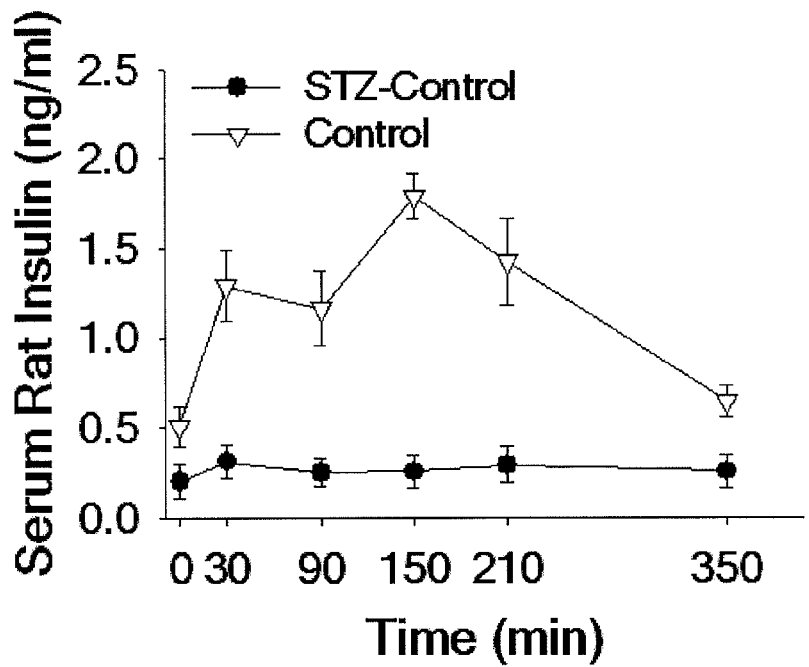

FIG. 13c is a line graph showing serum rat insulin ELISA performed for IPGTT to determine the endogenous level of insulin in response to infused glucose.

Figure 14A:
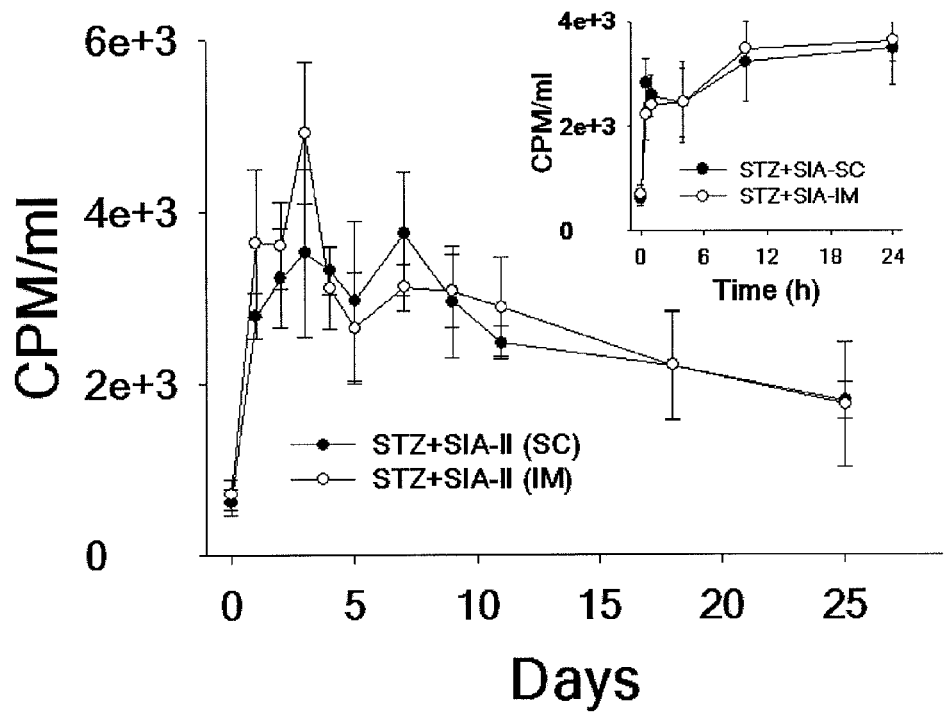
Figure 14B:
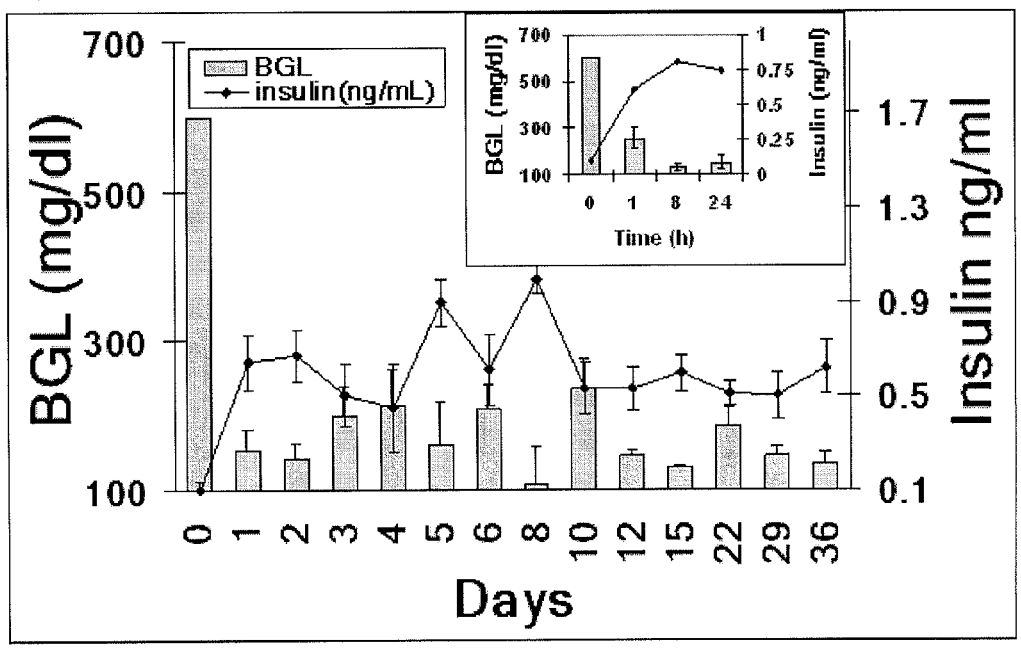
Figure 15:
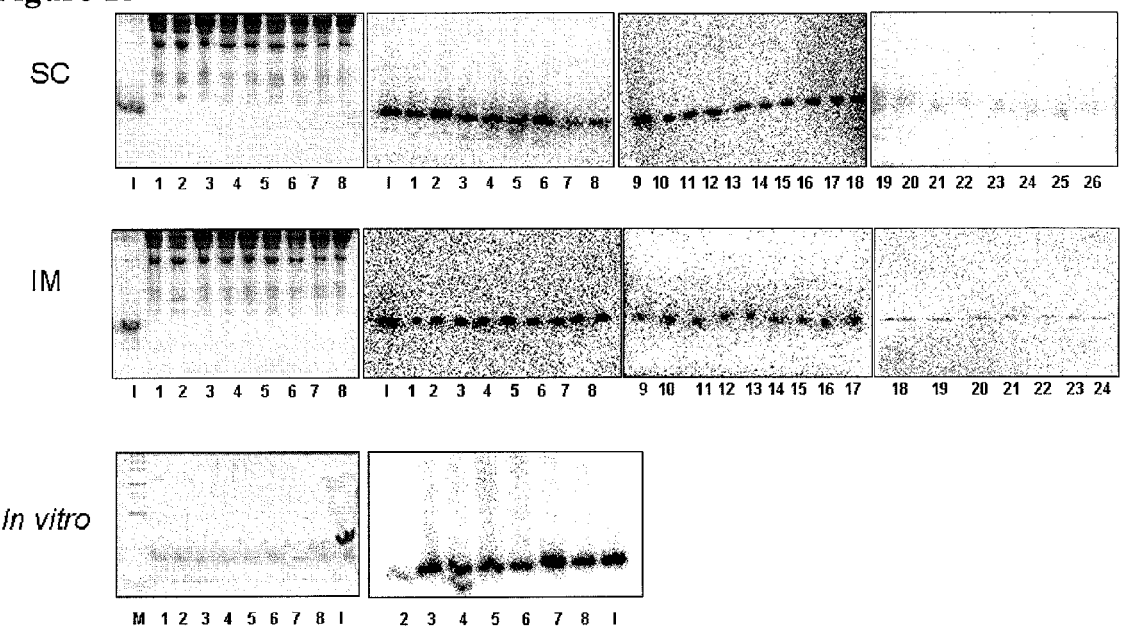

FIGS. 14a-b are line graphs showing $^{125}I$ labeled bovine insulin SIA II treatment of STZ diabetic rats 14a: CPM/ml profile in serum of animals treated with 100 μg of labeled supramolecular insulin assembly up to 25 days. The profile for 24 h is given in inset 14b: Blood glucose (mg/dL) and bovine insulin (ng/ml) released in vivo profile for 36 days. The profile for 24 h is shown in inset FIG. 15 is a series of photographs of electrophoretic gels showing Tricine-SDS-PAGE of serum from animals treated with labeled SIA II. Coommassie staning (left) and phosphor images (rest after left) of serum of 1-28 days after treatment either subcutaneously (upper panel) or intramuscularly (middle panel). The lower panel shows in vitro released monomers from SIA II.

Figure 16A:
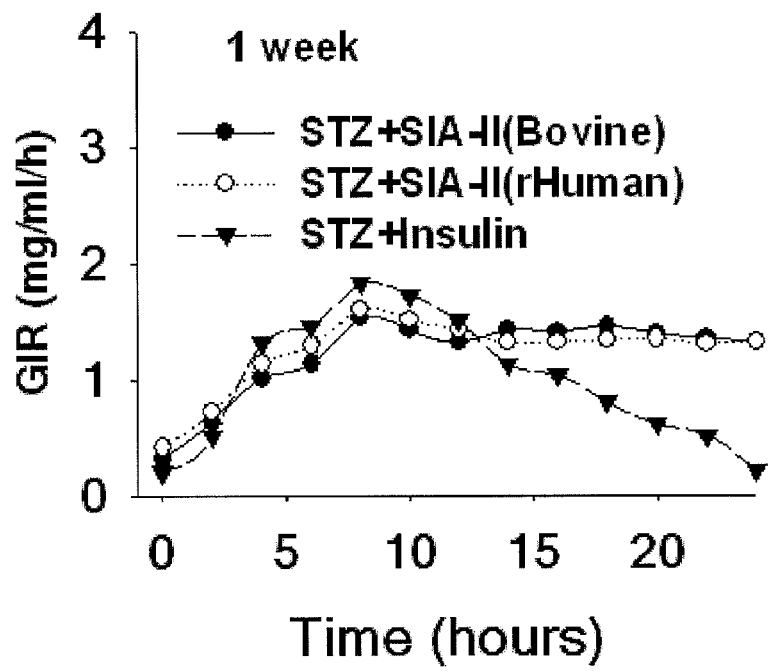
Figure 16B:
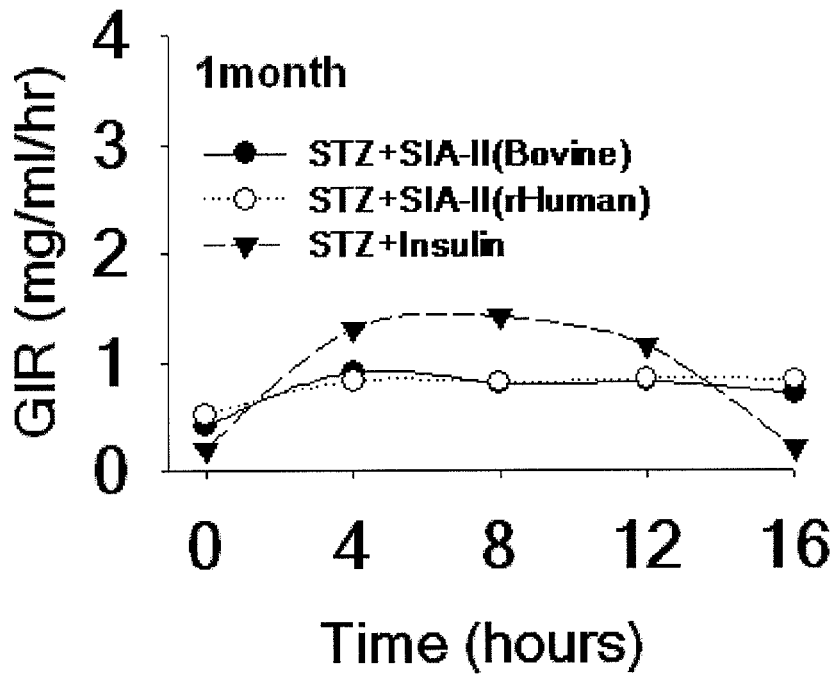
Figure 16C:
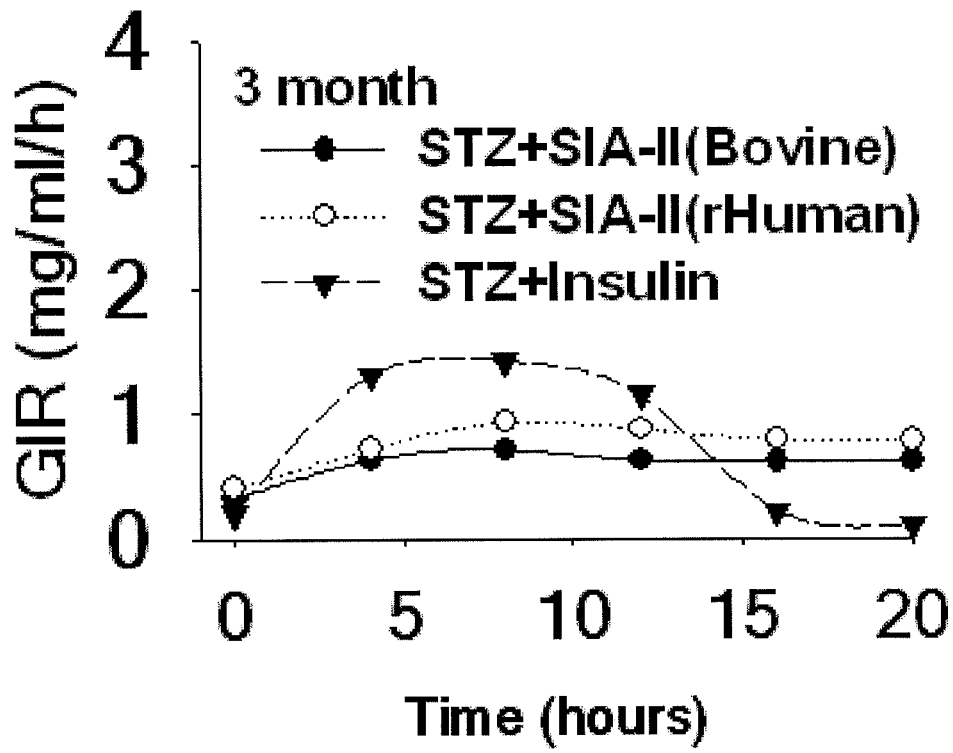

FIGS. 16a-c are line graphs showing hyperglycemic clamp studies after treatment with supramolecular insulin assembly II. GIR-glucose infusion rate (mg/kg/min)

Figure 17A:
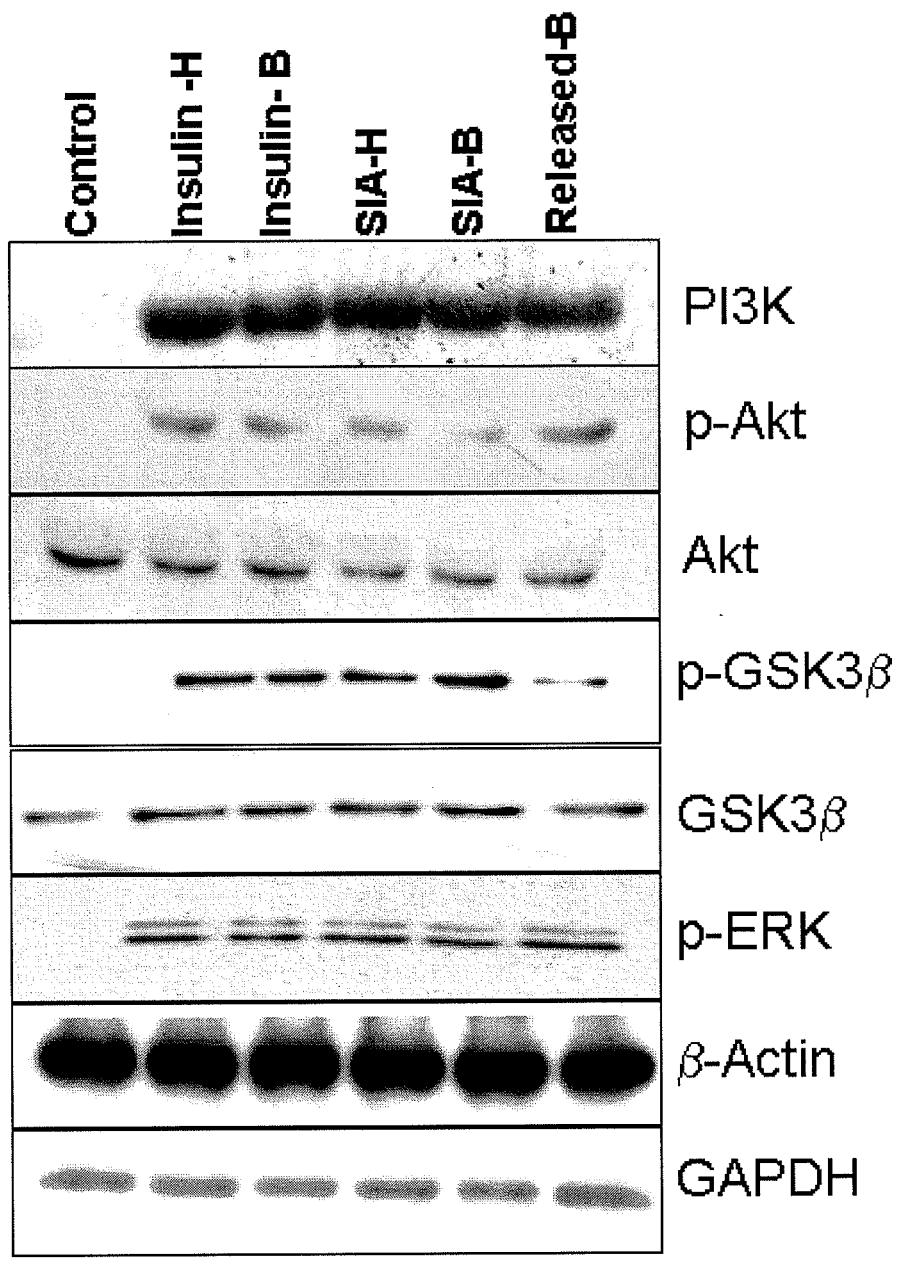
Figure 17B:
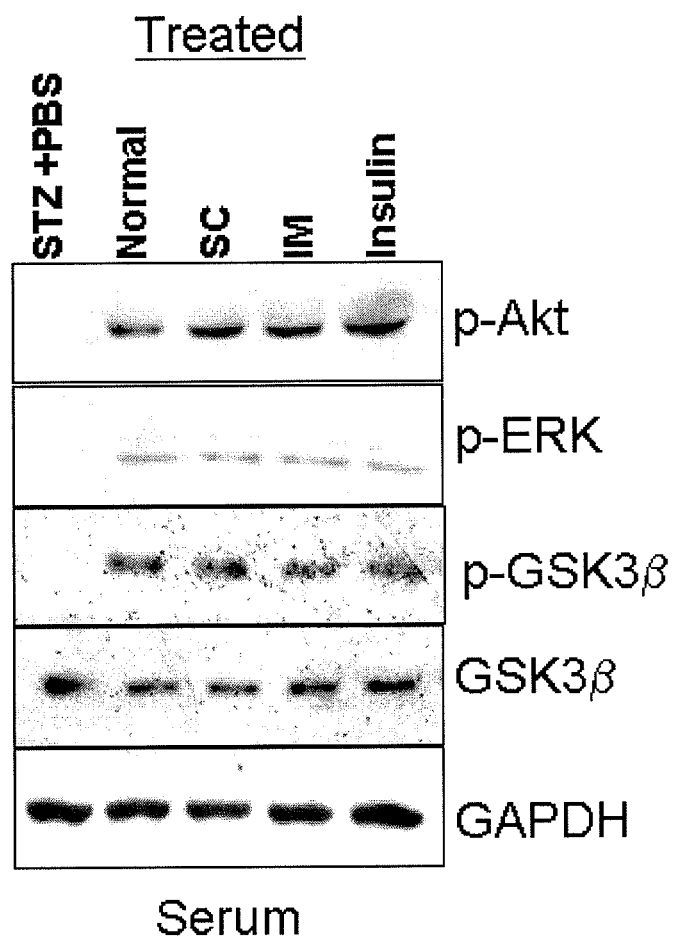

FIGS. 17a-b are photographs showing Western blot (WB) analysis of cultured adipocytes for insulin signaling cascade Adipocytes treated with (a) PBS, insulin, SIA-II, insulin released from SIA-II, (b) serum as indicated, and analysed for insulin signaling.

Figure 18A:
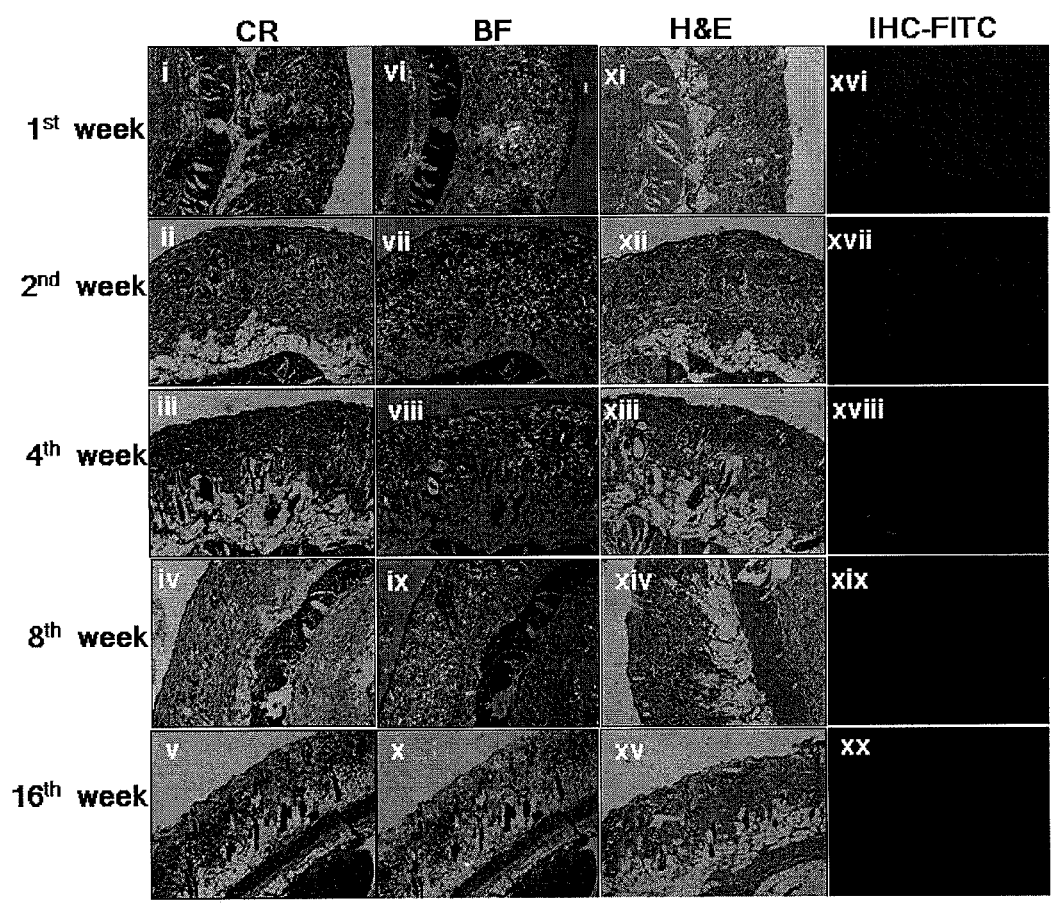
Figure 18B:
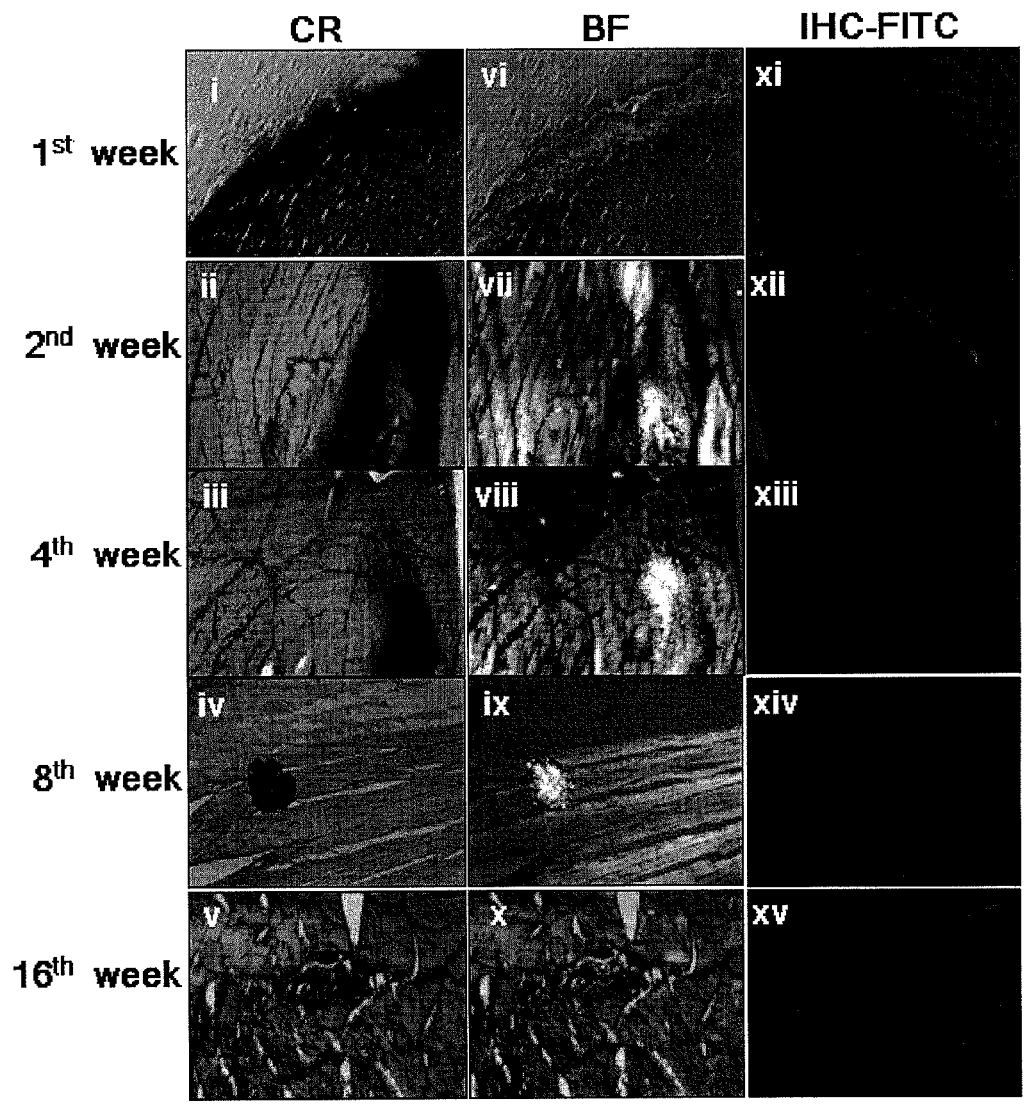

FIGS. 18a-b are a series of photomicrographs showing male Wistar rats rendered diabetic with STZ and treated subcutaneously with supramolecular insulin assembly II (alternatively pre-amyloid insulin II) and checked for the presence of residual supramolecular insulin assembly using Congo red and the occurrence of inflammation respectively.

18a: Subcutaneous Congo red stained sections (i-v), Congo red Birefringence (vi-x), H & E stained sections (xi-xv), and Immunostained section (xvi-xx) from week 1 to week 12.

18b: Intramuscular sections stained with Congo red (i-v), Congo red Birefringence (vi-x) H & E stained sections (xi-xv), and Immunostained section (xvi-xx) from week 1 to week 12.

Figure 19A:
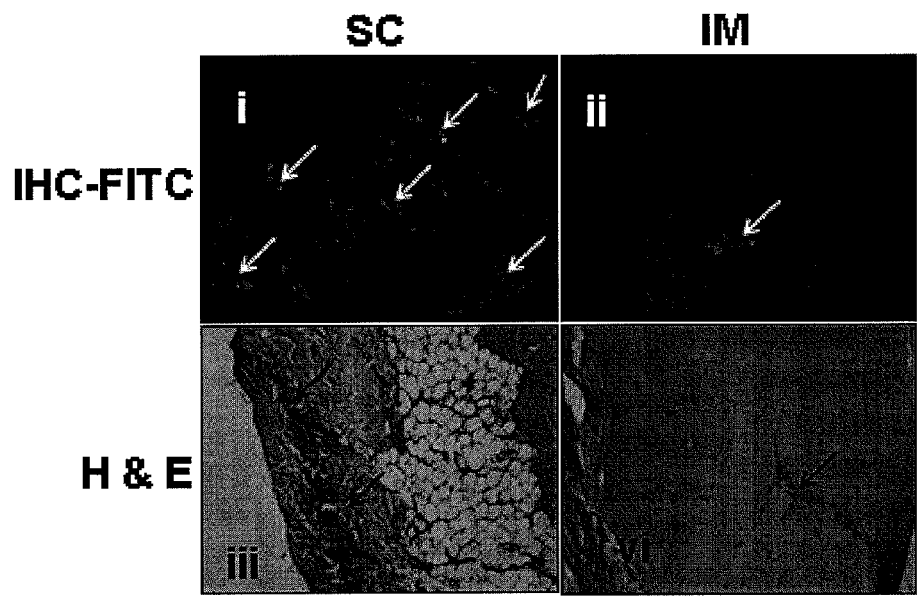
Figure 19B:
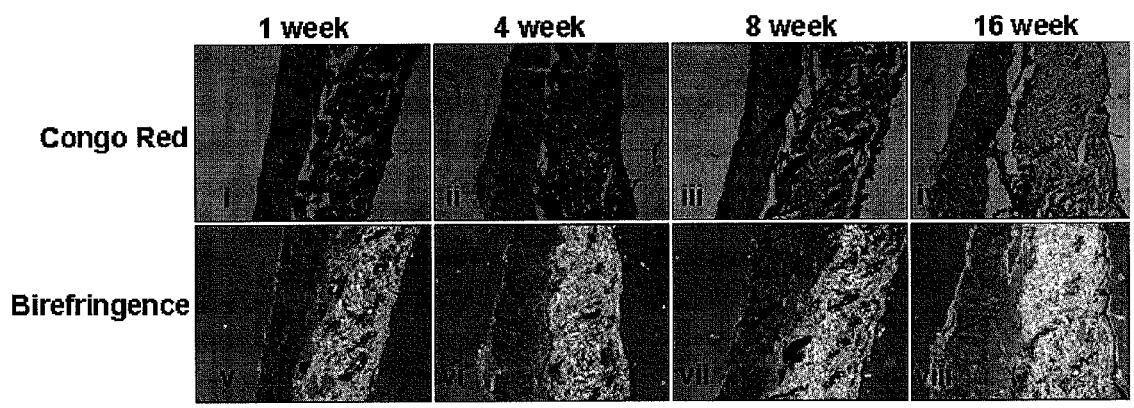

FIGS. 19a-b are a series of photomicrographs.

FIG. 19a shows LPS from E coli was injected to subcutaneous and muscle tissues as a positive control for infiltration of inflammatory cells. Immunostained SC (i) and IM (ii) section, and H&E stained SC (iii) and IM (iv) section.

FIG. 19b shows insulin amyloid fibers formed at pH 2.0 injected SC were monitored for 1, 4, 8 and 12 weeks using Congo red stained sections (i-iv) and Congo Red Birefringence (v-viii).

Figure 20A:
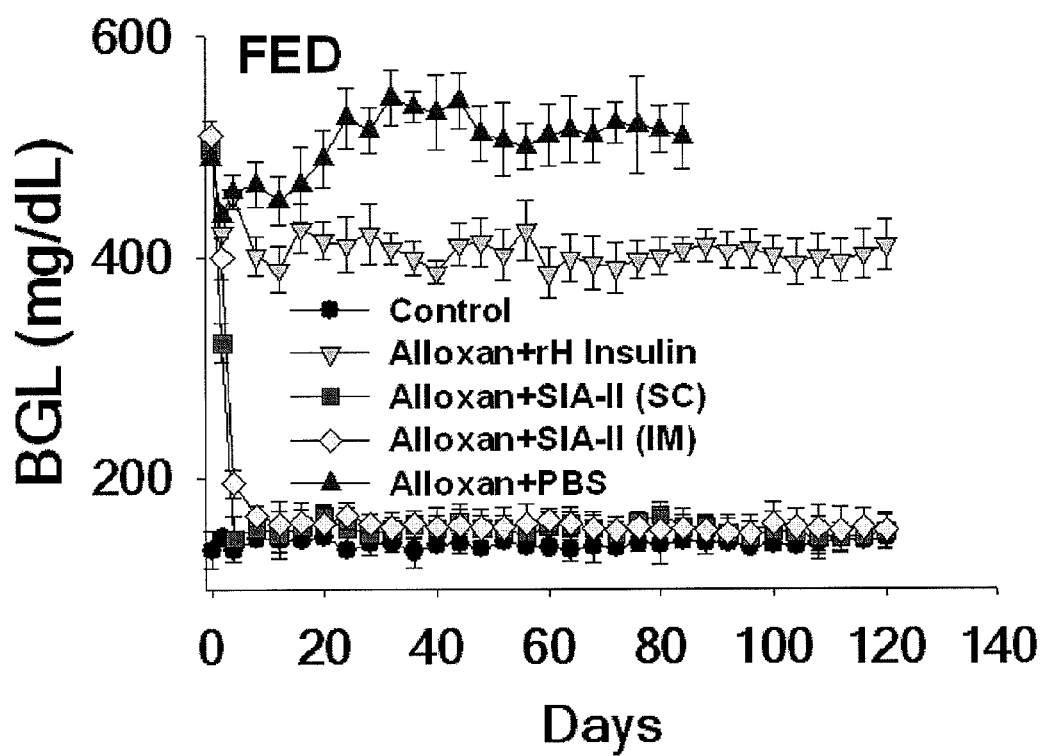
Figure 20B:
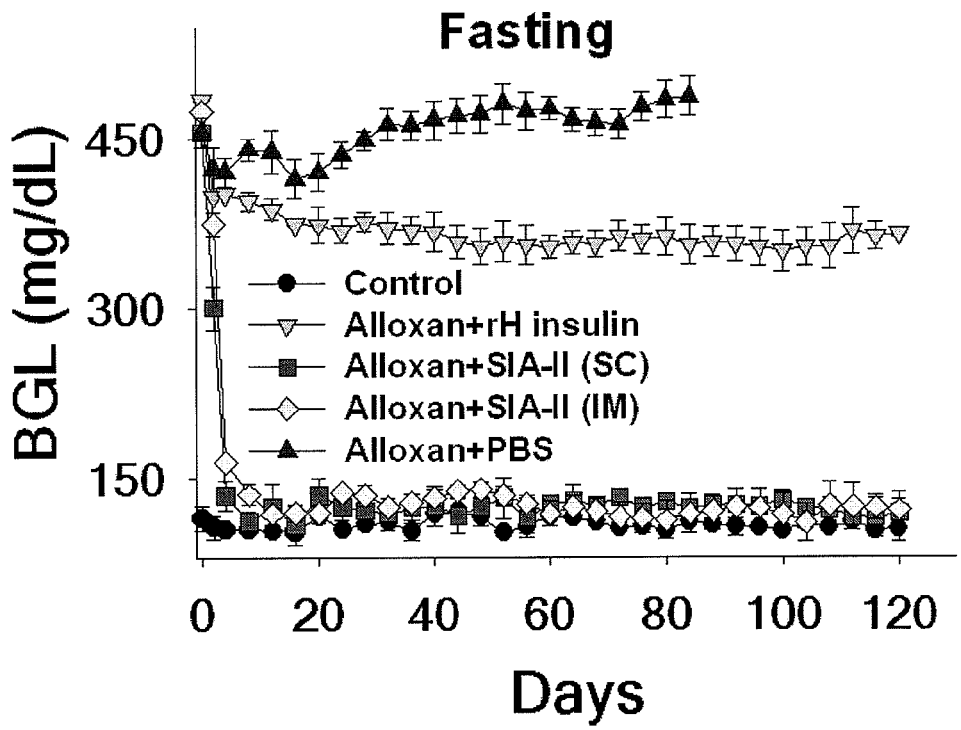
Figure 20C:
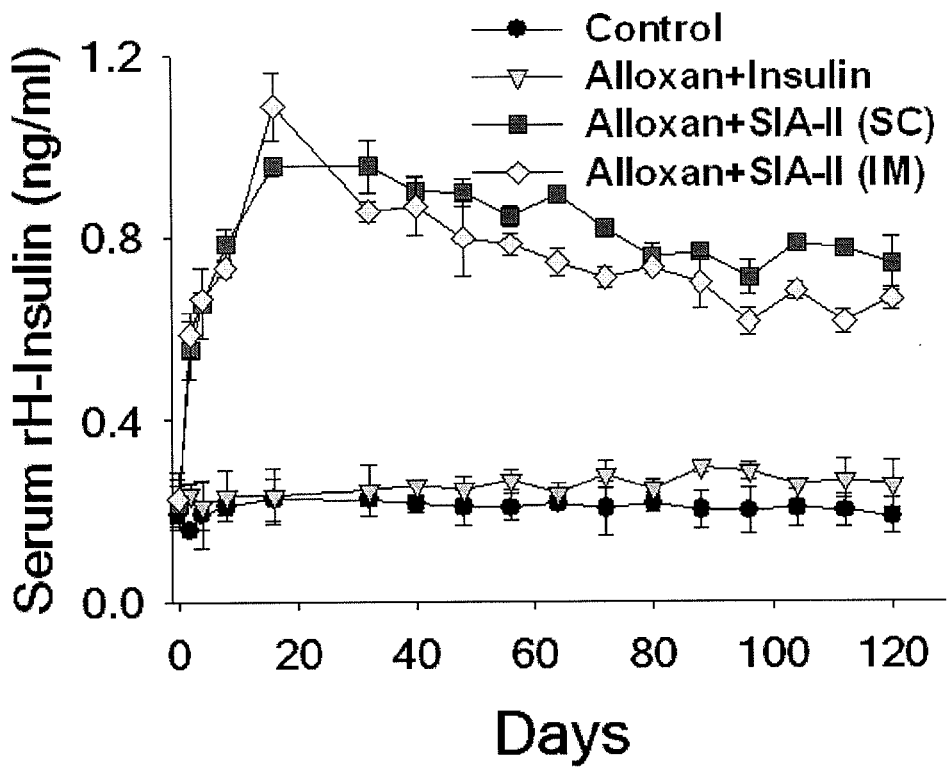

FIGS. 20a-c are line graphs showing blood glucose profile of rH-insulin SIA-II treatment of rats rendered diabetic using Alloxan.

20a: Fasting
20b: Non-fasting Blood
20c: Human Insulin quantification in serum using solid state ELISA as per the manufacturer's protocol.

Figure 21:
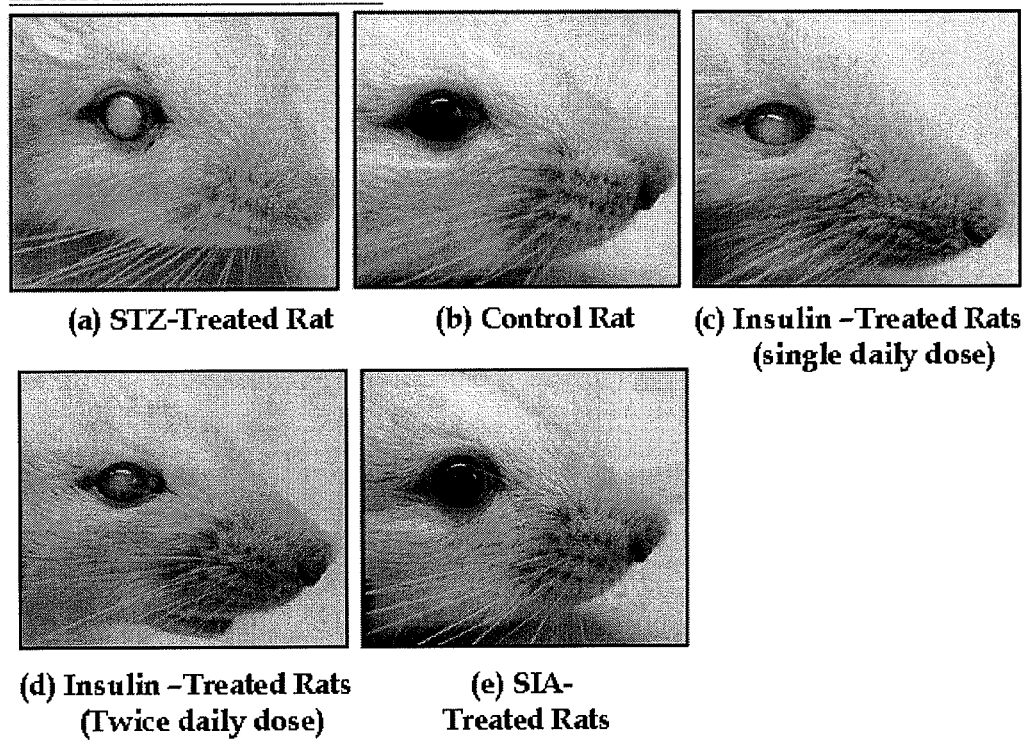
Figure 22:
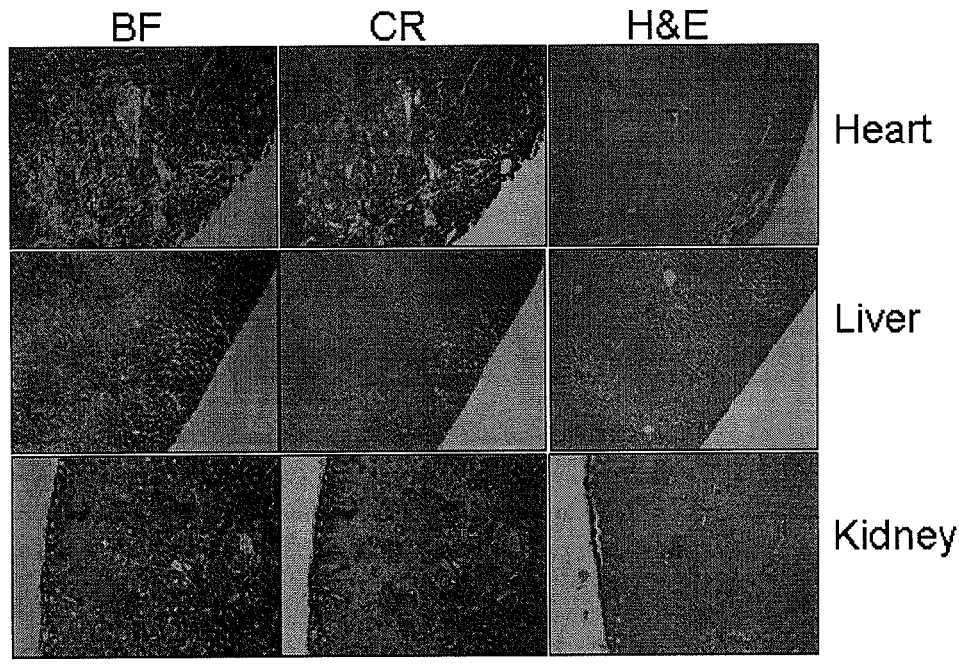

FIGS. 21a-e are a series of photographs showing monitoring cataract formation under the following conditions:
(a) STZ-treated Rat.
(b) Control Rat.
(c)-(d) Insulin-treated Rats.
(e) Supramolecular insulin assembly treated Rats FIG. 22 is a series of photomicrographs showing heart, kidney and liver tissue were sectioned and examined for amyloid deposition by staining with CR. Cellular morphology was also assessed using H&E Staining. Congo red Birefringence of heart kidney and liver (i-iii), Congo red stained sections (iv-vi), H&E staining of heart, kidney and liver (vii-ix).

Figure 23:
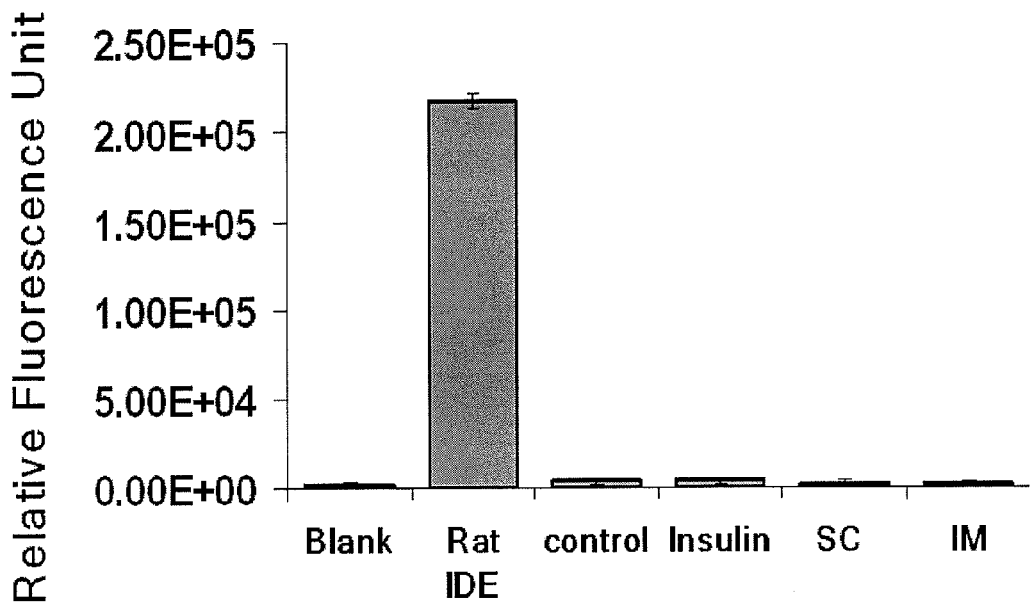

FIG. 23 is a bar graph showing detection of Rat Insulin degrading enzyme (IDE) after treatment with SIA-II.

Figure 24:
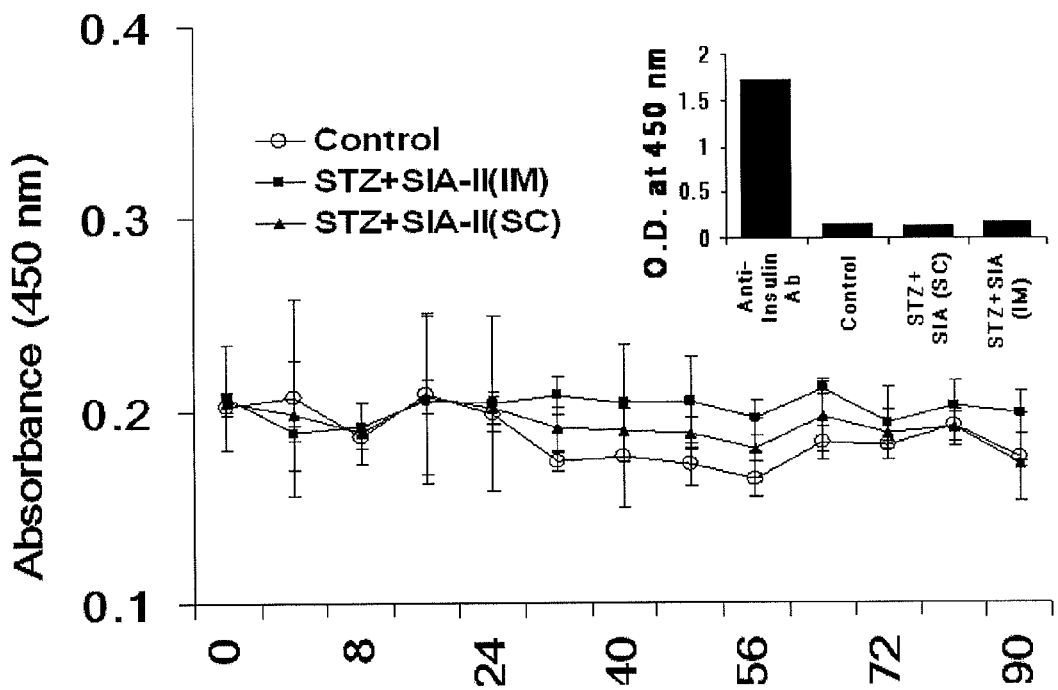

FIG. 24 is a line graph with a bar graph inset showing screening for anti-insulin antibody in Rat serum treated with SIA-II.

Figure 25:
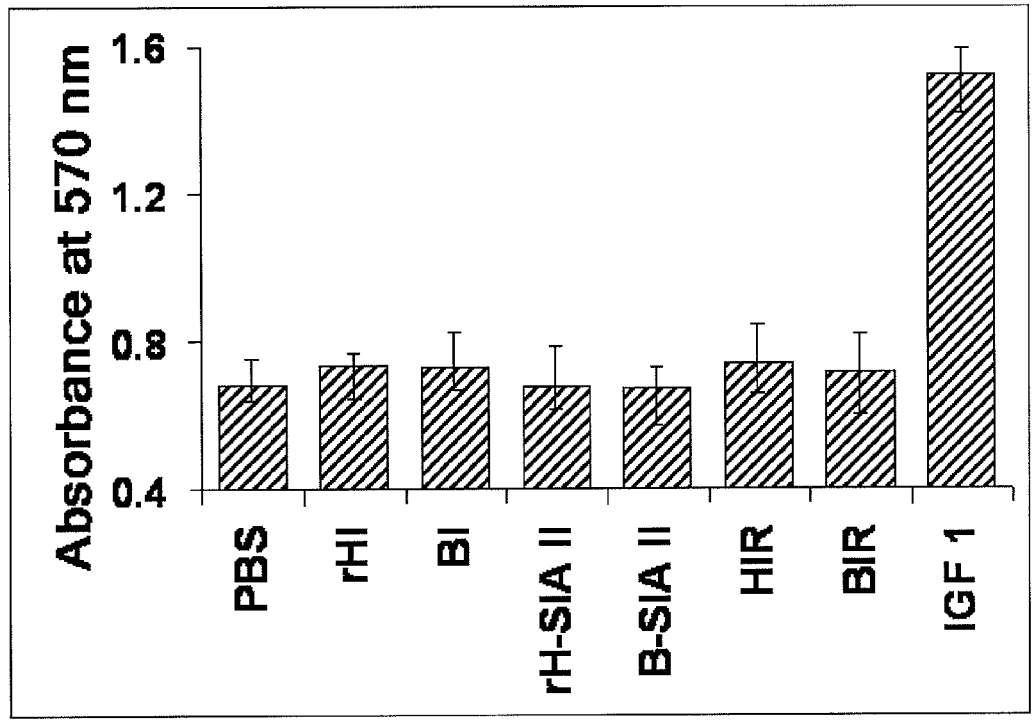

FIG. 25 is a bar graph showing the results of a MTT assay for cell proliferation: MCF 7 cells were assayed for their growth kinetics by the administration of PBS, pH 7.4, human/bovine insulin (20 nM), SIA II (Human/bovine insulin), released insulin monomers from SIA II (20 nM), Insulin like Growth Factor I (IGF-1) (6 ng/ml).

Figure 26A:
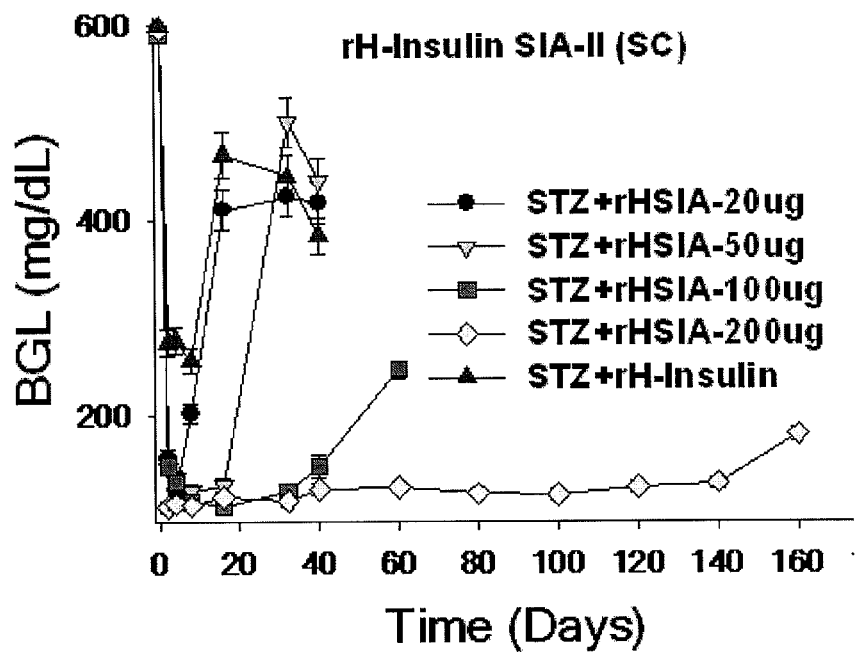
Figure 26B:
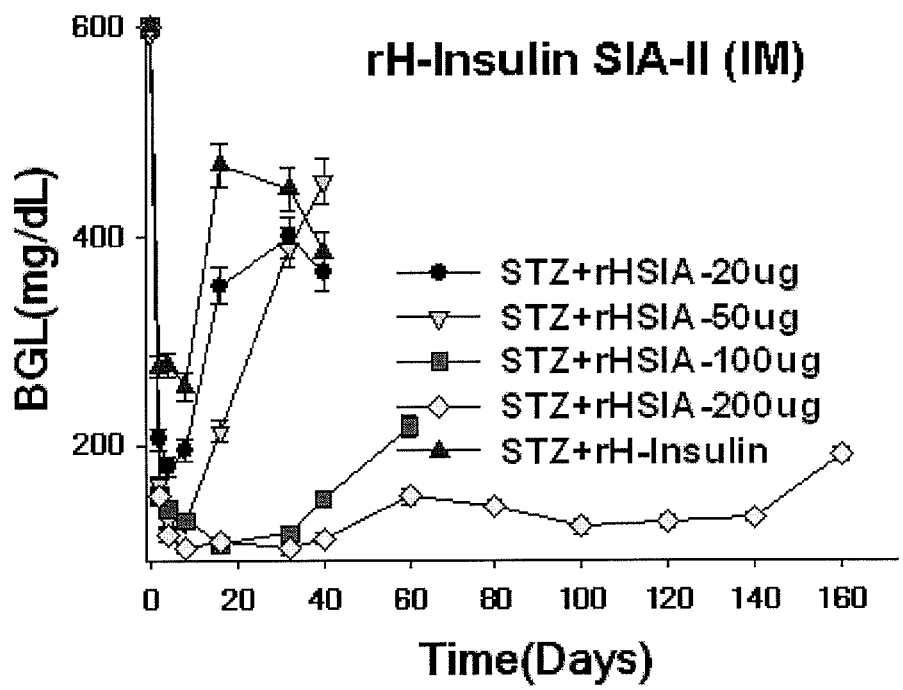
Figure 26C:
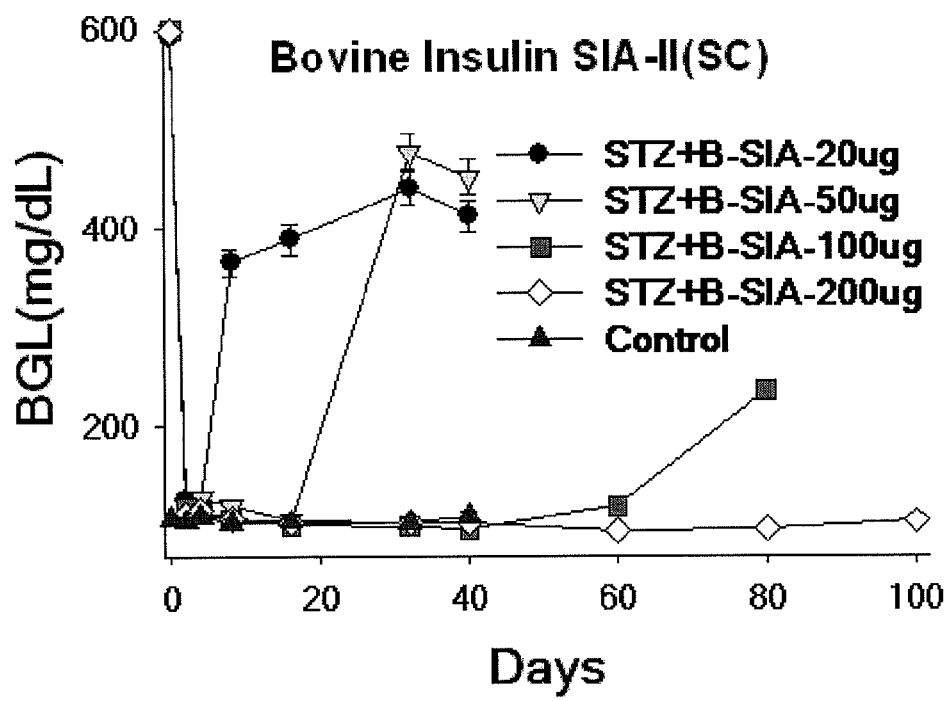

FIGS. 26a-c are line graphs showing blood glucose level in response to various dosages of supramolecular insulin assembly administered both subcutaneously and intramuscularly in mice rendered diabetic using STZ. Human SIA-II injected (a) subcutaneously, (b) intramuscularly and (c) bovine SIA-II subcutaneously at indicated dosage.

Figure 27:
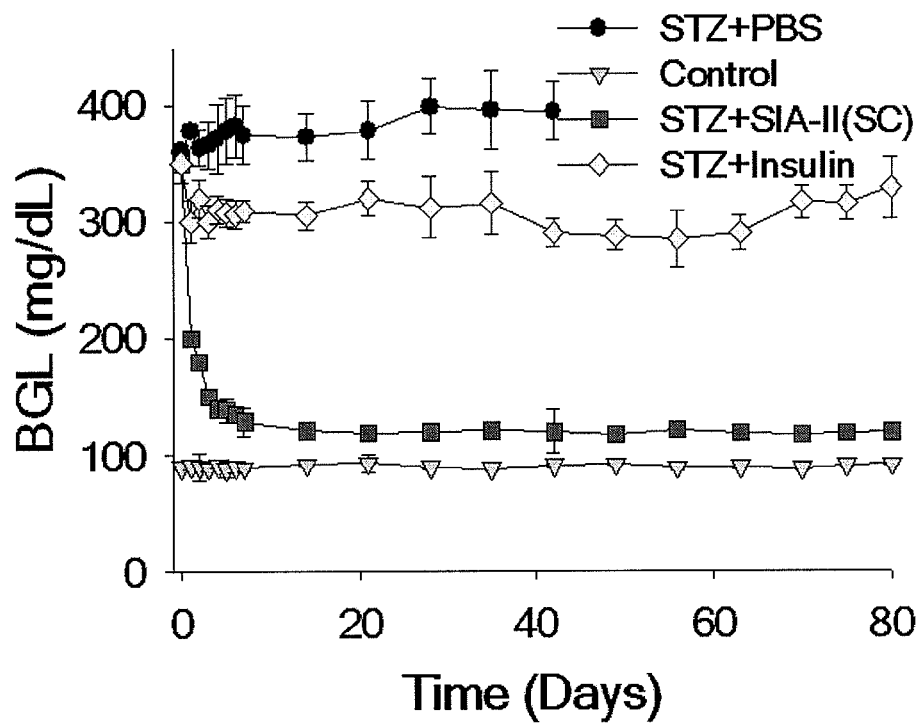

FIG. 27 is a line graph showing blood glucose level in response to supramolecular insulin assembly administered subcutaneously in rabbit rendered diabetic using STZ.

Figure 28A:
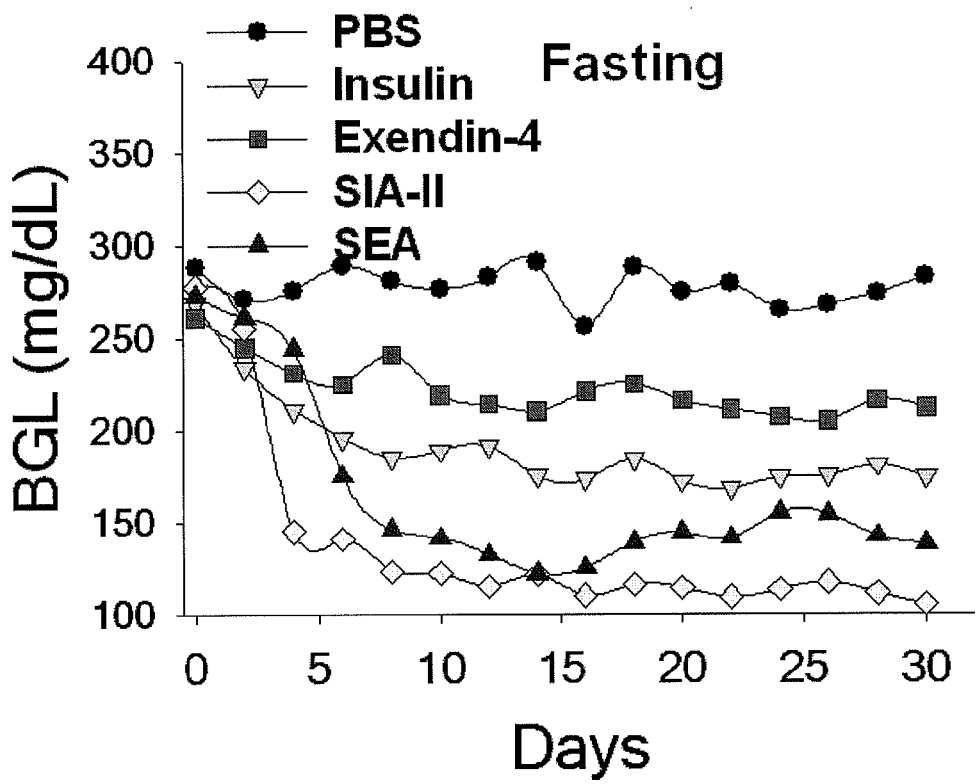
Figure 28B:
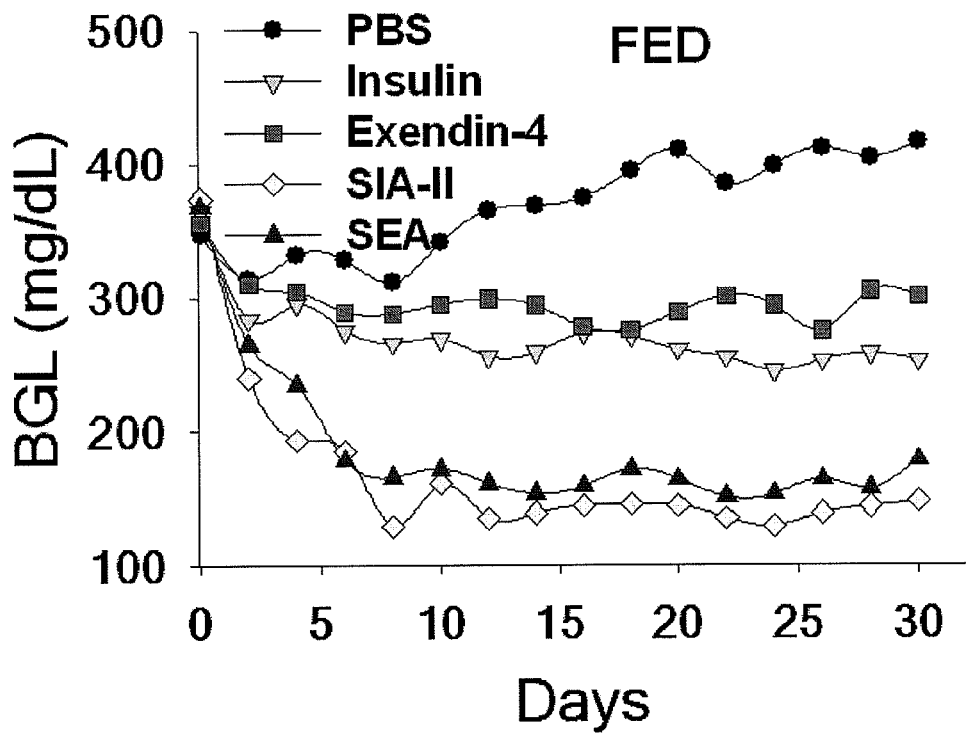

FIGS. 28a-b are line graphs showing blood glucose profile of Type II diabetic rats given various treatments as indicated in the figure, over a period of 35 days.

Figure 29A:
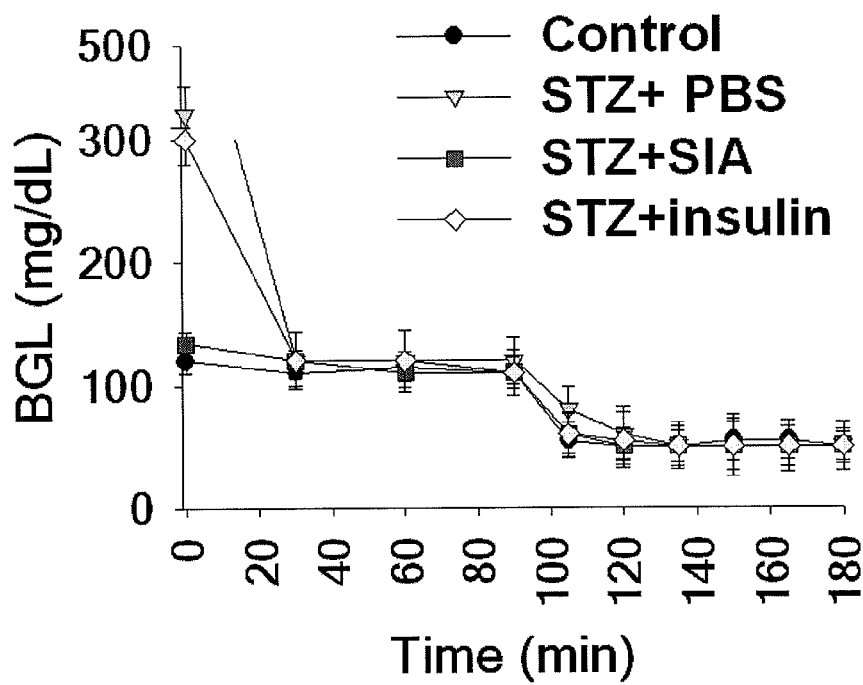
Figure 29B:
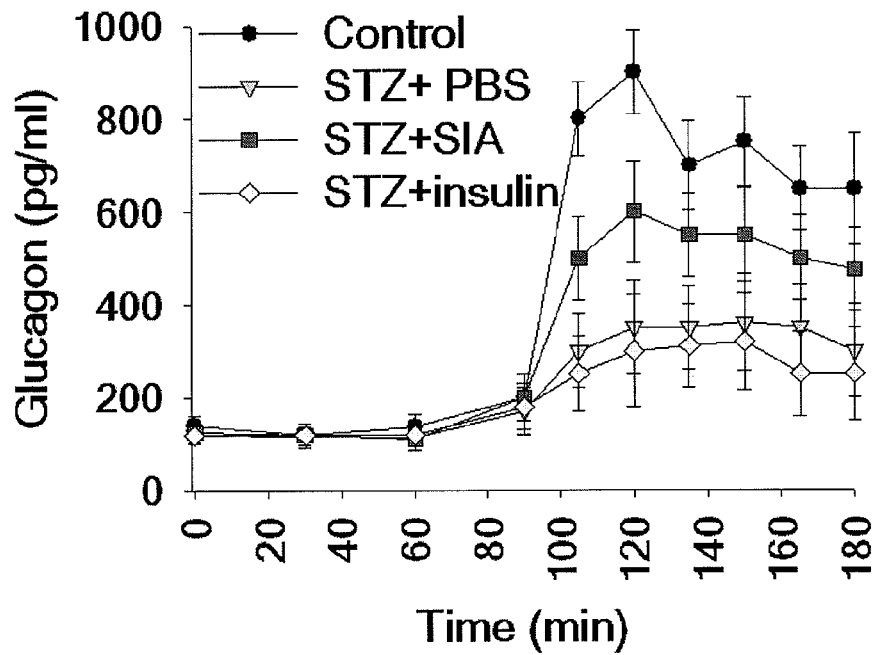
Figure 29C:
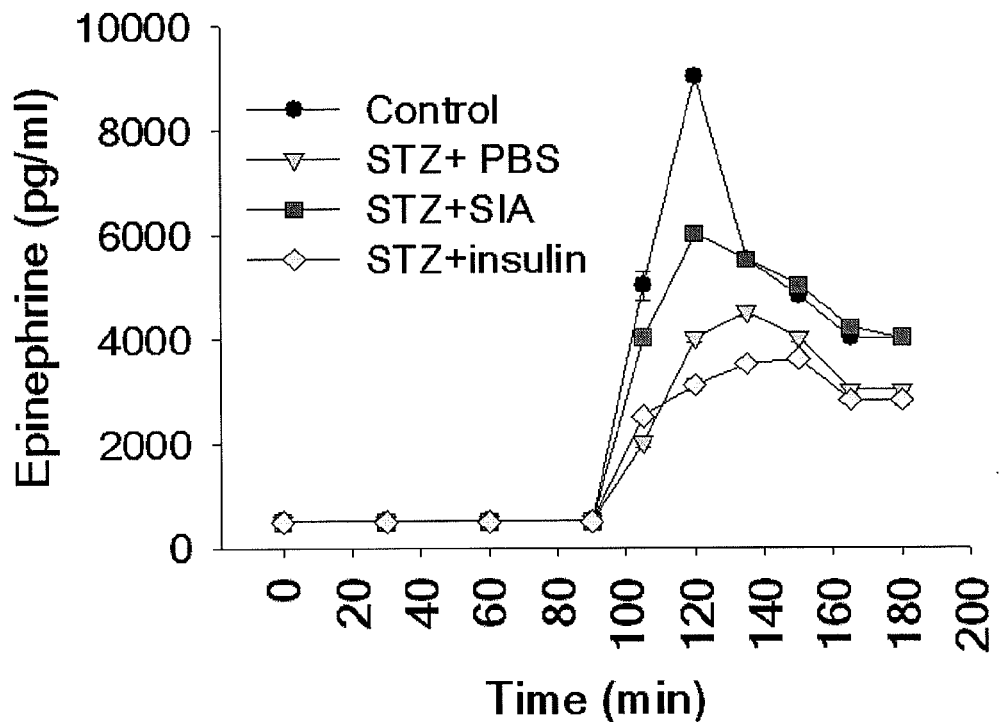

FIGS. 29a-c are line graphs showing monitoring insulin counter regulatory response using Hyperinsulinemic Euglycemic/Hypoglycemic clamp studies
(a) Blood glucose level
(b) Glucagon level
(c) Epinephrine level.

Figure 30:
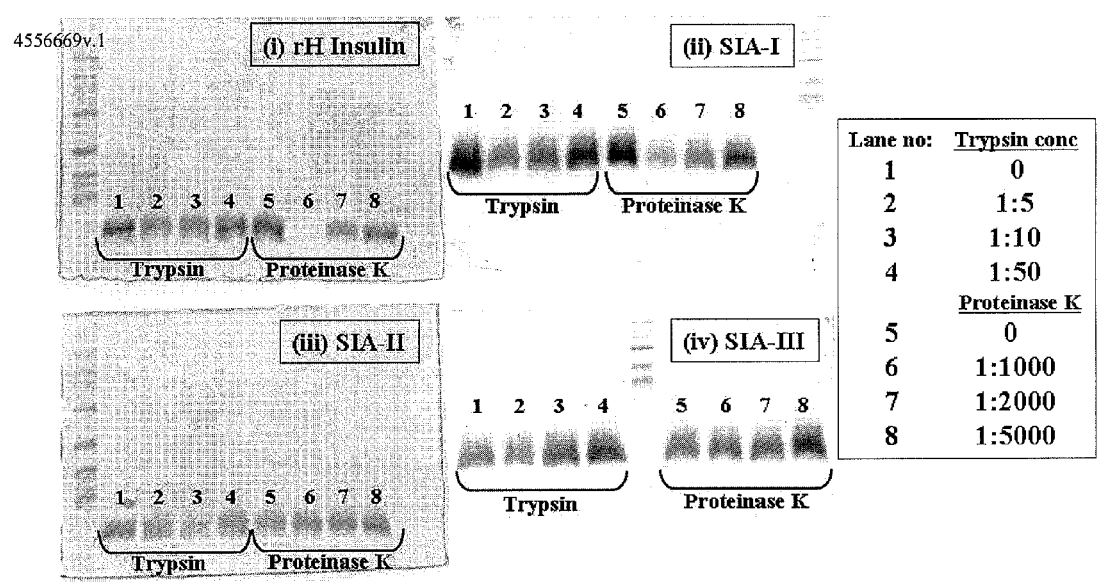

FIG. 30 is a series of photographs of electrophoretic gels showing 20% coomassie stained bands showing cleavage pattern of (i) rH insulin, (ii) SIA-I, (iii) SIA-II and (iv) SIA-III with different dilutions of 2 mg/ml Trypsin and Proteinase K.

DETAILED DESCRIPTION OF THE INVENTION

The present invention provides protein therapeutics for treatment of diabetes and other chronic diseases/disorders. The present invention particularly provides supramolecular insulin assembly (SIA), wherein the SIA comprises the insoluble and aggregated oligomeric form of insulin. The present invention also provides the supramolecular exendin-4 assembly (SEA), wherein the SEA comprises insoluble and aggregated oligomeric form of exendin-4. The present invention also provides the pharmaceutical compositions comprising supramolecular insulin assembly and/or supramolecular exendin-4 assembly.

The present invention also provides the feasibility of treating Type II diabetes.

The term "supramolecular insulin assembly" or "SIA" used herein refers to the insoluble and aggregated oligomeric form of insulin. The sequence of human insulin is known (e.g., Nicol et al., Nature. 1960 Aug. 6; 187:483-5) as are the sequences of insulin from other animals (e.g., pig, mouse, dog, cat). Exendin-4 and agonists thereof are described in U.S. Pat. No. 6,506,724.

The term "supramolecular insulin assembly" or "SIA" used herein refers to the insoluble and aggregated oligomeric form of insulin, wherein the higher order oligomeric form of SIA-II and III, prevents the proteases to cleave them. Resistance of SIA-II and SIA-II to cleavage by Trypsin and Proteinase K further demonstrate the difference in the structural organization of these oligomers. rH Insulin and SIA-I are more susceptible to cleavage by the proteases as compared to SIA-II and SIA-III, which adopt an higher order oligomeric form resistant to protease action.

The term "supramolecular insulin assembly" or "SIA" used herein refers to supramolecular insulin assembly I, II and III, which are the insoluble and aggregated oligomeric form of insulin.

The term "SIA I" used herein refers to "supramolecular insulin assembly" at stage I, wherein "SIA I" comprises the insoluble and aggregated oligomeric form of insulin, wherein the oligomers consists of elongated clusters having pearl like arrangement of insulin monomer.

The term "SIA II" used herein refers to "supramolecular insulin assembly" at stage II, wherein "SIA II" comprises the insoluble and aggregated oligomeric form of insulin, wherein the oligomers of insulin are arranged as a linear association of the above mentioned elongated clusters, having a unique entity with a supra-oligomeric structural organization.

The term "SIA III" used herein refers to "supramolecular insulin assembly" at stage III, wherein "SIA III" consists of a dense, linear association of oligomeric form of insulin.

SIA at stage III i.e. SIA III consist of about 90% of SIA-II.

In accordance with the present invention, one embodiment provides a supramolecular insulin assembly (SIA) useful as protein therapeutics for the treatment of metabolic disorders selected from the group consisting of type 1, type 2 diabetes mellitus and complications thereof, wherein said assembly comprises insoluble and aggregated oligomeric form of insulin.

In another embodiment of the present invention, there is provided a supramolecular insulin assembly (SIA) useful as protein therapeutics for the treatment of metabolic disorders selected from the group consisting of type 1, type 2 diabetes mellitus and complications thereof, wherein the assembly comprises insoluble and aggregated oligomeric form of insulin as SIA I, SIA II, SIA III or combination thereof, wherein SIA I consists of elongated clusters having pearl like arrangement of insulin monomer, SIA II consists of linear association of elongated clusters having pearl like arrangement of insulin monomer and SIA III consists of about 90% SIA-II, that is a dense, linear association of insulin oligomers.

In another embodiment of the present invention, there is provided a supramolecular insulin assembly (SIA) useful as protein therapeutics for the treatment of metabolic disorders selected from the group consisting of type 1, type 2 diabetes mellitus and complications thereof, wherein the assembly comprises insoluble and aggregated oligomeric form of insulin as SIA I, wherein SIA I consists of elongated clusters having pearl like arrangement of insulin monomer.

In yet another embodiment of the present invention, there is provided a supramolecular insulin assembly (SIA) useful as protein therapeutics for the treatment of metabolic disorders selected from the group consisting of type 1, type 2 diabetes mellitus and complications thereof, wherein the assembly comprises insoluble and aggregated oligomeric form of insulin as SIA II, wherein SIA II consists of linear association of elongated clusters having pearl like arrangement of insulin monomer.

In still yet another embodiment of the present invention, there is provided a supramolecular insulin assembly (SIA) useful as protein therapeutics for the treatment of metabolic disorders selected from the group consisting of type 1, type 2 diabetes mellitus and complications thereof, wherein the assembly comprises insoluble and aggregated oligomeric form of insulin as SIA III, wherein SIA III consists dense, linear association of insulin oligomers.

One embodiment provides the supramolecular insulin assembly (SIA), wherein the insulin is recombinant human insulin, bovine or pig insulin, or mutants/analogs of insulin.

One embodiment of the present invention provides the supramolecular insulin assembly (SIA), wherein the assembly comprises insoluble and aggregated oligomeric form of insulin, wherein the assembly release insulin at a rate ranging from about 0.2 to 0.6 IU per hour in vitro.

One embodiment of the present invention provides the supramolecular insulin assembly (SIA), wherein the assembly comprises insoluble and aggregated oligomeric form of insulin as SIA I, SIA II, SIA III or combination thereof, wherein SIA I consists of elongated clusters having pearl like arrangement of insulin monomer, SIA II consists of linear association of elongated clusters having pearl like arrangement of insulin monomer and SIA III consists of about 90% SIA-II, that is a dense, linear association of insulin oligomers, wherein the assembly release insulin at a rate ranging from about 0.2 to 0.6 IU per hour in vitro.

One embodiment of the present invention provides the supramolecular insulin assembly (SIA), wherein the assembly comprises insoluble and aggregated oligomeric form of insulin, wherein the assembly releases insulin at a rate ranging from 0.1 to 5.4 ng/ml, wherein rate of release of insulin is in the range of for about 7 to 180 days, in vivo.

One embodiment of the present invention provides the supramolecular insulin assembly (SIA), wherein the assembly comprises insoluble and aggregated oligomeric form of insulin as SIA I, SIA II, SIA III or combination thereof, wherein SIA I consists of elongated clusters having pearl like arrangement of insulin monomer, SIA II consists of linear association of elongated clusters having pearl like arrangement of insulin monomer and SIA III consists of about 90% SIA-II, that is a dense, linear association of insulin oligomers, wherein the assembly releases insulin at a rate ranging from 0.1 to 5.4 ng/ml, wherein rate of release of insulin is in the range of for about 7 to 180 days, in vivo.

One embodiment of the present invention provides the supramolecular insulin assembly (SIA), wherein the assembly comprises insoluble and aggregated oligomeric form of insulin, wherein the assembly release insulin at a rate ranging from about 0.2 to 0.6 IU per hour in vitro, wherein rate of release of insulin is in the range of 4-5.4 ng/ml for at least 7-10 days.

One embodiment of the present invention provides the supramolecular insulin assembly (SIA), wherein the assembly comprises insoluble and aggregated oligomeric form of insulin as SIA I, SIA II, SIA III or combination thereof, wherein SIA I consists of elongated clusters having pearl like arrangement of insulin monomer, SIA II consists of linear association of elongated clusters having pearl like arrangement of insulin monomer and SIA III consists of about 90% SIA-II, that is a dense, linear association of insulin oligomers, wherein the assembly release insulin at a rate ranging from about 0.2 to 0.6 IU per hour in vitro, wherein rate of release of insulin is in the range of 4-5.4 ng/ml for at least 7-10 days.

In yet another embodiment of the present invention, there is provided a supramolecular insulin assembly (SIA) useful as protein therapeutics for the treatment of metabolic disorders selected from the group consisting of type 1, type 2 diabetes mellitus and complications thereof, wherein the assembly comprises insoluble and aggregated oligomeric form of insulin as SIA II, wherein SIA II consists of linear association of elongated clusters having pearl like arrangement of insulin monomer, wherein rate of release of insulin is in the range of 0.5-1.8 ng/ml for at least 160 days.

In still yet another embodiment of the present invention, there is provided a supramolecular insulin assembly (SIA) useful as protein therapeutics for the treatment of metabolic disorders selected from the group consisting of type 1, type 2 diabetes mellitus and complications thereof, wherein the assembly comprises insoluble and aggregated oligomeric form of insulin as SIA III, wherein SIA III consists dense, linear association of insulin oligomers, wherein rate of release of insulin is in the range of 0.1-0.7 ng/ml for at least 180 days.

In yet another embodiment of the present invention, there is provided a supramolecular insulin assembly (SIA) useful as protein therapeutics for the treatment of metabolic disorders selected from the group consisting of type 1, type 2 diabetes mellitus and complications thereof, wherein the assembly comprises insoluble and aggregated oligomeric form of insulin as SIA II, wherein SIA II consists of linear association of elongated clusters having pearl like arrangement of insulin monomer, wherein the assembly upon administration to diabetic subjects maintains near-normoglycemic level (120±30 mg/dl) for at least 160 days in a subject in need thereof.

The supramolecular insulin assembly (SIA) as disclosed in the present invention, wherein a single dose of the assembly upon administration maintains near-normoglycemic level (120±30 mg/dl) for at least 7 to 180 days in a subject in need thereof, wherein concentration of the assembly in the dose is in the range of 25 to 750 µg.

The supramolecular insulin assembly (SIA) as disclosed in the present invention, wherein a single dose of the assembly upon administration maintains near-normoglycemic level (120±30 mg/dl) for at least 160 days in a subject in need thereof, wherein concentration of the assembly in the dose is in the range of 150 to 250 µg.

One embodiment of the present invention provides a supramolecular exendin-4 assembly (SEA) useful as protein therapeutics for the treatment of diabetes, wherein the assembly comprises insoluble and aggregated oligomeric form of exendin-4.

Another embodiment of the present invention provides the supramolecular insulin assembly, wherein the assembly is a non cytotoxic, non immunogenic, non-apoptotic and non-mitogenic prodrug.

Another embodiment of the present invention provides the supramolecular insulin assembly, wherein the assembly is a non cytotoxic, non immunogenic, non-apoptotic and non-mitogenic prodrug.

One embodiment of the present invention provides a pharmaceutical composition for the treatment of metabolic disorders selected from the group consisting of type 1, type 2 diabetes mellitus and complications thereof, the composition comprising therapeutically effective amount of the supramolecular insulin assembly (SIA) as disclosed in the present invention.

Another embodiment of the present invention provides a pharmaceutical composition for the treatment of metabolic disorders selected from the group consisting of type 1, type 2 diabetes mellitus and complications thereof, the composition comprising therapeutically effective amount of the supramolecular insulin assembly-II (SIA-II).

Yet another embodiment of the present invention provides a pharmaceutical composition for the treatment of metabolic disorders selected from the group consisting of type 1, type 2 diabetes mellitus and complications thereof, the composition comprising therapeutically effective amount of the supramolecular insulin assembly (SIA) and supramolecular exendin-4 assembly (SEA).

Still yet another embodiment of the present invention provides a pharmaceutical composition for the treatment of metabolic disorders selected from the group consisting of type 1, type 2 diabetes mellitus and complications thereof, the composition comprising therapeutically effective amount of the supramolecular insulin assembly (SIA) and supramolecular exendin-4 assembly (SEA).

Further embodiment of the present invention provides a pharmaceutical composition for the treatment of metabolic disorders selected from the group consisting of type 1, type 2 diabetes mellitus and complications thereof, the composition comprising therapeutically effective amount of supramolecular exendin-4 assembly (SEA).

The pharmaceutical composition(s) disclosed in the present invention optionally comprises pharmaceutically acceptable carriers, additives or diluents.

The pharmaceutical composition(s) disclosed in the present invention is administered intramuscularly, intradermally or subcutaneously.

The pharmaceutical composition(s) disclosed in the present invention is administered through a device capable of releasing the said composition, wherein said device is selected from a group consisting of pumps, catheters, patches and implants.

In one embodiment, there is provided a process of preparation of supramolecular insulin assembly (SIA), the process comprising dissolving insulin at a temperature of about 25 to 60° C. in a solution having pH in the range of about 1.5 to 7.8; and incubating the above for a period of about 6 to 48 hours with constant shaking to obtain Supramolecular Insulin Assembly (SIA), wherein SIA comprises insoluble and aggregated oligomeric form of insulin The process of preparation of supramolecular insulin assembly (SIA) disclosed in the present invention, wherein the process further comprises washing the SIA with PBS; and re-suspending the washed SIA in PBS.

The process of preparation of supramolecular insulin assembly (SIA) disclosed in the present invention, wherein incubation period is 10 hours.

In another embodiment of the present invention, there is provided a process of preparation of supramolecular exendin-4 assembly (SEA), the process comprising dissolving exendin-4 at a temperature of about 25 to 60° C. in a solution having pH in the range of about 2.0 to 7.6; and incubating the above for a period of 6 to 192 hours with constant shaking to obtain Supramolecular Exendin-4 Assembly (SEA), wherein SEA comprises insoluble and aggregated oligomeric form of Exendin-4

The process of preparation of supramolecular exendin-4 assembly disclosed in the present invention further comprises washing the SEA with PBS; and re-suspending the washed SEA in PBS.

The process of preparation of supramolecular exendin-4 assembly (SEA) disclosed in the present invention, wherein the incubation period is 148 hours.

The process preparation of the supramolecular insulin assembly (SIA) disclosed in the present invention, wherein the solution is selected from a group consisting of hydrochloric or acetic acid in water having pH in the range of about 1.5 to 2.5; sodium acetate buffer having pH in the range of about 3.5 to 5.5; phosphate buffer (PBS) having pH 6-7.5, and citrate buffer having pH in the range of about 4 to 6.

The process preparation of supramolecular exendin-4 assembly (SEA) disclosed in the present invention, wherein the solution is selected from a group consisting of hydrochloric or acetic acid in water having pH in the range of about 1.5 to 2.5; sodium acetate buffer having pH in the range of about 3.5 to 5.5; phosphate buffer (PBS) having pH 6-7.5, and citrate buffer having pH in the range of about 4 to 6.

The process preparation of the supramolecular insulin assembly (SIA) disclosed in the present invention, wherein the temperature is 37° C.

The process preparation of supramolecular exendin-4 assembly (SEA) disclosed in the present invention, wherein the temperature is 37° C.

The process preparation of the supramolecular insulin assembly (SIA) disclosed in the present invention, wherein pH of said solution is 7.2.

The process preparation of supramolecular exendin-4 assembly (SEA) disclosed in the present invention, wherein pH of said solution is 7.2.

The process preparation of the supramolecular insulin assembly (SIA) disclosed in the present invention, wherein said period is 6-192 hours.

The process preparation of the supramolecular insulin assembly (SIA) disclosed in the present invention, wherein said period is 6-192 hours.

One embodiment of the present invention relates to a method for treating metabolic disorders selected from the group consisting of type 1, type 2 diabetes mellitus and complications thereof, wherein the method comprising administering to a subject in need thereof a therapeutically effective amount of the pharmaceutical composition comprising the supramolecular insulin assembly, which is effective for the alleviation of the disorder.

Yet another embodiment of the present invention provides a method for treating metabolic disorders selected from the group consisting of type 1, type 2 diabetes mellitus and complications thereof, wherein the method comprising administering to a subject in need thereof a therapeutically effective amount of the pharmaceutical composition comprising the supramolecular insulin assembly-II (SIA-II), which is effective for the alleviation of the disorder.

Still yet another embodiment of the present invention provides a method for treating metabolic disorders selected from the group consisting of type 1, type 2 diabetes mellitus and complications thereof, wherein the method comprising administering to a subject in need thereof a therapeutically effective amount of the pharmaceutical composition comprising the supramolecular exendin-4, which is effective for the alleviation of the disorder.

Still yet another embodiment of the present invention provides a method for treating metabolic disorders selected from the group consisting of type 1, type 2 diabetes mellitus and complications thereof, wherein the method comprising administering to a subject in need thereof a therapeutically effective amount of the pharmaceutical composition comprising the supramolecular insulin assembly and supramolecular exendin-4 assembly, which is effective for the alleviation of the disorder.

In further embodiment of the present invention, there is provided use of supramolecular insulin assembly for the treatment of metabolic disorders selected from the group consisting of type 1, type 2 diabetes mellitus and complications thereof.

In yet another embodiment of the present invention, there is provided use of supramolecular exendin-4 assembly for the treatment of metabolic disorders selected from the group consisting of type 1, type 2 diabetes mellitus and complications thereof.

In still yet another embodiment of the present invention, there is provided use of supramolecular insulin assembly in combination with supramolecular exendin-4 assembly for the treatment of metabolic disorders selected from the group consisting of type 1, type 2 diabetes mellitus and complications thereof.

In additional embodiment, there is provided the supramolecular insulin assembly (SIA), wherein the assembly shows sharp peak at 1647-1645 cm$^{-1}$ in Fourier Transform infrared spectroscopy (FTIR).

In one embodiment, the present invention provides the supramolecular insulin assembly (SIA), wherein the insulin is recombinant Human insulin.

In another embodiment, the present invention provides the supramolecular insulin assembly (SIA), wherein the insulin is human, bovine or pig insulin.

In yet another embodiment of the present invention there is provided the supramolecular insulin assembly (SIA), wherein the assembly upon administration releases insulin monomers.

Further the present invention provides the supramolecular protein assembly, wherein the peptide in assembly is coupled with a small molecule drug.

One embodiment of the present invention provides the supramolecular protein assembly disclosed in the present invention acts as a prodrug, The pharmaceutical composition disclosed in the present invention comprises pharmaceutically acceptable carriers, additives or diluents.

The pharmaceutical composition disclosed in the present invention is administered intramuscularly or subcutaneously.

The pharmaceutical composition disclosed in the present invention is administered through a device capable of releasing the composition, wherein the device is selected from a group consisting of pumps, catheters and implants.

The pharmaceutical composition disclosed in the present invention, wherein single dose of the composition upon administration releases said protein for prolonged period.

The process of preparation of supramolecular insulin assembly disclosed in the present invention comprises incubation of the insulin in the solution for 10 hours.

The process of preparation of supramolecular protein assembly disclosed in the present invention comprises incubation of the protein in the solution for 6-192 hours.

The method for treatment using the pharmaceutical composition as disclosed in the present invention, wherein the composition is administered intramuscularly, intra-peritonealy or subcutaneously.

In still another embodiment, the present invention provides a composition comprising of the supramolecular insulin assembly (SIA) which is stable, protease resistant and has longer shelf life.

In still another embodiment, the present invention provides a composition comprising of the exendin-4 assembly (SEA) which is stable, protease resistant and has longer shelf life.

In still another embodiment, the present invention provides a composition comprising of the supramolecular insulin assembly (SIA) which is stable, protease resistance and has longer shelf life ranging from about 10 days to 150 days or more.

In still another embodiment, the present invention provides a composition comprising of the supramolecular exendin-4 assembly (SEA) which is stable, protease resistance and has longer shelf life ranging from about 10 days to 150 days or more.

As will be appreciated by those in the art a variety of the solutions such as known buffers can be used for re-suspension and washing of the supramolecular protein assembly disclosed in the present invention.

The term "therapeutically effective amount" as used herein refers to an amount of a therapeutic agent to treat, ameliorate, or prevent a desired disease or condition, or to exhibit a detectable therapeutic or preventative effect. The precise effective amount for a subject will depend upon the subject's size and health, the nature and extent of the condition, and the therapeutics or combination of therapeutics selected for administration. The effective amount for a given situation is determined by routine experimentation and is within the judgment of the clinician.

For purposes of the present invention, an effective dose of SIA will generally be from about 0.1 mg/kg to about 1.0 mg/kg, or about 0.2 mg/kg to about 2.0 mg/kg or about 0.5 mg/kg to about 3.0 mg/kg of the compositions of the present invention in the subject to which it is administered.

A pharmaceutical composition can also contain a pharmaceutically acceptable carrier. The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which can be administered without undue toxicity. Suitable carriers can be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art. Pharmaceutically acceptable carriers in therapeutic compositions can include liquids such as water, saline, glycerol and ethanol. Auxiliary substances, such as wetting or emulsifying agents, pH buffering substances, and the like, can also be present in such vehicles. Typically, the therapeutic compositions are prepared as injectables, either as liquid solutions or suspensions; solid forms suitable for solution in, or suspension in, liquid vehicles prior to injection can also be prepared. Liposomes and neosomes are included within the definition of a pharmaceutically acceptable carrier. Pharmaceutically acceptable salts can also be present in the pharmaceutical composition, e.g., mineral acid salts such as hydrochlorides, hydrobromides, phosphates, sulfates, and the like; and the salts of organic acids such as acetates, propionates, malonates, benzoates, and the like.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

The compositions disclosed in the present invention comprise supramolecular protein assemblies of the relevant/applicable therapeutic proteins and are applicable for treatment of a number of chronic diseases and acute symptoms.

The compositions disclosed in the present invention comprises oligomers of therapeutic proteins particularly the supramolecular assembly of a protein for sustained release of the protein.

Some widely-used biopharmaceuticals such as insulin, glucagon, and calcitonin can be induced to form amyloids. Compared to soluble precursor proteins, amorphous aggregates formed as a prelude to amyloid formation, gain new properties such as enhanced stability, protease resistance, self-propagation, longer shelf life, highly organized structure and can serve as a concentrated compact source of pure molecules.

The supramolecular insulin assemblies disclosed in the present invention exist with in a defined structure having both α-helical and β-sheet components. The adoption of the above mentioned unique structure results in a change in its solubility and its structure from the native insulin molecules in solution. Significantly, release of insulin monomers from this supramolecular structure are biologically active and thus resemble the native insulin structure. Novel dissolution properties are conferred upon this supramolecular structure formed, which acts as a prodrug, as by itself viz. In its prodrug form it was found that it has no action or effect on the signaling events or glucose homeostasis of the insulin sensitive fat cells. It is transformed into a drug by the release of insulin monomers from the depot or site of injection in vivo. Both in vitro and in vivo results demonstrate the uniqueness of the formulation to release bioactive insulin molecules showing an effect on the glucose homeostasis and other clinical parameters usually assessed for type I and II diabetes.

The present invention provides a composition comprising supramolecular insulin assembly useful in the treatment of diabetes mellitus. Supramolecular insulin is a hybrid of amorphous and nascent fibrillar oligomers of insulin and serves as a sustained release formulation for the release of bioactive insulin. The glucose regulatory hormone insulin is a 51 residue polypeptide that exists in equilibrium as a mixture of different oligomeric states, including hexamers, dimers and monomers, depending on the environment. In pancreatic secretory vesicles, insulin is stored as a hexamer at physiological pH, whereas it interacts with its receptor as a monomer. Under denaturing conditions, such as low pH or in the presence of strong denaturants, insulin aggregates to form amyloid fibrils (Paul Bevan Insulin signalling. J. Cell Sci., 114, 1429-1430 (2001)).

The supramolecular oligomers of insulin disclosed in the present invention is prepared at a pH ranging from 6.8 to 7.8 preferably 7.2.

The present invention provides a composition comprising supramolecular insulin assembly capable of sustained release of insulin monomers. The composition comprising a given supramolecular insulin assembly (viz SIA I, II, III or a combination thereof) is useful for achieving better glycemic control.

The present invention provides insulin oligomers, supramolecular insulin assembly II that is useful in achieving tighter glycemic control by achieving a sustained release of insulin. Supramolecular insulin assembly II when administered subcutaneously or intramuscularly maintains a basal level of insulin in STZ induced diabetic rat for a prolonged period ranging from about 10 days to 180 days or more, while simultaneously keeping a tight glycemic control, thus affording a long lasting treatment against diabetes mellitus.

According to the present invention, one embodiment provides a composition comprising supramolecular insulin assembly II that causes a sustained release of insulin monomers ranging between 0.5-1.5 ng/ml and lasts about at least 180 days when administered intramuscularly or subcutaneously.

Another embodiment of the present invention provides that the composition comprising supramolecular insulin assembly II wherein the amount of insulin monomer released from the supramolecular insulin assembly II is in the range of 0.5-1.5 ng/ml in serum.

In an embodiment of the present invention, the in-vivo effect of the composition comprising supramolecular oligomers of insulin on controlling blood glycemic levels have been verified using STZ induced diabetic rats.

Another embodiment of the present invention provides the dosage of the composition comprising supramolecular insulin assembly wherein the dosage ranging from about 50 μg to about 400 μg of insulin was monitored for the experimental time period.

Another embodiment of the present invention provides the dosage of the composition comprising supramolecular insulin assembly wherein the dosage is 200 μg of insulin.

Another embodiment of the present invention provides the dosage of the composition comprising supramolecular insulin assembly wherein the dosage is 100 μg of insulin.

In still another embodiment of the present invention provides a composition comprising the supramolecular insulin assembly, wherein the composition does not elicit insulin degrading enzyme activity (IDE) in and around the site of injection for a time period ranging from about 10 days to 180 days or more.

In yet another embodiment of the present invention, there is absence of anti-insulin antibodies in the serum of the subject for a time period of ranging from about 10 days to 150 days or more.

In still another embodiment, the present invention provides a composition comprising of the supramolecular insulin assembly which is stable, protease resistance and has longer shelf life ranging from about 10 days to 150 days or more.

In yet another embodiment of the present invention there is provided a composition comprising the supramolecular insulin assembly which is capable of releasing insulin monomers in a controlled manner for a long period of time without any burst of rapid release. The kinetics of transformation can be controlled both in vivo and in vitro.

Further, a composition comprising the supramolecular insulin assembly disclosed in the present invention can be used as a single dose having long lasting effect that frees the patients from the need to administer multiple doses of insulin every day.

The composition comprising the supramolecular insulin assembly disclosed in the present invention does not exhibit an abrupt large release of insulin thwarting hypoglycemic stage in diabetic subjects.

The composition comprising the supramolecular insulin assembly disclosed in the present invention is capable of releasing insulin monomers at a constant rate both in vitro and in vivo.

In still another embodiment of the present invention, the higher oligomeric stage of the supramolecular insulin assembly achieves a tightly regulated glycemic control without fasting hypoglycemia in diabetic subject.

In still another embodiment of the present invention, the higher oligomeric stage of the supramolecular insulin assembly achieves a tightly regulated glycemic control without fasting hypoglycemia in Type 1 diabetic subject.

In still another embodiment of the present invention, the higher oligomeric stage of the supramolecular insulin assembly achieves a tightly regulated glycemic control without fasting hypoglycemia in Type 2 diabetic subject.

In yet another embodiment of the present invention, there is no sudden increase of body weight of subjects when treated with the supramolecular insulin assembly or composition comprising supramolecular insulin assembly of the present invention.

In still another embodiment of the present invention, no lag phase is found in the release of bioactive insulin monomers from the supramolecular insulin assembly II in the Intraperitoneal Glucose Tolerance Test (IPGTT) blood glucose profile of the subject, similar to the administration of free insulin.

In yet another embodiment of the present invention, zero order kinetics or sustained release is observed for in vivo release of insulin monomers from the supramolecular insulin assembly II.

In still another embodiment of the present invention, insulin released from the supramolecular insulin assembly II is equivalent in biological function to soluble insulin.

Further, in another embodiment of the present invention, toxicity of the supramolecular insulin assembly is ruled out by performing biological assays for Serum glutamate oxaloacetate transaminase (SGOT), serum glutamate pyruvate transaminase (SGPT), total Bilirubin, Bilirubin, Alkaline Phosphatase, Serum total proteins, Serum Albumin, Serum Globulin, Serum A/G ratio, Kidney function test (KFT), Cataract Formation, Adipose Tissue weight, Body Weight and appearance.

In yet another embodiment, the rate of glucose infusion remains the same in treated animals. This concludes that the monomers released from the depot at the site of injection are biologically active and stimulate the muscles and the liver to take up glucose.

In still another embodiment, MTT assay was performed on MCF 7 cells to validate the unchanged structural and binding dynamics of the insulin monomers, released from SIA II.

Further, in another embodiment of the present invention, male Wistar rats were rendered diabetic using another chemical compound Alloxan. These diabetic rats were further treated with SIA II and showed similar result to that of STZ induced diabetic rat. A tight glycemic control was observed.

In still another embodiment of the present invention, C57BL/6 mice were made diabetic using streptozotocin, thereafter treated with SIA II, also showed normo-glycemic levels.

Another embodiment of the present invention is that the supramolecular insulin assembly is a stable depot useful for the controlled release of active peptide drugs from the supramolecular insulin assembly termini.

According to one embodiment of the present invention the supramolecular insulin assembly II is capable of affording a long lasting treatment against diabetes.

In another embodiment, the insulin used for preparation of supramolecular insulin assembly is preferably recombinant human insulin, bovine and pig insulin.

In still another embodiment, the composition comprising the supramolecular insulin assembly I and II (SIA I and II) or a combination thereof, disclosed in the present invention is capable of lowering blood glucose levels in animal subjects treated with streptozotocin to induce type II diabetes.

In still another embodiment, SIA I, which releases insulin monomers at a faster rate was administered to rats suffering from Diabetes Mellitus Type II (DM II).

According to one embodiment of the present invention, SIA II was also administered to DM II rats for the treatment.

In yet another embodiment, diabetic rats treated with both SIA I and II showed near normoglycemic levels bordering on the higher side, in both pre-prandial and post-prandial (180±15 mg/dl) states.

In yet another embodiment of the present invention, the dosage of SIA II injected was 150 µg in two places, both subcutaneously and intramuscularly.

Another embodiment of the present invention demonstrates the ability of SIA I and II to maintain near normoglycemic levels for up to 30 days.

In still another embodiment, administration of Exendin 4 along with insulin therapy was able to maintain near normoglycemic levels (135±10 mg/dl) for up to 45 days, and was a better formulation for treating DM II.

Further in another embodiment, SIA III, which releases insulin monomers but at a very slow rate (0.05-0.3 ng/ml) which can be useful in the treatment of borderline diabetic patients, viz prediabetic or subjects with poor prognosis in glucose tolerance tests, who require very little amount of insulin as a therapy.

In yet another embodiment of the present invention, the level of human insulin detected in the serum of diabetic rats is about 0.7-0.85 ng/ml.

In still another embodiment of the present invention, various serum parameters were estimated, such as triglycerides (TAG), free fatty acids (FFA), to demonstrate the effectiveness of the treatment.

In yet another embodiment, the level of TAG in the serum was in the range of 0.45-0.6 mmol/l for the Exendin 4 treated rats, which is almost same to the control.

Further in another embodiment, the FFA levels in the serum was estimated to be about 0.85-0.9 mmol/l for the Exendin 4a treated rats, which is almost same to the control.

In still another embodiment of the present invention, the increase in the body weight of the treated animals was almost same as that of control rats.

In yet another embodiment, the current methodology can be extended to those chronic and inflammatory diseases where a sustained and continuous therapy is required using peptides, proteins or small molecules.

Figure 1:
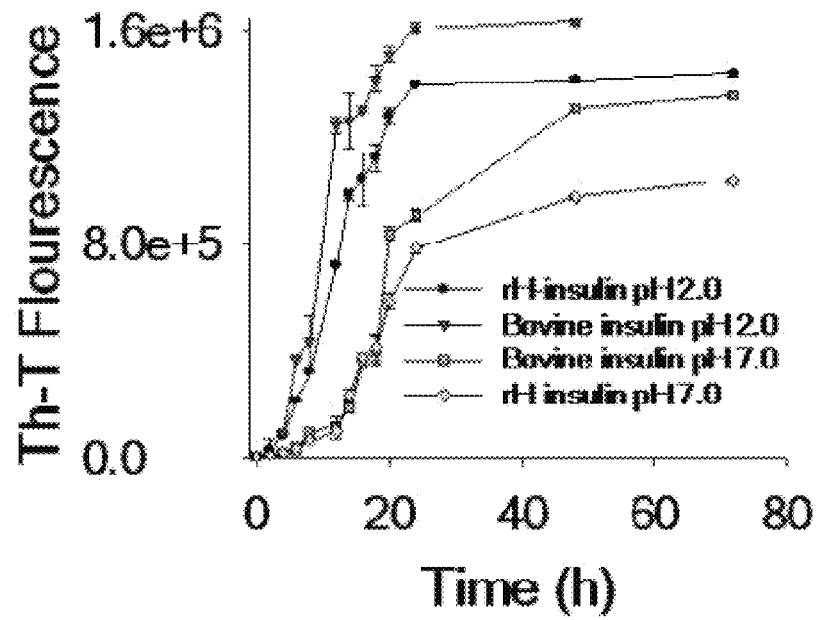
FIG. 1 is a line graph showing kinetics of fibril formation at pH 2.0 and 7.0 monitored with 50 μM Th-T fluorescence of recombinant human (rH) and bovine insulin.

Example 1 and 2 of the present invention provides a process for preparation of supramolecular insulin assembly II. The FIG. 1 provides details of the insulin (both human and bovine) fibril formation monitored by using Thioflavin T (Th-T) fluorescence (Le Vine, H. Quantification of β-Sheet Amyloid Fibril Structures with Thioflavin T. Methods Enzymol 309, 274-284 (1999)). Fibril formation by bovine insulin was noted by acquisition of Th-T fluorescence, when the insulin was agitated at 180 rpm at 37° C., both at pH 7.0 (50 mM PBS) and pH 2.0 (hydrochloric acid in water) (FIG. 1). The increase in Th-T fluorescence occurred due to its binding to insulin fibrils reaching a maximum value at 48 hrs for insulin incubated at pH 7.0, while at pH 2.0 the fibril formation is rapid and therefore, Th-T fluorescence attained a maximum value at 20 hr. FIG. 1 compares the fibril formation by both bovine and human insulin.

Figure 2A:
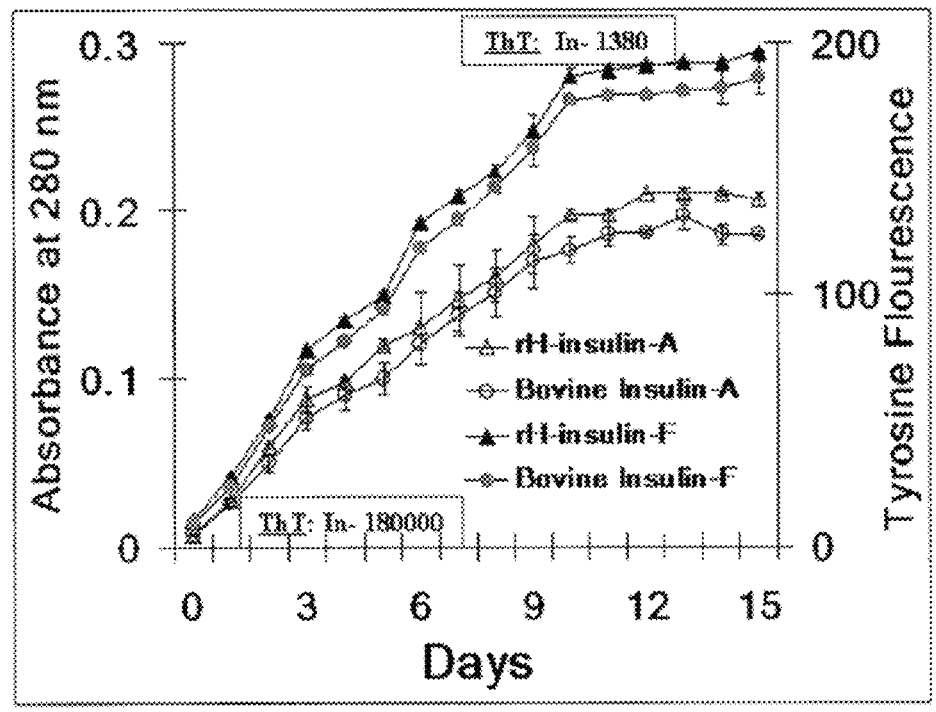
FIG. 2a is a line graph showing in-vitro release of insulin from supramolecular insulin assembly II (also referred to as pre-amyloid insulin II intermediate) of bovine and rH insulin monitored by absorbance at 280 nm and intrinsic tyrosine fluorescence. The Th-T intensity of solution inside the dialysis membrane at 0 h and 15 days is also given.
Figure 2B:
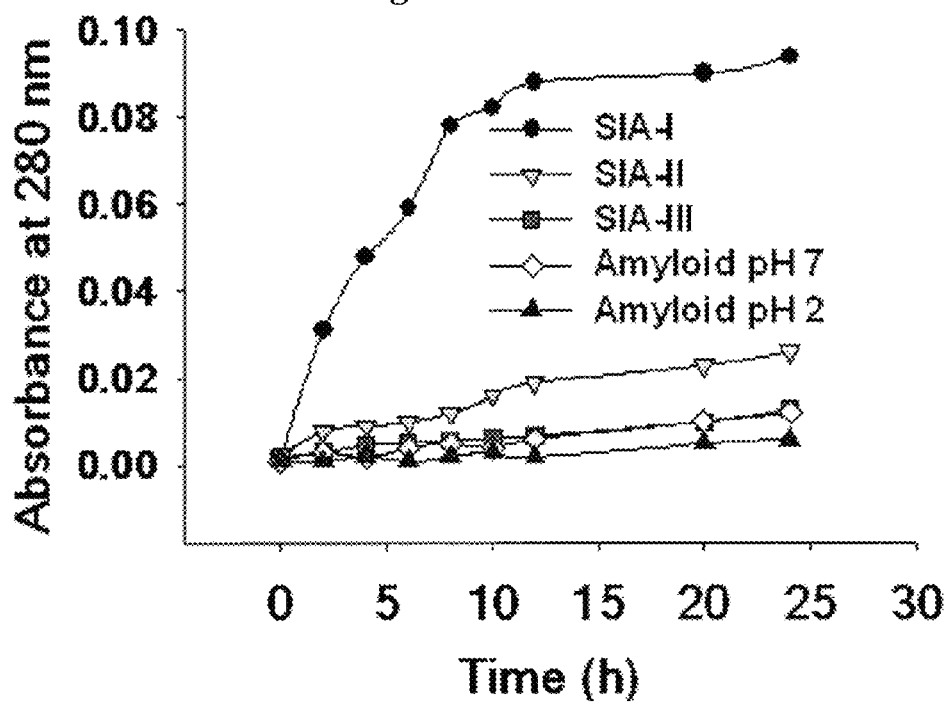
FIG. 2b is a line graph showing in vitro monomer release kinetics from the various supramolecular insulin assembly intermediates of bovine insulin.
Figure 2C:
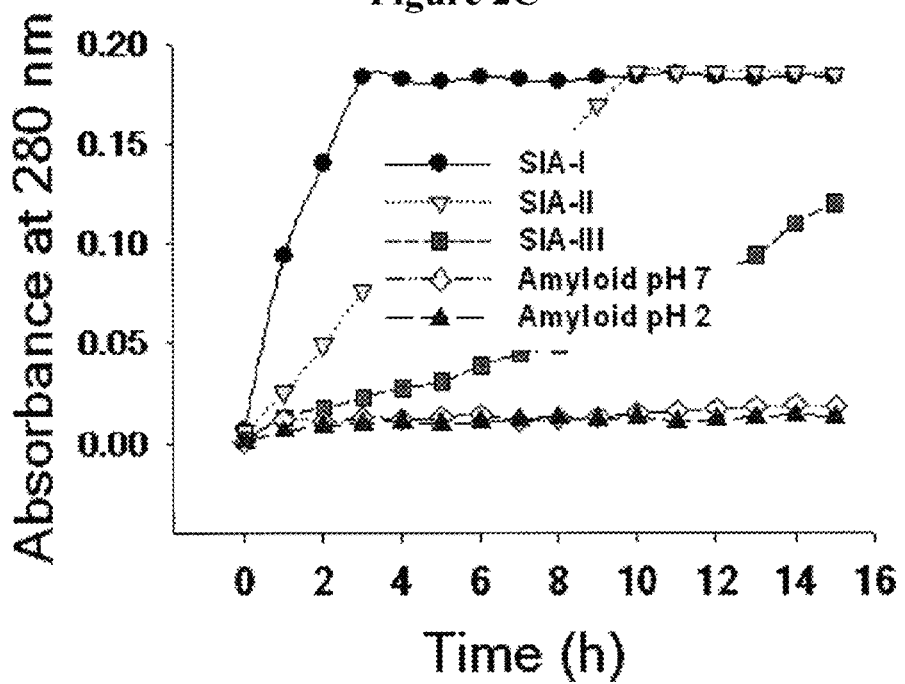
FIG. 2c is a line graph showing in vitro monomer release kinetics from the various supramolecular insulin assembly intermediates of rH-insulin.
Figure 2D:
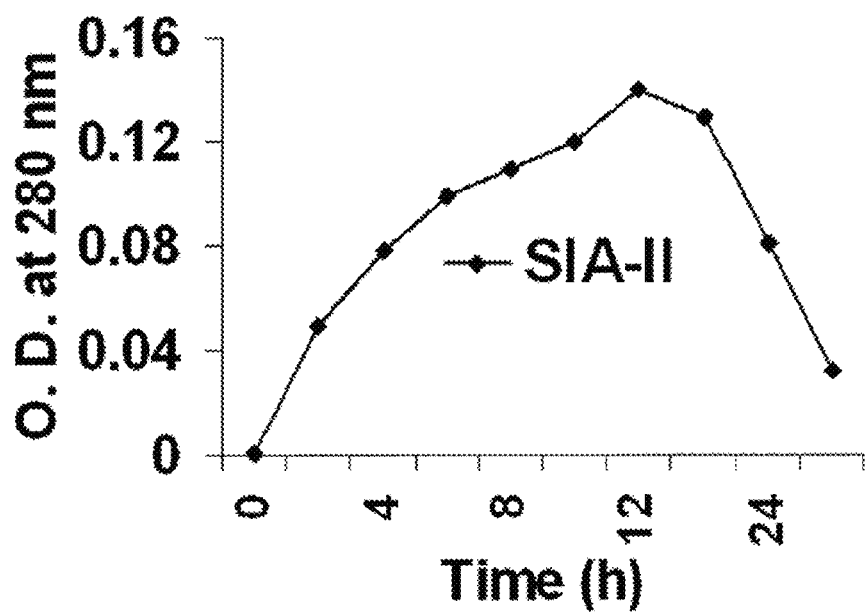
FIG. 2d is a line graph showing in vitro release kinetics of SIA II (alternatively preamyloid) formed at pH 7.0 monitored under constant 1 ml PBS solution.

Example 3 of the present invention provides kinetics of the release of insulin monomers from supramolecular insulin assembly-II. The supramolecular insulin assembly form of insulin acts as a reservoir for the sustained release of insulin monomer for a long time (FIG. 2a). The release of insulin monomers from its amyloid and various supramolecular assemblies of insulin were noted and is depicted by FIG. 2b & c. The fully formed amyloid fibers release negligible insulin irrespective of pH. At pH 2.0, supramolecular insulin assembly intermediates, particularly, supramolecular insulin assembly II, release insulin at a very slow rate suggesting that these oligomers are sturdy and tightly associated. However, the pH 7.0 intermediate (termed supramolecular insulin assembly II), exhibiting a turbidity of 0.9-1.3 at 600 nm, release insulin at an appreciable rate. A linear increase in the release of insulin monomers at 280 nm absorbance over a period of 15±5 days is observed. When insulin release from SIA was observed under constant volume of 1 ml, a bell shaped curve was observed (FIG. 2d). This demonstrates the reversibility of the oligomer formation procedure and the existence of equilibrium between free insulin and SIA. The tyrosine fluorescence of the released sample corroborated these observations as is provided in FIG. 2a. The insulin amyloid intermediate, supramolecular insulin assembly II (alternatively called insulin pre-amyloid II) meets the requirement of a sustained release of 2-4 μM (0.4-0.6 IU) of insulin monomers per hour in vitro, thereby achieving a constant yet slow release in vivo for maintaining basal insulin levels in the body.

Figure 3:
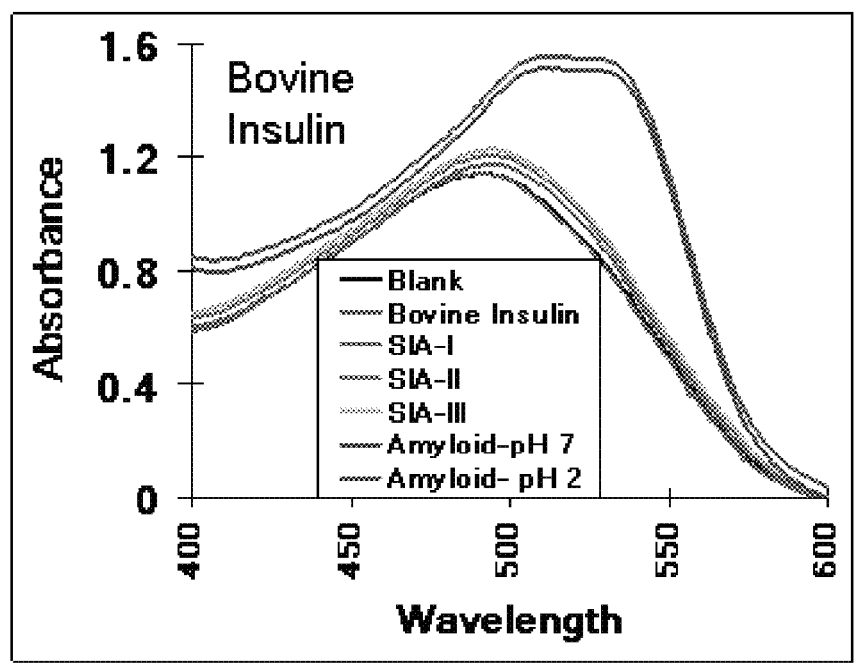
FIG. 3 is a line graph showing Congo-Red binding studies with native insulin, supramolecular insulin assembly II (alternatively pre-amyloid insulin II), supramolecular insulin assembly III (alternatively pre-amyloid insulin III) and insulin amyloid (bovine and human).
Figure 3:
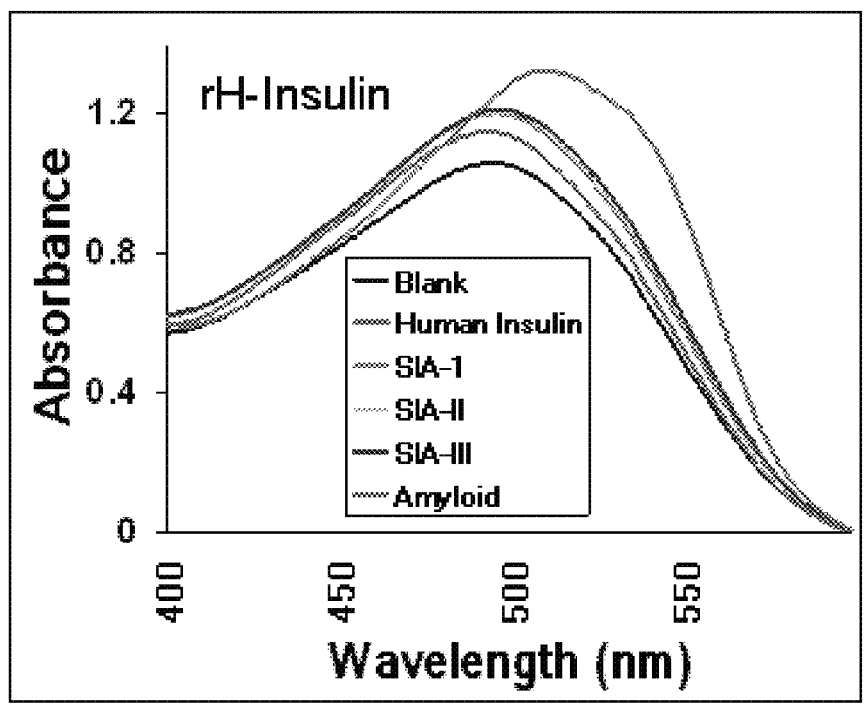

Example 4 provides characterization of supramolecular insulin assembly using Congo-Red (CR) binding (Klunk, W. E., Jacob, R. F. & Mason, R. P. Quantifying amyloid by Congo red spectral shift assay. Methods Enzymol 309, 285-305 (1999)). Like Th-T, CR also binds specifically to the β-sheet rich structures of amyloid and has been used routinely for their detection. CR binding to samples incubated with 50 μM CR in PBS for 1 h at 37° C. was monitored by the red shift in its absorption maximum by scanning 400-600 nm regions. FIG. 3 provides that the supramolecular insulin assembly (rH and bovine) exhibits weak binding to CR, whereas fully grown fibers at pH 2.0 and 7.0 showed significant binding.

Figure 4:
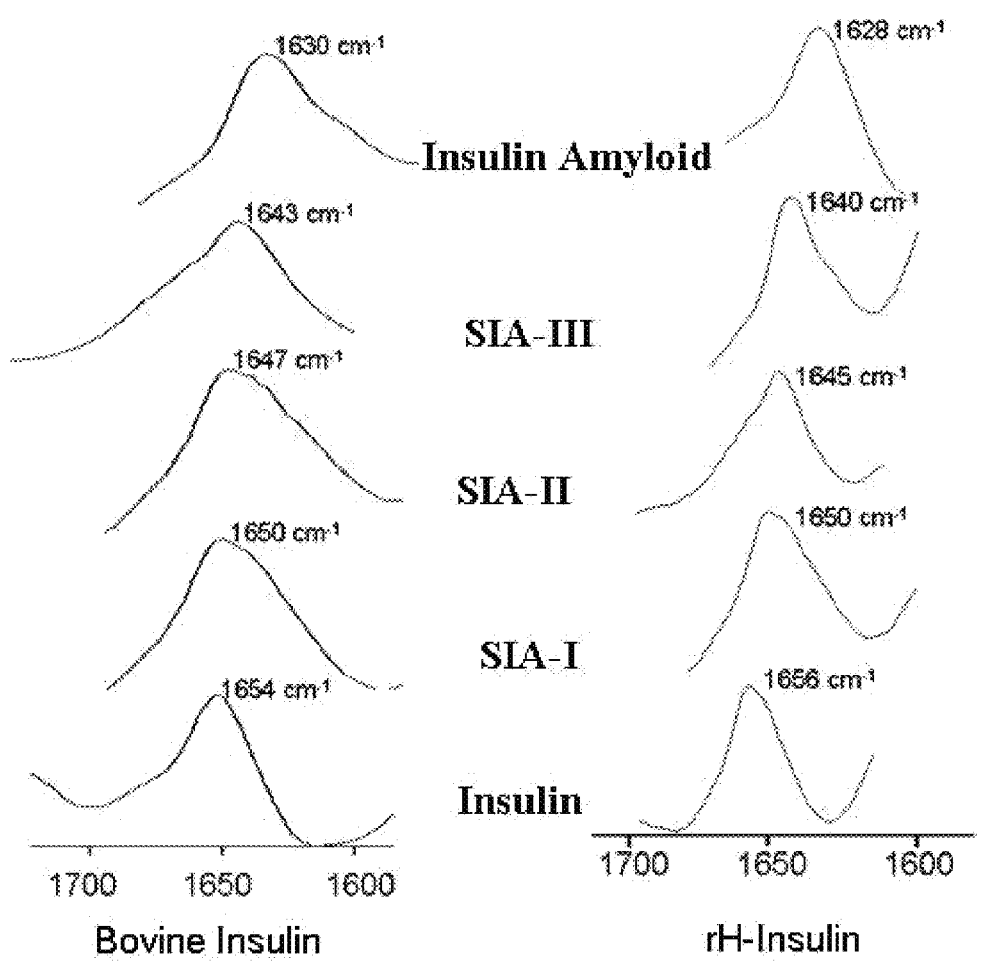
FIG. 4 is a line graph showing fourier transform infrared (FTIR) spectroscopic characterization of r-human and bovine insulin.

Example 5 provides tyrosine fluorescence study. Example 6 provides Fourier Transform infrared spectroscopy study. Supramolecular insulin assembly I, II and III were also characterized using ATR-FTIR. Distinct spectra corresponding to each stage was observed (FIG. 4). A shift of the IR band towards lower frequencies is observed. Supramolecular insulin assembly II has a sharp peak at 1647-1645 $cm^{-1}$, while the fully formed insulin fibril (amyloid) has a peak at 1630-1628 $cm^{-1}$ for bovine and rH insulin respectively. The FTIR spectra of Supramolecular insulin assembly II is in good agreement with the CR data showing that the protein is still largely helical, albeit with an increase in the content of random coil structure.

Figure 5:
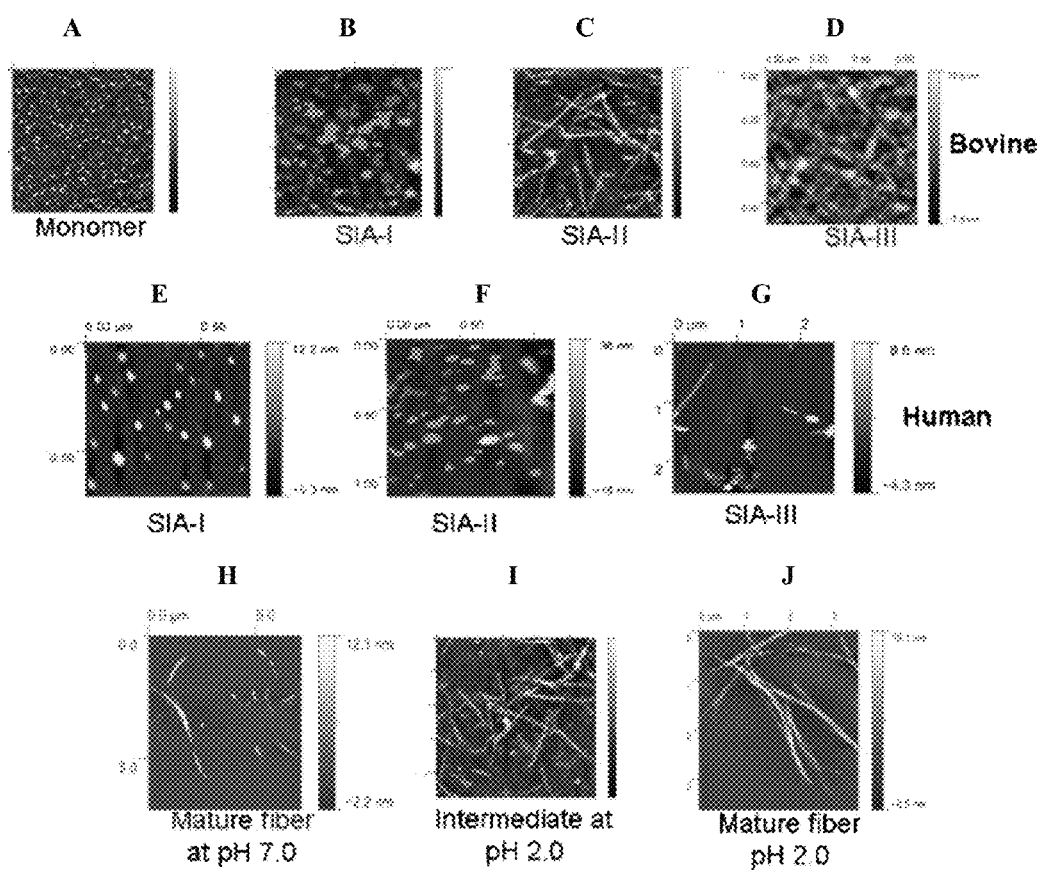
FIG. 5 is a series of photographs showing morphologies of supramolecular insulin assembly (alternatively pre-amyloid insulin) intermediates and insulin fibrils studied by Atomic Force Microscopy (AFM)

Morphology of fibers formed at pH 2.0 and 7.0 were assessed by Atomic Force Microscopy (AFM) and Transmission Electron Microscopy (TEM) as provided in Example 7 and 8 respectively. Native insulin molecules (both bovine and rH) at pH 7.0 and pH 2.0 show random distribution with a height of 1.3±0.21 nm, which correlates with the dimension of insulin monomers (1.11 nm) and dimers (1.49 nm) (FIG. 5(a)). Intermediates of the fibrilization process at pH 7.0 are shown in FIG. 5(b-d) for bovine insulin and FIG. 5(e-g) for rH insulin. SIA-I represent elongated clusters having a pearl-like arrangement. In between, there are some elongated linear particles with 12±2 nm heights, suggesting further association into higher oligomeric states. The SIA-II intermediate is seen as a linear association of the above mentioned elongated clusters in case of both bovine and rH insulin, having a unique entity with a supra-oligomeric structural organization. SIA-III (fibril stage succeeding SIA-II) showed an increase in density of higher oligomeric structures. Fully grown fibers at pH 7.0 represent the typical cross β structure of insulin amyloid (FIG. 5(vii)). Intermediates of pH 2.0 fibrilization process at 6-7 h reveal a lateral association of two fibrils of height 7.2-8.3 nm, and after 20 h, large twisted fibers of 10-12 nm width were observed (FIGS. 5i and 5j).

Figure 6:
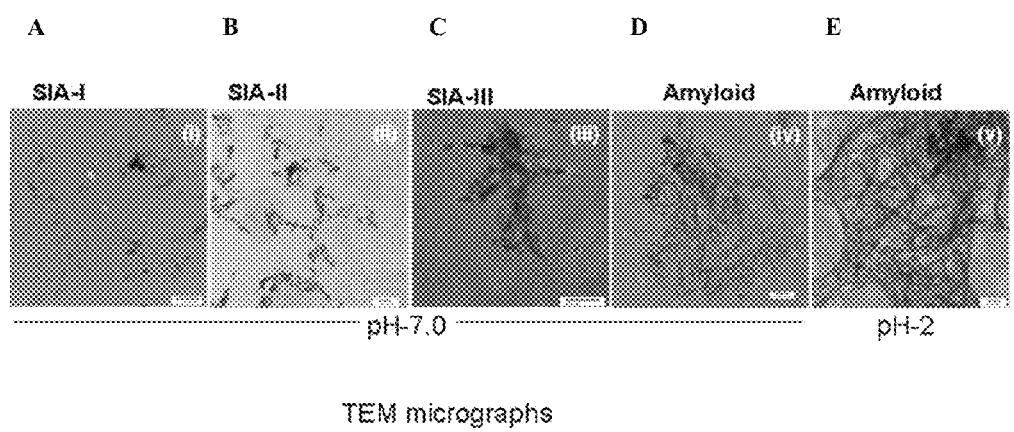
FIG. 6a-e is a series of photographs showing negative staining TEM micrographs of insulin fibrils and the intermediates during the formation of supramolecular insulin assembly (a) Supramolecular insulin assembly I (alternatively pre-amyloid insulin I), pH 7.0,
(b) Supramolecular insulin assembly II (alternatively pre-amyloid insulin II), pH 7.0,
(c) Supramolecular insulin assembly III (alternatively pre-amyloid insulin III), pH 7.0,
(d) Mature fibers at pH 7.0,
(e) Fiber formed at pH 2.0, 37° C.

Example 8 provides Transmission Electron Microscopy (TEM) to assess the presence of the possible assemblies of insulin. TEM micrographs shows the presence of some amorphous and higher oligomeric structures in the supramolecular insulin assembly II stage (FIG. 6a). The stages after supramolecular insulin assembly II (FIG. 6b) have more fibrillar structure as shown in (FIG. 6 c & d)). In contrast, there is an abundance of fibrillar forms when insulin was incubated at pH 2.0 (FIG. 6 e).

Figure 7A:
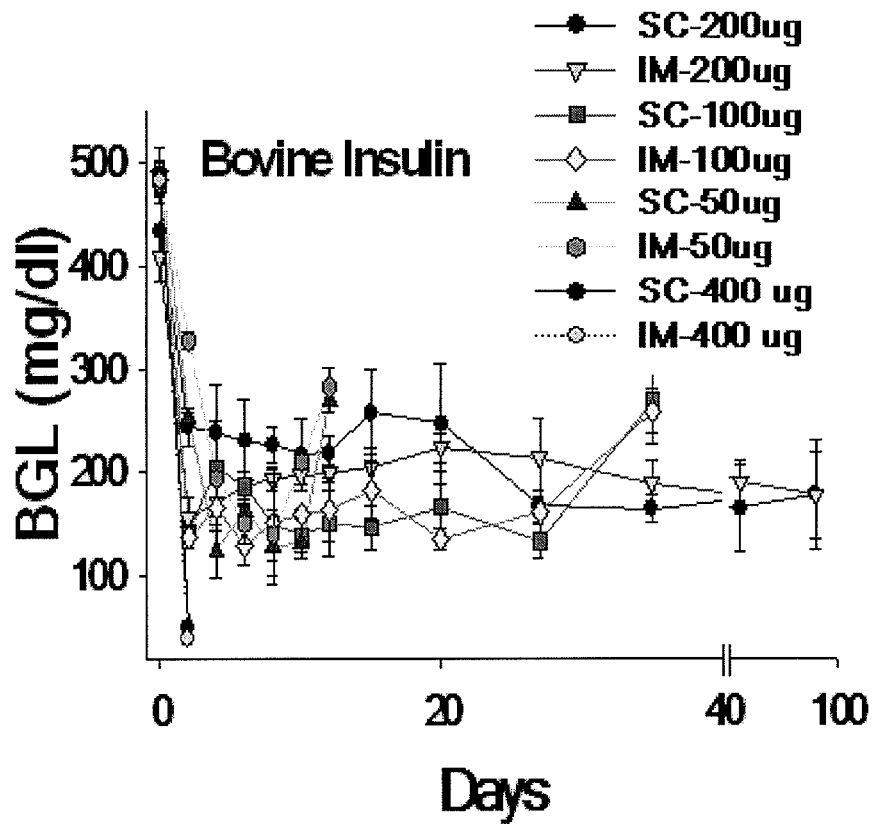
FIGS. 7a-b, are line graphs showing in vivo efficacy of supramolecular insulin assembly (alternatively pre-amyloid insulin) in glucose homeostasis.

Example 9 provides details of the animal models used for studying the effectiveness of insulin amyloid and supramolecular insulin assembly forms. The authors have used four different diabetes models for testing the hypothesis and the therapeutic potential of SIA, in the treatment of diabetes, namely, (a) STZ treated rats, (b) Alloxan treated rats and (c) STZ treated mice (d) STZ rabbit To standardize the dosage, 50 μg, 100 μg, 200 μg and 400 μg of supramolecular insulin assembly-II was injected subcutaneously and alternatively intramuscularly in diabetic rats. As summarized in FIG. 7a&b, a single dose of 50 and 100 μg of supramolecular insulin assembly maintained near-normoglycemic levels up to only 10 and 30 days respectively, compared to 135 and 160 days when 200 μg supramolecular insulin assembly, both bovine and human respectively was used. In case of 400 μg dosage, sudden non-fasting normoglycemia and fasting hypoglycemia was observed irrespective of the route used, suggesting release of an initial bolus of a basal level of insulin monomer from the SIA depot of bovine insulin. The usage of 200 μg of supramolecular insulin assembly as a therapeutic dosage was chosen for the detailed long term prospective studies.

Example 10 provides the treatment of the diabetic animals with supramolecular insulin assembly form of insulin. The STZ-induced diabetic rats assigned to multiple groups were treated with insulin (4 IU/kg, IP), supramolecular insulin assembly (200 μg both SC and IM), respectively, to study the in vivo effect of the supramolecular insulin assembly therapy on controlling blood glycemic levels. In addition, one group of PBS treated diabetic rats and another group of normal rats served as diabetic and non-diabetic control. The pre-prandial and post-prandial blood glucose levels of the rats were monitored for a period till the physiological effect of insulin was observed. As shown in FIG. 8a&b, treatment with 200 μg of supramolecular insulin assembly maintained the basal level of insulin by the sustained and slow release of insulin monomers from supramolecular insulin assembly depot in STZ-induced diabetic rats, leading to a significant reduction in the non-fasting blood glucose levels without fasting hypoglycemia (FIG. 9a&b). No significant difference was observed whether supramolecular insulin assembly was injected via subcutaneous or intramuscular route. In the case of free insulin (viz. in its normal counterpart; non-supramolecularly organized form) treatment (single dose of 4 IU/kg), daily blood glucose was reduced to a non-fasting value of 350-450 mg/dl and fasting 300-400 mg/dl only. Diabetic rats were given insulin intraperitoneally everyday maintained hyperglycemic blood glucose levels (300±100 mg/dl). In contrast to free insulin treatment, where daily dose was required to keep blood glucose from plummeting to very high levels, single injection of supramolecular insulin assembly was sufficient for achieving near-normoglycemia levels (150±60 mg/dl) in diabetic rat for 3 months without fasting hypoglycemia (90±50 mg/dl). Similar results were obtained with supramolecular insulin assembly formed from human insulin, as depicted in FIGS. 8b&9b. Administration of insulin amyloid, formed at pH 7.0 and 2.0, had no beneficial effect on the glycemic status of diabetic rats, as evident from FIG. 10.

Again the body weight which is an indicator of normal health was monitored along with BGL in all cases over the entire period of treatment. As shown in FIG. 11, there was an initial loss of body weight immediately after STZ treatment, but progressive weight gains were achieved in diabetic rat after treatment with supramolecular insulin assembly II and the curve of supramolecular insulin assembly treated animals paralleled that of non-diabetic control. Thus, the surprising efficacy of supramolecular insulin assembly II for use in long term treatment of diabetes mellitus is considered an improvement over the conventional methods.

Example 11 provides intraperitoneal glucose tolerance test to assess the efficacy of supramolecular insulin assembly to release insulin in a continuous manner. The in vivo release of insulin was monitored. The biological activity of the released monomer was estimated by blood glucose disposal from the blood. The details of the independent experiments performed are shown in FIG. 12. The glucose levels were determined before (TO) and 30, 90, 150, 270 and 330 min after glucose administration to fasting normal and STZ treated rats, upon treatment with PBS, supramolecular insulin assembly II and insulin. As shown in FIG. 12, insulin injection, supramolecular insulin assembly II treatment or in vitro released monomers alone significantly improved the glucose tolerance test in treated animals, and their elevated blood glucose levels after the glucose infusion returned to the pre challenged levels within 1.5 hrs.

Example 12 describes serum insulin quantification of bovine and rH insulin on administering supramolecular insulin assembly (FIG. 13 $a$). Serum insulin was detectable up to a period of 150 and 180 days for bovine and rH insuline SIA-II, respectively, which corresponded to a decrease in BGL. The decrease in blood glucose levels was sustained up to a period of 150 and 180 days for bovine and rH insuline SIA-II, respectively, maintaining near normal glucose values for more than 20-25 weeks with a single dose of the supramolecular insulin assembly II. Solid state ELISA was performed to quantify the plasma levels of insulin released from the insulin SIA II, which is responsible for the maintenance of normal blood glucose values. As expected, basal or slightly above basal level insulin release was achieved in case of supramolecular insulin assembly treated diabetic rats (0.5-1.2 ng/ml) compared to non-detectable insulin level (0.08 ng/ml) in PBS treated diabetic rats (FIG. 13 $a\&c$). A sustained release of insulin (0.8-1.1 ng/ml) was observed from the day of injection up to 150-180 days irrespective of the route, which contributed to near-normoglycemic values in the supramolecular insulin assembly treated animals. While some variation was seen from animal to animal, remarkable values of insulin release could be achieved ranging from 0.5-1.2 ng/ml. This basal level was enough to maintain normo-glycemic levels up until the exhaustion of the supramolecular insulin assembly. However, in insulin treated diabetic animals, a relatively higher mean serum level was detected, but with high degree of variation between animals. This was attributable to inter-subject variability in BGL by insulin treatment alone. Serum insulin levels were also quantified for the glucose tolerance test performed, for which glucose data has already been shown. FIG. 13$b$, describes the bovine insulin values in the serum of rats up to 270 min in IPGTT experiments. In case of both control and STZ treated rats given PBS only, the bovine insulin value is almost negligible (FIG. 13$b$). Whereas, in case of insulin administration, the insulin values increases to ~0.9 ng/ml in 30 min, and then decreases over a period of time. Similar profile was observed when terminally released insulin which is equivalent to free insulin was used. This corresponds to the decrease in blood glucose levels, followed by its increase due to uptake and degradation of insulin. On the other hand, in supramolecular insulin assembly treatment, insulin levels in serum reached to 0.8-0.9 ng/ml, equivalent to the basal level in 30 min and then remained constant over the period of study, as seen by bovine insulin quantification. This sustained basal level ensures a normo-glycemic level, instead of decreasing the levels drastically and making the animal hypoglycemic. Further, Rat insulin ELISA was performed to evaluate the serum insulin levels for both control rats and STZ treated ones. As shown in FIG. 13$c$, rat basal insulin levels is 0.501 ng/ml and increases manifold in response to infused glucose. In case of STZ treated rats, basal insulin levels are almost negligible, due to the destruction of the pancreatic β cells by STZ. This confirms that the decrease in blood glucose levels seen in case of supramolecular insulin assembly treatment is due to the release of bovine/rH insulin released from the SIA II. In the process of preparation of insulin SIA II, insulin other than bovine and rH insulin selected from a group consisting of but not limited to pig insulin is employed.

Example 13 provides I125 labeling of insulin to validate and quantify the in vitro release from the termini of SIA II. Supramolecular insulin assembly II formed from labeled insulin has a specific activity of 49912 CPM/ml/μg. 50 μl of supramolecular insulin assembly (4991200 CPM) was injected subcutaneously as well as intramuscularly and blood glucose levels were monitored and serum samples were collected at 0, 30 min, 1 h, 4 h, 10 h, 24 hrs, thereafter once a day, and then on alternate days or once in a week. Counts in per ml of serum were measured (FIG. 14$a$). As shown, blood glucose profile was same as observed with unlabeled SIA II. The CPM/ml calculated remained almost constant (FIG. 14$a$) when plotted against number of days of treatment. However there was an initial high count at 30 min-4 hrs, which then gradually decreased to constant level of 2000-3000 in 10 hrs. The amount of insulin released in blood was calculated and was in the range of 0.5-1.2 ng/ml which corresponds to the basal or slightly above basal level of insulin in the serum as observed with ELISA (FIG. 14$b$). To further prove that released insulin from supramolecular insulin assembly is monomeric, serum of different time points were resolved on tricine-SDS-PAGE and radiogram was developed using the phosphor imager. As shown in FIG. 15, the band in serum corresponds to free insulin monomer and its intensity remained constant for a long period when equal amount of serum was loaded. A decrease in intensity was observed after 20 days showing usage and depletion of the supramolecular insulin assembly depot over a period of time together with some effect of the decay of the radio-label itself.

Example 14 describes hyperglycemic clamp studies performed to assess the slow and continuous release of insulin monomers from the injected SIA II. At one week, one month and three month time interval, the rate of glucose infused for maintaining hyperglycemic state remained unchanged during the course of the experiment. This shows that there is constant insulin release from the depot at the site of injection. In case of the group being administered free insulin, the amount of glucose infused decreases over time, which is due to a decrease in the uptake of blood glucose by muscle and liver in the absence of continuous supply of free insulin (FIG. 16 $a$-$c$).

Example 15 provides the effect of insulin on glucose transport and other metabolic events in adipose tissues by performing primary culture of rat adiposites that are mediated by intracellular signaling cascades which start after insulin binds to insulin receptors on cell surface (Paul Bevan Insulin signalling. J. Cell Sci., 114, 1429-1430 (2001)). The effect of insulin in the cell is mediated by the activation of intracellular mediators like PI3K, AKT and ERK. Activation of the PI3 kinase and Akt, mediates insulin induced glucose uptake and GLUT-4 vesicle translocation to the plasma membrane and is involved in various other insulin effects including inhibition of lipolysis and activation of fatty acid, glycogen, protein and DNA synthesis. On the other hand, activation of the extracellular signal-regulated kinase (ERK) pathway is implicated in mitogenic responses of pre-adipocytes to growth factors. The level of PI3K which is the first kinase downstream to insulin signaling was studied. As shown in FIG. 17a, the level of PI3K is augmented significantly when supramolecular insulin assembly and insulin released in vitro from them is used compared to control. There was no significant difference observed compared to insulin. The total protein and activated level of Akt, a threonine/serine kinase important for regulation of insulin action and its various metabolic responses in adipocytes was also assessed. A significant increase in p-Akt level was observed which was again similar to the response observed with free insulin. There was no difference in total Akt protein level hence, no difference in its expression in the presence of insulin or its supramolecular insulin assembly II was observed. To assess whether the observed temporal profiles and level of Akt phosphorylation in adipocytes was parallel to the difference in Akt activity, the phosphorylation of the endogenous Akt substrate GSK3β was monitored by immunoblotting using antibodies to GSK3β and p-GSK3 β. GSK3β is directly phosphorylated by Akt on ser-21 and is inactivated following its phosphorylation. The phosphorylation of GSK3β increased several fold in adipocytes treated with either free insulin or supramolecular insulin assembly II compared to control and there was no significant difference among the treated cells. No difference was observed in total GSK3β protein level suggesting no change in its expression subsequent to treatment. Therefore, both Akt and GSK3β showed rapid and pronounced responses to supramolecular insulin assembly II and released insulin from supramolecular insulin assembly and were similar to responses observed in stimulation with free insulin used as a control. The activation of ERK in treatment with supramolecular insulin assembly and insulin released from it in adipocytes was observed, as this kinase is involved in insulin-mediated regulation of adipocytes transcription factors and adipose tissue development. On treatment of adipocytes with insulin, supramolecular insulin assembly and released insulin from supramolecular insulin assembly, a significant activation of ERK 1/2 was observed compared to control. The phosphorylation of ERK 2 was two fold higher than ERK 1 suggesting more expression of ERK 2 on treatment. There were no significant difference in phosphorylation pattern of ERK 1/2 in SIA, insulin or serum treated cells. Therefore the ERK phosphorylation in supramolecular insulin assembly II and insulin treated cells were similar in the context of PI3K, Akt and GSK3β mediated signaling. Similar activation of signaling mediators was observed, when serum from insulin or its SIA-II treated animals was added to cultured adipocytes (FIG. 17b). Together these data demonstrate that insulin released from supramolecular insulin assembly II is able to activate the insulin signaling pathway in adipocytes as insulin itself. The effects observed are even better as insulin in its monomeric form is released predominantly from its supramolecular insulin assembly.

Example 16 describes Western blot analyses of insulin, supramolecular insulin assembly and in vitro released insulin (monomers) and serum from rats treated with insulin, supramolecular insulin assembly and PBS.

Example 17 describes histology and immunohistochemistry details of supramolecular insulin assembly of insulin. The diabetic rats treated with supramolecular insulin assembly were monitored for the presence of residual amount of supramolecular insulin assembly from the day of injection from one week to 12 weeks. Supramolecular insulin assembly deposits in subcutaneous as well as muscle tissues were detected using Congo red. Subcutaneous and muscle tissue sections were prepared, stained and analyzed as described in materials and methods. Tissues obtained after 24 h of supramolecular insulin assembly injection were found to bind with Congo red effectively, confirming the presence of higher amounts of supramolecular insulin assembly fibrils (FIG. 18). Congo red binding decreased in a time dependent manner and was negligible after 16 weeks (FIG. 18 a(i-x) &b(i-x)), confirming the release of insulin from the termini of supramolecular insulin assembly deposits. Same tissues were also checked for inflammation caused by supramolecular insulin assembly by H & E and immunostaining. Representative slides were subjected to H&E staining method and immunohistochemistry for the presence of inflammatory cells (FIGS. 18a (xi-xx) and 18b (xi-xv)).

As compared to the sections from LPS injected rats, where infiltration of proinflammatory cells were visible in both subcutaneous and muscle tissues stained with H &E (FIG. 19a (i-ii)), supramolecular insulin assembly injected sections did not show any sign of inflammation even after 16 weeks (FIG. 18a(xi-xv)). Similar results were observed in the case of immunostained slides where LPS from *Escherichia coli* was sufficient to attract huge number of proinflammatory cells after 72 h at the site of injection (FIG. 19a (iii-iv)) whereas no such reaction was observed in animals treated with supramolecular insulin assembly (FIG. 18a (xv-xx) and b(xi-xv)). These observations reinforce non-cytotoxic nature of the supramolecular insulin assembly being used. Amyloid formed at pH 2.0 binds congo red dye very efficiently as seen in FIG. 19b, when injected subcutaneously. Moreover there is no decrease in the depot corroborating the data that no release of insulin monomers takes place from the fully formed amyloid (FIG. 19b i-viii).

Example 18 describes alloxan model of diabetes. Male wistar rats were rendered diabetic using alloxan and their blood glucose levels were monitored. Administration of supramolecular insulin assembly II to diabetic rats, lowered the blood glucose level to near normoglycemic levels, and maintained a tight glycemic control for up to >120 days, in both pre-prandial and post-prandial conditions (FIG. 20a&b). Serum insulin quantification was done using ELISA. From the day of injection, a sustained and constant release of human insulin is observed in the serum of the treated rats (0.5-0.9 ng/ml) (FIG. 20c). Thus the physiologic effect seen by the lowering of the glucose levels in diabetic rat is due to the continuous release of insulin monomers from the SIA-II depot formed at the site of injection.

Example 19 Reduction of secondary complications related to hyperglycemia in type I diabetes: In type-1 diabetes, insufficient supply of insulin leads to increased protein degradation in skeletal muscles and lipolysis in adipocytes. Diabetic rats showed a marked decrease in skeletal muscle (~20-40%) and abdominal fat (>60%) (Nathan, D. M., Cleary, P. A., Backlund, J. Y., et al. Intensive diabetes treatment and cardiovascular disease in patients with type 1 diabetes. N. Engl. J. Med. 353, 2643-53 (2005)). In contrast, supramolecular insulin assembly treated diabetic animals had normal weight for these tissues and were healthy. Development of cataract in diabetic rats as well as in insulin treated ones were observed (FIG. 21). While no cataract formation was observed in animals treated with SIA II, majority of untreated rats exhibited cataract as demonstrated in FIG. 21. Furthermore, the function of liver and kidney, the two main organs of the body which typically and severely get afflicted in diabetes were normal in supramolecular insulin assembly II treated rats as compared to their untreated or free insulin infused rats and is summarized in Table 1.

Heart, kidney and liver sections were examined for the deposition of higher oligomers of SIA-II injected to diabetic rats after 12 weeks, visualized using congo red dye (FIG. 22). No deposition of oligomers was observed in any of the tissue sections.

Example 20 provides the details of detection of insulin degrading enzyme (IDE) and screening of antibodies against insulin. Subcutaneous resistance to insulin in Type-1 diabetes is a rare syndrome (Paulsen, E. P., Courtney, J. W. & Duckworth, W. C. Insulin resistance caused by massive degradation of subcutaneous insulin. Diabetes 28, 640-645 (1979) and Freidenberg, G. R., White, N., Cataland, S., O'Dorisio, T. M., Sotos, J. F. & Santiago, J. V. Diabetes responsive to intravenous but not subcutaneous insulin: effectiveness of aprotinin, N. Engl. J. Med. 305, 363-368 (1981)), defined as the lack of biological activity of subcutaneously injected insulin; nevertheless, efficacy for intravenously infused insulin is retained. This is mainly attributed to increased insulin degradation by IDE in the subcutaneous tissues. IDE degrades insulin specifically (Duckworth, W. C., Bennett, R. G. & Hamel, F. G. Insulin degradation: progress and potential, Endocr. Rev. 19, 608-624 (1998)) and the partially degraded insulin is reabsorbed into the circulation with increased immunogenicity but no biological activity. IDE is present in insulin responsive tissues and in insulin insensitive cells such as monocytes and lymphocytes. To check the development of such a resistance in supramolecular insulin assembly treated animals, biological activity of IDE and the presence of anti-insulin antibody were determined as described in methods section. IDE activity was negligible in all the serum samples (1-12 weeks) from supramolecular insulin assembly treated animals (FIG. 23). Similarly there was no presence of anti-insulin antibodies even after 12 weeks of treatment, supporting the absence of IDE activity (FIG. 24).

To see whether the insulin monomers released from supramolecular insulin assembly II had undergone any change in its structure or its binding dynamics, MTT assay on MCF 7 cell lines was performed. The proliferation of MCF 7 cells, when SIA was added to the culture was similar to that of those cells to which native insulin was added. Furthermore, the released monomers from the SIA II formed, also showed the same kinetics of cell proliferation. Insulin like growth factor I was used as a positive control for the proliferation of MCF 7 cells (FIG. 25). Insulin and IGF 1 have similar structure, and in the absence of the other, each can bind to the other receptor. But whereas IGF 1 is mitogenic, insulin upon binding to insulin receptor or IGF receptor does not cause proliferation of cells. Thus the monomers released from SIA II have the same binding kinetics as that of native insulin, and do not undergo any structural change.

Example 21 describes Streptozotocin model for induction of diabetes in mice. Dose response for human and bovine SIA in mice rendered diabetic using STZ. The administration of various dosage 20, 50, 100 and 200 μg of respective SIA to diabetic mice maintained the normo/near-normo glycemia for 5, 15, 30, 120 days respectively (FIG. 26 a-c).

Example 22 describes Streptozotocin model for induction of diabetes in rabbit. The administration of 1 mg/kg body weight of rH-insulin SIA-II to diabetic rabbit maintained the normo/near-normo glycemia for atlest 80 days (FIG. 27).

Example 23 provides details of the experiments carried out with supramolecular insulin assembly along with Exendin 4. For treatment of type II diabetes, supramolecular insulin assembly or exendin 4 was administered. The therapy administered was able to lower blood glucose levels and maintain at near normoglycemic levels in diabetic rats up to >30 days (FIG. 28). The levels of TAGs and FFA also remained near about normal as compared to only insulin or PBS treated rats, where the levels increased up to 1.5 fold in the serum as shown in Table 2.

The supramolecular insulin assembly formulation of the present invention shows surprising result of release of insulin monomers for a long period. Further, the supramolecular insulin assembly II of the present invention does not exhibit an abrupt large release of insulin; thwarting hypoglycemic stage in STZ treated diabetic rats. To validate the above unexpected result the intermediates of insulin supramolecular assembly II obtained during insulin fibrilization process at pH 7.0 was assessed. The intermediate supramolecular insulin assembly II is found to release insulin monomers at a constant rate for long duration. The intermediate (supramolecular insulin assembly II) selected does not show significant Congo-red binding indicating its failure to progress to an amyloid state and AFM analysis confirmed the presence of a linear association of elongated oligomers as the predominant species. The height of this unique entity is 18±5 nm compared to highly twisted fully grown fiber with height 12±5 nm suggesting that the elongated oligomers which form supramolecular insulin assembly are swollen and have retained native like structure. Similar non-fibrillar structures are also observed by TEM studies. The biological effectiveness of insulin is generally assessed by its ability to regulate glycemic level in the blood. The resultant decrease in the blood glucose concentration represents the most noticeable and, therapeutically, the most important effect of insulin. The efficiency of glycemic control in STZ-induced diabetic rats treated with single dose of supramolecular insulin assembly and compared with single-daily insulin injections was assessed. Both supramolecular insulin assembly treatment and insulin injection reduced the severity of hyperglycemia. Compared to insulin treatment, single dose of supramolecular insulin assembly of the present invention maintains near-normoglycemic levels (120 mg/dL) in the diabetic animal for a period of about 150-180 days.

The present invention further assesses the effect of supramolecular insulin assembly II therapy in regulation of blood glucose level. The supramolecular insulin assembly treated diabetic animals were subjected to overnight fasting. These fasted animals were able to maintain their fasting blood glucose levels within the normal range (60-100 mg/dl) and no pre-prandial hypoglycemia was observed. Taken together, these data provided that higher oligomeric state of supramolecular insulin assembly II compared to conventional insulin therapy achieves a tightly regulated glycemic control without fasting hypoglycemia in diabetic animals.

The present invention further assesses the effect of supramolecular insulin assembly II treatment on body weight. Intraperitoneal glucose tolerance test conducted to determine the onset of the action of supramolecular insulin assembly in case of severe hyperglycemia. The IPGTT blood glucose profile showed that both insulin and supramolecular insulin assembly treatment showed their effect within 30 min, suggesting no lag phase in release of bioactive insulin monomers from supramolecular insulin assembly II depot.

The present invention provides in vivo release profile of insulin from supramolecular insulin assembly by bovine/human insulin quantification in the serum using ELISA. In contrast to sigmoid release kinetics observed in vitro, in vivo release of insulin monomers from supramolecular insulin assembly followed zero order kinetics as expected for a sustained release. A sustained release of basal and above basal level (0.5-1.2 ng/ml) of insulin for maintaining normoglycemia was seen, which correlated well with the duration of the treatment. To validate the above release kinetics, radiolabeling of insulin with 125I was done and 125I labeled supramolecular insulin assembly were injected either subcutaneously or intramuscularly to STZ treated animals. The amount of insulin release was measured by monitoring CPM/ml. CPM/ml/µg (49912) was used for the quantification of insulin released in the serum at a particular time point and this paralleled to the amount of bovine insulin quantified using ELISA. After measuring counts, serum samples were resolved on Tricine-SDS-PAGE. The phosphor images developed showed bands corresponding to insulin monomer. The insulin monomers released from the supramolecular insulin assembly depot triggered efficaciously the insulin signaling cascade in insulin responsive adipocytes. Insulin released from the supramolecular insulin assembly in vitro and in vivo (serum), when added to isolated adipocytes was able to activate the intracellular mediators (i.e. PI3K, Akt, ERK1/2 and GSK3β) of the signaling pathway. Therefore, the insulin monomers released from supramolecular insulin assembly depot are biologically active and follow the same mechanism as insulin to regulate the glucose homeostasis in the body. The histochemistry also provides that the supramolecular insulin assembly II injected in animals formed a depot from which there is a slow and sustained release of bioactive insulin. Furthermore, there is no inflammation observed as opposed to infiltration of leucocytes in response to subcutaneously or intramuscularly injected LPS.

The present invention provides that the supramolecular insulin assembly therapy confers profound physiological benefits in diabetic animals. This is partially reflected in the significantly improved glycemic control as well as markedly reduced urea and creatinine concentrations due to improved liver and kidney functions in diabetic rats as provided in Table 1.

The present invention provides details of anti-insulin antibodies and insulin degrading enzyme (IDE) in serum on administration of supramolecular insulin assembly. The absence of anti-insulin antibodies even by the end of the 12th week adds to the value of supramolecular insulin assembly as a treatment for diabetes mellitus. Its inability to elicit IDE in or around the site of injection is an important factor in prolonging the release of insulin from the supramolecular insulin assembly and the concomitant beneficial anti-diabetic affect.

The present invention provides that insulin monomer released from supramolecular insulin assembly II has equivalent biological function as soluble insulin. A significant difference lies in the duration of action, whereas it is only the 6-10 hrs for standard insulin injection, but surprisingly so, about 10 days to about 180 days or more depending on the dosage of the supramolecular insulin assembly II. This may be attributed to the remarkable stability of insulin in the supramolecular insulin assembly, which forms a depot at the site of injection for the supply of the most physiologically relevant form of insulin, viz. insulin monomers, for long periods of time.

Administration of supramolecular assembly II of human insulin led to an even better glycemic control, observed over a period of 135-180 days. Both subcutaneous and intramuscular injection of the insulin oligomer resulted in near normoglycemia as evident from the FIGS. 8*b* and 9*b*.

Released insulin in serum was quantified using ELISA and was observed to maintain an almost constant level, resulting from a slow and sustained release from the depot.

Male wistar rats rendered diabetic with alloxan and streptozotocin treated diabetic C57b1/6 mice (served as another model of diabetes), both showed near normoglycemic blood glucose level upon being treated with supramolecular insulin assembly II.

The western blot data obtained for human supramolecular assembly II insulin is essentially the same, showing the activation of the signaling pathway by the released insulin monomers.

The supramolecular insulin assembly I is characterized by swollen and more globular species with 18±2 nm height. The unfolding of the peptide structure during the process of amyloid formation results in globular monomeric species randomly distributed over the surface individually. Further onwards there is a linear association of these monomers at stage II of the human insulin supramolecular assembly II, albeit retaining their swollen morphology. The oligomers formed represent elongated clusters, same as bovine insulin with a height of 18±4 nm. In case of supramolecular insulin assembly III (closer to the fibril stage succeeding SIA II), an increase in density of higher oligomeric structures is seen. The structure is more compact with a height of 5±1 nm. The overall structural morphology resembles bovine SIA stages, with fully formed fibers seen further onwards.

The present invention provides the efficacy as well as the feasibility of supramolecular insulin assembly therapy for the significant improvement of blood glucose level without causing fasting hypoglycemia in STZ-induced diabetic animal model. Unlike intensive insulin therapy, by which blood glucose levels is controlled by an increased frequency of insulin injection with concomitant risk of hypoglycemia, the significantly improved glycemic control using supramolecular insulin assembly therapy, is accomplished without the need for multiple insulin injections and without excessive body weight gain.

A further value to this innovation is added by the extension of these studies to those ailments requiring a sustained and continuous infusion of insulin as a therapy, as in the case of Diabetes Mellitus type II (DM II). Both Exendin 4 and insulin, in combination is utilized as a potent therapy for DM II. Exendin 4 is known to lower blood glucose levels, through decrease in the absorption of food from the stomach. It also delays gastric emptying, lowers the levels of HbAc and prevents the large increase in weight observed due to insulin therapy. Exendin 4, aggregated into an oligomeric complex, from which the native monomers of Exendin 4 is released as is the case with insulin reported in the above section. Exendin 4 is used as an adjunct therapy along with SIA I and II for the treatment of DM II in animal subjects.

Example 24 describes monitoring of counter-regulatory hormones, wherein Hyperinsulinemic Euglycemic/Hypoglycemic Clamp studies were performed to monitor the levels of insulin counter-regulatory hormones, such as glucagon and epinephrine. A decrease of 40% was observed in the peak level of glucagon for SIA-II treated rats in comparison to normal control Wistar rats (FIG. 29). In contrast, daily insulin treated rats showed 80-90% reduction in glucagon response. Thus, basal insulin release from SIA-II mimics the physiology of the body and does not cause a significant alteration in the counter-regulatory mechanism of the body for maintaining glucose homeostasis, unlike the daily insulin treatment.

Recurrence of hypoglycemia during SIA-II treatment in diabetic rats was ruled out by monitoring the insulin counter-regulatory hormone response to induced hypoglycemia in various treated groups. Glycemic regulation through insulin counter-regulation was maintained in SIA-II treated rats.

Example 25 describes protease resistance study to evaluate the stability of the supramolecular insulin assembly I, II and II.

Resistance of SIA-II and SIA-III to cleavage by Trypsin and Proteinase K further demonstrate the difference in the structural organization of these oligomers. rH Insulin and SIA-I are more susceptible to cleavage by the proteases as compared to SIA-II and SIA-III (FIG. 30), which adopt an higher order oligomeric form resistant to protease action.

Thus the present invention not only encompasses metabolic disease such as Diabetes, both type I and II, but can be further extended to all those diseases such as chronic pain, sepsis, arthritis, osteoporosis, inflammation, etc, where a continuous infusion of the therapeutic drug is required, be it a peptide, protein or a small drug molecule. This invention also discusses the feasibility of using insulin oligomer (SIA I, SIA II and SIA III) for the treatment of DM I, DM II and borderline diabetic cases. This methodology of utilizing the oligomers of the drug as a depot for treatment can be extended to many more diseases, having a all round, broad spectrum applicability.

The following examples are given by the way of illustration of the invention contained in the present invention and therefore should not be construed to limit the scope of the present invention.

EXAMPLES

It should be understood that the following examples described herein are for illustrative purposes only and that various modifications or changes in light of the specification will be suggestive to person skilled in the art and are to be included within the spirit and purview of this application and the scope of the appended claims.

Example 1

Insulin Fibrilization

Bovine and rH insulin, 2 mg/ml, was dissolved in phosphate buffer saline (50 mM, pH 7.0) or pH 2.0 (Hydrochloric acid in water) and incubated at 37° C. for 72 hr-7 days with constant agitation at 180 rpm. The kinetics of fibril formation was monitored by monitoring the acquisition of fluorescence by Thioflavin T (Th-T).

Example 2

Thioflavin T Fluorescence

Th-T fluorescence was measured on a Jobin Yvon Fluoromax spectrofluorometer using slit widths of 3 nm and 5 nm for excitation and emission respectively. Samples incubated with 50 μM of Th-T for 15 minutes were excited at 450 nm and their emission was monitored in the range of 460-560 nm. The data was corrected for blank and inner filter effect using the following equation, $Fc = F \text{ antilog}[(A_{ex}+A_{em})/2]$ Where Fc is the corrected fluorescence and F is the measured one, $A_{ex}$ and $A_{em}$ are the absorbance of the reaction solution at the excitation and emission wavelengths respectively.

Kinetics of formation of fibrils by bovine and rH insulin at 37° C. is provided in FIG. 1. FIG. 1(a) demonstrates kinetics of fibril formation at pH 7.0 monitored with 50 μM Th-T fluorescence.

Example 3

In Vitro Monomer Release Kinetics of Intermediates and Fully Formed Fibrils Formed at pH 2.0 and 7.0

200 μl (equal to 400 μg of insulin) aliquots were withdrawn at different time point from the insulin fibrilization reaction at pH 2.0 and 7.0, 37° C. The supramolecular insulin assembly intermediate produced were isolated by centrifugation. The pellet obtained was washed with PBS and resuspended in 1 ml PBS in an eppendorf. The cap of the eppendorf containing the intermediates was removed and the eppendorf was sealed with 12 kDa cut off dialysis membrane. The eppendorf was then inserted through its membrane side into a 50 ml Falcon tube containing 20 ml PBS with 0.02% sodium azide and the kinetics of the release of insulin was monitored for 15 days under constant stirring. The kinetics of release was monitored spectrophotometrically at 280 nm and by its intrinsic (tyrosine) fluorescence. The amount of insulin released per hour was calculated. FIG. 2a provides in vitro release of insulin from Supramolecular insulin assembly II intermediate monitored by absorbance at 280 nm and intrinsic tyrosine fluorescence. The Th-T intensity of solution inside the dialysis membrane at 0 h and 15 days is also given.

To study release profile of different intermediates small aliquots of intermediates and fully formed amyloid fibrils at both pH 2.0 and 7.0, 37° C. were withdrawn from the fibrilizaton process at regular intervals and centrifuged at 10,000 rpm for 10 minutes. Supernatant was removed and after washing the pellet twice with PBS, resuspended in fresh PBS. The release of monomeric insulin was monitored spectrophotometrically at 280 nm, 37° C. Release kinetics was studied in two different conditions. In one, the pellet was suspended in PBS and dialyzed through a 12 kDa cut off membrane in 20 ml PBS with constant stirring (FIG. 2a-c). In second, the pellet obtained was suspended in 1 ml of PBS and the absorbance of the supernatant was read at 280 nm (FIG. 2d).

Example 4

Congo Red Binding

The amount of Congo red bound to the insulin oligomers/amyloid was estimated as reported earlier (Klunk, W. E., Jacob, R. F. & Mason, R. P. Quantifying amyloid by Congo red spectral shift assay. *Methods Enzymol* 309, 285-305 (1999)) using the equation, moles of Congo red bound/L of amyloid suspension= $A_{540}$ nm/25295– $A_{477}$ nm/46306.

FIG. 3 provides congo-Red binding studies with native insulin, supramolecular insulin assembly II, supramolecular insulin assembly III and amyloid insulin.

Example 5

Tyrosine Fluorescence

The dialysate of supramolecular insulin assembly withdrawn at different time intervals in a 0.2 ml quartz cuvette was excited at 270 nm and emission recorded between 320 to 370 nm. Slit width of 5 nm was used for both excitation and emission. FIG. 2(a) provides in vitro release of insulin from supramolecular insulin assembly II intermediate monitored by absorbance at 280 nm and intrinsic tyrosine fluorescence. The Th-T intensity of solution inside the dialysis membrane at 0 h and 15 days is also shown.

Example 6

Fourier Transform Infrared Spectroscopy (FTIR)

IR spectra were recorded with a Bruker Tensor 27 bench top FTIR spectrometer, equipped with a liquid $N_2$-cooled mercury cadmium telluride detector. Insulin samples were analysed on Bio-ATR and 256 interferograms were recorded at room temperature with a resolution of 2 $cm^{-1}$. For each spectrum, water vapor was subtracted and baseline corrected.

SIA I, II and III were also characterized using ATR-FTIR. Distinct spectra corresponding to each stage was observed (FIG. 4).

Supramolecular insulin assembly I, II and III of bovine and rH insulin were also characterized using ATR-FTIR. Distinct spectra corresponding to each stage was observed (FIG. 4). A shift of the IR band towards lower frequencies is observed during fibrillization. Supramolecular insulin assembly II (SIA-II) has a sharp peak at 1647 $cm^{-1}$ and 1645 $cm^{-1}$ for bovine and rH insulin respectively, while the fully formed amyloid peaks at 1630 $cm^{-1}$ and 1628 $cm^{-1}$ for the same. The FTIR spectra is in good agreement with the CR binding data showing that the conformation of SIA-II is still largely helical, albeit with an increase in the content of random coil structure.

Example 7

Atomic Force Microscopy (AFM)

Pico plus atomic force microscope (Agilent Technologies) was used in magnetic acoustic MAC (contact) mode for imaging. Images were recorded in air with either a bare mica surface or mica with sample using MAC cantilever Type II (spring constant of cantilever: 2.8 N/m, Frequency: 59.722 kHz). Samples were withdrawn from the fibrilization reaction mixture at various time points, diluted 20 fold with water and immobilized on freshly cleaved mica for 2 minutes. The samples were washed with nanopure water, dried under $N_2$ and subjected to AFM analysis.

FIG. 5 provides morphologies of supramolecular insulin assembly intermediates and insulin fibrils studied by Atomic Force Microscopy. FIG. 5(a) insulin monomer (b) Supramolecular insulin assembly-I intermediate, pH 7.0, (c) Supramolecular insulin assembly II, pH 7.0, (d) Supramolecular insulin assembly intermediate III, pH 7.0, (e) human SIA I, (f) human SIA II, (g) human SIA III, and (h) Fully formed fibrils at pH 7.0., (i) provide supramolecular insulin assembly intermediate formed at 6 hrs, pH 2.0 at 37° C., (j) provides fully formed amyloid fibril formed at pH 2.0.

Example 8

Transmission Electron Microscopy (TEM)

For TEM studies, samples were vortexed and immediately absorbed to fomber-coated 300 mesh copper grids as such or diluted to 1:2-20 fold with mili-Q water and washed with deionized water. Grids were incubated in 3% Uranyl Acetate for 2-5 min and dried under infra red light for examining the samples by negative stain. The grids were visualized with a Phillips CM-10 at 80 kV. The pictures were captured using MegaView III camera and analyzed using the Imaging Software from Imaging System Phillips. FIG. 6 provides negative staining TEM micrographs of insulin fibrils and supramolecular insulin assembly intermediates, wherein FIG. 6(a) provides supramolecular insulin assembly I intermediate, pH 7.0, FIG. 6(b) provides supramolecular insulin assembly II, pH 7.0, FIG. 6(c) provides supramolecular insulin assembly intermediate III, pH 7.0, FIG. 6(d) provides mature fibers at pH 7.0, FIG. 6(e) provides fiber formed at pH 2.0, 37° C.

Example 9

Rat Model of Diabetes

Nine weeks old Male Wistar rats (*Rattus norvegicus albinus, Rodentia mammalia*) weighing 210±10 g were used. Rats were housed in commercially available polypropylene cages and maintained under controlled temperature conditions on a 12 h light-dark cycle and allowed to access food and water ad libitum.

Streptozotocin Model for Induction of Diabetes in Rats

Male Wistar Rats weighing 250-300 g were divided into four groups and blood glucose estimation was done using Roche Accu Check glucose strips. Rats were kept on fasting for 48 hours. 50 mg/kg b·wt of Streptozotocin prepared freshly in citrate buffer (pH 4.5) was administered intraperitoneally to 10-20 rats. Food was provided immediately and blood glucose levels were checked after three days. The animals were grouped according to their blood glucose level (group I: 250-350 mg/dl, group II: 350-450 mg/dl and group III: >450 mg/dL). High blood glucose levels were maintained for a week with 2-6 U/kg body weight (b·wt) of bovine insulin. All STZ-treated rats developed hyperglycemia (blood glucose levels >250 mg/dl), 5 days after STZ injection, and their serum insulin levels were quantified using rat insulin solid enzyme-linked immunosorbent assay (ELISA) (Mercodia). Rats with >250 mg/dL of glucose and negligible (~0.08 ng/ml) serum insulin levels were considered diabetic and used for the experiment.

Example 10

Supramolecular Insulin Assembly Treatment

Figure 7B:
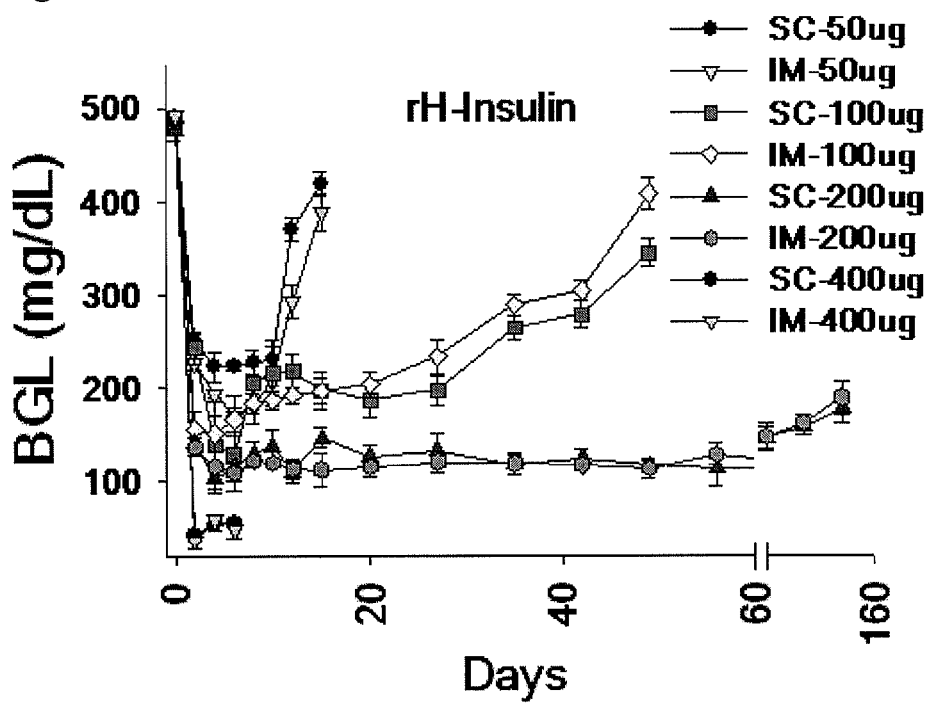

After one week of maintaining high blood glucose levels with insulin, the rats were divided into three groups, each containing 5 rats. Group I rats were administered single dose of 4 U/kg b·wt of bovine insulin intraperitoneally per day. Group II rats were injected 4 U/kg b·wt of insulin twice daily. Group III treated with 200 µg of supramolecular insulin assembly II (subcutaneously as well as intramuscularly) in 100 µl of PBS and group IV rats were administered 100 µl of PBS, constituting the diabetic control. A group of 5 normal rats injected 100 µl of PBS, served as the non-diabetic control. Body weight and blood glucose levels, both pre-prandial after 8-10 hr fasting and post-prandial were checked initially daily and then with decreasing frequency. FIG. 7 shows in vivo efficacy of supramolecular insulin assembly (alternatively pre-amyloid insulin) in glucose homeostasis. (a) Blood glucose level in response to various dosages of supramolecular insulin assembly-II (bovine) administered both subcutaneously and intramuscularly. (b) Blood glucose level in response to various dosages of supramolecular insulin assembly-II (r-human) administered both subcutaneously and intramuscularly.

FIG. 8 shows Post-prandial blood glucose levels monitored over a period of 135 days after administration of bovine SIA-II (a) Bovine insulin, (b) rH insulin. FIG. 9 shows Pre-prandial blood glucose levels monitored over a period of 160 days after administration of human SIA-II (a) Bovine insulin, (b) rH insulin. FIG. 10 shows blood glucose level monitored after administration of insulin amyloid formed at pH 2.0 and 7.0. FIG. 11 shows body weight profile of SIA-II treated diabetic rats, diabetic control and non-diabetic control rats.

Example 11

Intraperitoneal Glucose Tolerance Test (IPGTT)

The STZ treated (n=12) and normal rats (n=4) were kept on fasting for 12 hrs. Blood glucose levels were monitored as described above. For glucose tolerance test was done. Briefly, animals were infused with 3 g/kg body weight of glucose, intraperitonealy, followed by injection of 4 U/kg b·wt of Bovine insulin to group I, 100 µl of amyloid insulin to group II and 100 µl of PBS (vehicle) to group III rats. Blood glucose levels were monitored at 0, 30, 90, 150, 270 and 330 min after treatment. Serum was isolated for various time points and a graph was plotted between blood glucose level and time. FIG. 12 provides blood glucose profile of Intraperitoneal Glucose Tolerance Test (IPGTT).

Example 12

Serum Insulin Quantification

Serum was isolated from the blood samples collected and stored at −20° C. till further analysis. Bovine and rat insulin levels were quantified using solid phase two site enzyme immunoassay (ELISA) from Mercodia (Sweden), by following the manufacturer's protocol. FIG. 13a provides quantification of serum human and bovine insulin using ELISA in STZ treated rats in response to supramolecular insulin assembly injected SC or IM, FIG. 13(b) provides quantification of serum bovine insulin of IPGTT, FIG. 13(c) provides serum rat insulin ELISA performed for IPGTT.

Example 13

$I^{125}$ Labelling of Insulin

To further validate and quantitate the in vitro release from the termini of insulin SIA II, labeling of insulin with $^{125}I$ was done (Pause, E., Bormer, O. & Nustad, K. Radioiodination of proteins with the iodogen method, in RIA and related procedures in medicine, international atomic agency, Vienna, 161-171 (1982)). Supramolecular insulin assembly formed from labeled insulin had a specific activity of 49912 CPM/ml/µg. 50 µl of supramolecular insulin assembly (4991200 CPM) was injected either subcutaneously or intramuscularly and blood glucose levels were monitored and serum samples were collected at 0, 30 min, 1 h, 4 h, 10 h, 24 hrs, thereafter once a day, and then on alternate days or once in a week. Counts in per ml of serum were measured (FIG. 14a). As shown in FIG. 14b, blood glucose profile was same as observed with the unlabeled SIA II. The CPM/ml calculated remained almost constant (FIG. 14a) when plotted against the number of days of treatment. However, there was an initial high count at 30 min-4 hrs, which then gradually decreased to a constant level of 2000-3000 in 10 hrs. The amount of insulin released in blood was calculated and was in the range of 0.5-1.2 ng/ml which corresponded to the basal or slightly above basal level of insulin in the serum as observed with ELISA (FIG. 14b). To further prove that the released insulin from supramolecular insulin assembly is monomeric, serum of different time points were resolved on tricine-SDS-PAGE (Schaögger, H. & Von Jagow, G. Tricine-sodium dodecyl sulfate-polyacrylamide gel electrophoresis for the separation of proteins in the range from 1 to 100 kDa. Anal Biochem 166, 368-379 (1987)) and radiogram was developed using the phosphor imager. As shown in FIG. 15, the band in serum corresponds to free insulin monomer and its intensity remained constant for a long period when equal amount of serum was loaded. A decrease in intensity was observed after 20 days showing usage and depletion of the supramolecular insulin assembly depot over a period of time together with some effect of the decay of the radio-label itself.

Example 14

Hyperglycemic Clamp after Treatment with Supramolecular Insulin Assembly II

Male wistar rats were anesthetized (Isoflurane 2%) and a carotid and jugular catheter installed to allow blood withdrawal and glucose injections (20% glucose solution) to clamp blood glucose level at 600 mg/dL. Following a 12 hours fasting period, glucose was infused in all groups to make them hyperglycemic. This was followed by blood withdrawal at indicated time intervals, for blood glucose measurements and the rate of glucose infusion to retain them hyperglycemic were calculated. This procedure was repeated after one and three months of SIA II administration (FIG. 16 a-c).

Example 15

Isolation and Primary Culture of Rat Adipocytes

Rat adipocytes were isolated and cultured according to the method described by Bjorntorp et al. (Björntorp, P., Karlsson, M., Pettersson, P. & Sypniewska, G. Differentiation and function of rat adipocyte precursor cells in primary culture. *J. Lipid Res.* 21, 714-723 (1987)). Male Wistar rats fed freely were sacrificed and epididymal fat tissue was dissected and collected in reagent A (HBSS, 100 U/ml penicillin, 100 µg/ml streptomycin and 50 µg/L gentamycin). The tissue was washed properly in HBSS. Following this the tissue was cut and minced finely and transferred to a falcon, centrifuged at 200 g for 2 min. The layer of transparent oil was removed and the adipocyte cell layer (thick and dense) was added to three times the volume of reagent B (reagent A containing 0.1% BSA and 1 mg/ml Collagenase) in a flask. The flask was incubated at 37° C. for 60 min with continuous slow shaking. The reaction was stopped by addition of DMEM complete media (with HEPES 15 mM, glc, 0.1% BSA, 50 nM adenosine and 1% fetal bovine serum) three times the volume and incubated at room temperature for 5 min. The reaction was transferred to a falcon and centrifuged at 200 g for 10 min. Adipocytes were collected after discarding the top layer of oil and washed twice with reagent A by centrifuging at 200 g for 10 min. Cells were dispensed into a flask with appropriate volume of DMEM complete media and incubated for 24 hrs at 37° C. For insulin signaling, adipocytes were centrifuged and maintained in serum free medium for 12 hrs before plating approximately 2 ml into 6 well culture plates, and incubated further for 2 hrs.

Example 16

Western Blot Analysis of Total Cellular Lysates

Plated cell were incubated with either 20 nM insulin, 50 µl of supramolecular insulin assembly and in vitro released insulin (monomers) or 50 µl of serum from rats treated with insulin, supramolecular insulin assembly and PBS for 10 min. After incubation, the cells were collected in a falcon tube and centrifuged at 200 g for 10 min. The top layer of adipocytes were collected in an eppendorf and kept in ice. 500 µl of lysis buffer (20 mM Tris pH 8.0, 1% NP 40, 137 mM NaCl, 1 mM $MgCl_2$, 1 mM CaCl2, 1 mM DTT, 10% glycerol, 1 mM PMSF, 0.4 mM sodium orthovanadate and protease inhibitor cocktail) was added and the samples were frozen at −80° C., for 2 hrs. This was followed by thawing and incubating at 4° C. for 4 hrs with constant rotation. The supernatant was collected after centrifugation at 13000 rpm for 30 min and protein concentration in cell lysate was estimated using Bradford reagent. Fifty micrograms of total cellular protein were applied to each lane and were separated on 10% SDS-PAGE and transferred to nitrocellulose membrane using Bio-rad wet transfer apparatus at 4° C. overnight. After transfer, the blot was removed and stained with Ponceau-S for the visualization of transferred bands, and destained further with water. The membrane was blocked for 1 hr at 37° C. with 5% skimmed milk in PBS, pH 7.4, washed and then incubated overnight in primary antibody (1:1000 dilution using 1% skimmed milk in PBS) of PI3K, p-Akt, total Akt, p-Gsk3β, Gsk3β, ERK1/2, GAPDH and β actin (antibodies from cell signaling) at 4° C. After washing with PBST, the blot was incubated for 1 hr in respective secondary antibody (HRP-conjugated), and immunoreactive bands were visualized using the ECL western blotting protocol (Amersham). FIG. 17 provides western blot (WB) analysis of cultured adipocytes for insulin signaling cascade. Adipocytes treated with (a) PBS, insulin, SIA-II, insulin released from SIA-II, (b) serum as indicated, and analysed for insulin signaling.

Example 17

Histology and Immunohistochemistry

Rats were injected 200 µg of insulin SIA-II or 150 µg of Lipopolysaccharides (LPS) from *Escherichia coli* (Sigma-Aldrich, Mo., USA) either through intramuscular or subcutaneous injections into thigh muscle and dorsal skin respectively. LPS injected rats were sacrificed after 48 h of injection whereas rats injected insulin SIA-II were monitored from 1 to 12 week and tissue sections were excised at an interval of every 7 days. Rats were anesthetized by ketamine and perfused with 4% paraformaldehyde. Skin and thigh muscles were removed and the injection site was excised out. Tissues were then processed for paraffin embedding and were sagitally sectioned at a thickness of 10 µm and further processed for routine hematoxylin-eosin (H & E) staining to see histology and the infiltration of inflammatory cells, Congo red staining (Lee, G. & Luna, H. T. Manual of Histologic staining methods of armed forces institute of pathology. 3rd Ed. McRaw-Hill book company (1960)) for the presence of residual SIA-II and Immunohistochemistry (Sanz M J, Marinova-Mutafchiev L, Green P, Lobb R R, & Feldmann M, Nourshargh S. IL-4-induced eosinophil accumulation in rat skin is dependent on endogenous TNF-alpha and alpha 4 integrinNCAM-1 adhesion pathways. J Immunol. 160, 5637-5645 (1998)) with antibodies against CD11b, RT-1A, and CD6 (BD Pharmigen, CA, USA). All immunoflorescent slides were mounted permanently with antifade reagent+ mounting medium (Molecular probes, Eugene, Oreg., USA) and observed under florescent light for FITC conjugated antibodies. CR and H&E stained slides were mounted with citramount medium (Polysciences, PA, USA). H&E sections were observed under bright light whereas, CR stained slides under bright and polarized lights (Nikon Eclipse 80i, Nikon, Japan). Images were captured using DS SMc CCD camera (Nikon, Japan) and were analyzed by NIS-Element software (Nikon, Japan).

Example 18

Alloxan Model for Induction of Diabetes in Rats

Male Wistar Rats weighing 250-300 g were divided into four groups and blood glucose estimation was done using Roche Accu Check glucose strips. Rats were kept on fasting for 24 hours. 150 mg/kg b·wt of Alloxan prepared freshly in citrate buffer (pH 4.5) was administered intraperitoneally to 10-20 rats. Food was provided immediately and blood glucose levels were checked after three days. The animals were grouped according to their blood glucose level (group I: 250-350 mg/dl, group II: 350-450 mg/dl and group III: >450 mg/dL). High blood glucose levels were maintained for a week with 2-6 U/kg body weight (b·wt) of bovine insulin. 60% of Alloxan-treated rats developed hyperglycemia (blood glucose levels >250 mg/dl), 5 days after injection, and their serum insulin levels were quantified using rat insulin solid enzyme-linked immunosorbent assay (ELISA) (Mercodia). Rats with >250 mg/dL of glucose and negligible (~0.18 ng/ml) serum insulin levels were considered diabetic and used for the experiment.

Example 19

Examples of Clinical Parameters Examined

Biochemical assays were performed for the evaluation of toxicity of supramolecular insulin assembly treatment. Serum glutamate oxalo-acetate transaminase (SGOT), serum glutamate pyruvate transaminase (SGPT), total Bilirubin, Bilirubin, Alkaline Phosphatase, Serum total proteins, Serum Albumin, Serum Globulin, Serum A/G ratio, Kidney function test (KFT), Cataract Formation, Adipose Tissue weight, Body Weight and Appearance were estimated using assay kits available from Merck India Ltd. Table 1 provides the analysis of clinical parameters for the evaluation of toxicity of Insulin SIA II. Serum isolated from blood samples collected at the end of the three month study and subjected to various tests indicated in the Table. Results are mean±s.d. of three different experiments having n=4 animals in each group.

Example 20

Detection of Anti-Insulin Antibodies and Insulin Degrading Enzyme (IDE) in Serum Indirect ELISA was performed for the detection of anti-insulin antibodies in the rat serum by following the standard ELISA protocol. Indirect ELISA was performed for the detection of anti-insulin antibodies in the rat serum by following the standard ELISA protocol. Briefly, 200 µl of 2 mg/ml of bovine insulin in 50 mM carbonate buffer, pH 9.6, was coated onto a 96 well ELISA plate and kept overnight at 4° C. 5% BSA in PBS was used for blocking at 37° C. for 1 hr. The plate was then washed with PBST (0.02% Tween 20) and 20031 of 1:100 diluted serum was added and kept at 37° C. for 1 hr. Further rounds of washing with PBST was followed by the addition of 1:10000 diluted anti-rat IgG-HRP conjugated 2° antibody and incubated for 2 hrs, 37° C. Color was developed using TMB as a substrate and reaction stopped by the addition of conc $H_2SO_4$. The plate was read at 450 nm spectrophotometrically. Anti-insulin antibody was used as a positive control for the reaction. IDE was quantified from the serum using Insulysin/IDE InnoZyme™ Immunocapture Activity Assay Kit (Calbiochem) following the manufacturer's protocol. Rat IDE provided in the kit served as the positive control.

Cell Proliferation Assays

Cells were plated in 24-well plates with 10,000 cells/well in regular DMEM media containing 10% FBS. Cells were switched to Serum Free Media for 12 h and then treated as indicated in the figure legends of FIG. 25. All treatments were done in triplicates. Growth was measured 3 days after treatment. Growth was assayed by the MTT assay. A total of 50 μl of 5 mg/ml MTT solution in PBS was added to each well. After incubation for 4 h at 37° C., formazan crystals were lysed with 500 μl of solubilization solution (20% SDS, 50% DMSO). Absorbance was measured with a plate reader at 570 nm using a 670-nm differential filter.

Example 21

Streptozotocin Model for Induction of Diabetes in Mice

Inbred 12-16-week-old C57BL/6 male mice were used. Mice were injected intraperitoneally with 50 mg/kg b·wt of streptozotocin daily for 5 days. Blood glucose levels were estimated after two weeks. Mice with >300 mg/dl of blood glucose were considered diabetic and selected for further experiments. A total of six groups were made, with each group consisting of six mice each. Various dosages, such as 10 μl, 25 μl, 50 μl and 100 μl of bovine/human insulin SIA-II was administered either subcutaneously or intramuscularly to mice rendered diabetic using Streptozotocin, with the two other groups serving as the diabetic and the non-diabetic group. Both fasting and fed blood glucose levels were monitore using the Roche Accu Check glucose strips.

Example 22

Streptozotocin Model for Induction of Diabetes in Rabbit

Male New Zealand rabbits, weighing between 100 μl and 1200 g were used. Animals were maintained under controlled conditions of humidity, temperature (22±2° C.) and 12 h light and dark cycle. The experimental protocol and animal handling was in accordance with the Institutional animal ethics committee of the National Institute of Immunology, New Delhi, India. For induction of experimental diabetes, rabbits used were fasted for 12 h, followed by administration of 80 mg/kg b·wt of Streptozotocin, prepared in citrate buffer, pH 4.5. Blood glucose levels were checked after three days. Rabbits showing BGL >450 mg/dL were termed diabetic and further divided three groups of three rabbits each. Group I—normal healthy rabbits, group II—diabetic treated with insulin, group III—diabetic treated with SIA-II (SC) and group IV—diabetic treated with PBS.

Example 23

Model for Induction of Diabetes Type II in Wistar Rats and its Treatment Using SIA Male Wistar rats, 7 weeks of age, and weighing approximately 200 g, were used for all studies. Animals were fed either a normal chow diet consisting (as a percentage of total kcal) of 12% fat, 60% carbohydrate, and 28% protein or a high-fat diet consisting of 40% fat, 41% carbohydrate, and 18% protein. After 2 weeks on either diet, animals (with the exception of non-injected controls) after an overnight fast were injected with STZ (50 mg/kg) into the tail vein via a temporary indwelling 24-gauge catheter. Animals had free access to food and water after the STZ injection, and both STZ-injected and non-injected animals were continued on their original diets (chow or fat) for the duration of the study. Animals with high blood glucose levels were administered either PBS as vehicle, insulin SIA, or insulin SIA with Exendin 4a subcutaneously. Blood was collected and serum was separated by centrifugation and analyzed for concentrations of glucose (glucose strips, Accucheck, Roche), insulin (Insulin Elisa Kit, Mercodia), triglyceride (TG) (glycerol phosphate oxidase [GPO]-Trinder method, Sigma) and free fatty acid (acyl coenzyme A synthetase [ACS-ACOD] method, Wako Diagnostics, Richmond, Va.).

Diabetes Type II: Db/db Model

Db/db mice on a C57BL/6 background were fed ad libitum with a standard diet and kept under a 12-h light/dark cycle. Blood samples were collected via mouse tail bleeds, and circulating glucose levels were determined using a glucometer (Roche Accu Check glucose strips). Serum insulin levels were determined from serum samples using an insulin enzyme linked immunosorbent assay kit (Mercodia). Fasting blood glucose and random-fed glucose were performed in the morning on alternate days.

Example 24

Insulin Counter-Regulatory Hormone Monitoring

The hyperinsulinemic glucose-clamp procedure was followed to provide a fixed hypoglycemic stimulus to rats. Animals were catheterized as described above. Conscious and unstressed rats were fasted for 12-14 hours before the start of the experiment. Constant insulin infusion of 30 mU/kg·min was begun along with a variable infusion of exogenous glucose, which was adjusted based on the blood glucose measurement obtained at 10 min intervals to achieve the desired glucose level. During the first 90 min of the experiment, the rats were brought to euglycemia, ~110 mg/dL. Thereafter, blood glucose level was decreased to ~50 mg/dL (induced hypoglycemia by infusion of insulin), and was maintained for the next 90 min. Experiments were terminated if the glucose levels fell below 80 mg/dL and 40 mg/dL during the euglycemic and the hypoglycemic phase, respectively. Blood samples for measurement of glucagon and epinephrine were withdrawn at various time intervals, as indicated in the FIG. 29.

Example 25

Protease Resistance

To 20 μl of 2 mg/ml rH Insulin, SIA-I, SIA-II and SIA-III, 1:5, 1:10 and 1:50 dilution of 2 mg/ml trypsin and 1:1000, 1:2000 and 1:5000 dilution of 2 mg/ml Proteinase K was added. The reaction mixture was incubated for 12 hrs at 37° C. in an incubator. The samples were loaded onto 20% SDS-PAGE and analyzed using Coomassie stain.

TABLE 1

Analysis of clinical parameters for the evaluation of toxicity of Supramolecular Insulin Assembly II (SIA II)

| Parameters estimated | Normal rats | SIA II treated | Single daily Insulin Injection | Twice daily Insulin Injection |
|---|---|---|---|---|
| LFT | | | | |
| Bilirubin (Total) (mg/dL) | 0.35 ± 0.03 | 0.35 ± 0.06 | 0.40 ± 0.08* | 0.35 ± 0.1 |
| Bilirubin (Direct) (mg/dL) | 0.108 ± 0.02 | 0.1 ± 0.03 | 0.36 ± 0.08* | 0.25 ± 0.06* |
| SGOT (U/L) | 222.8 ± 79 | 219.8 ± 61 | 355 ± 83* | 300 ± 56* |
| SGPT (U/L) | 74.8 ± 17 | 77 ± 21 | 86 ± 36 | 85 ± 15 |
| Alkaline Phosphatase (U/L) | 343.2 ± 76.8 | 431 ± 70.3 | 777.8 ± 89.4* | 489 ± 65 |
| Serum total proteins (g/dL) | 3.92 ± 0.095 | 6.14 ± 0.3 | 6.70 ± 0.21* | 5.55 ± 0.25* |
| Serum Albumin (g/dL) | 1.77 ± 0.11 | 1.85 ± 0.13 | 2.5 ± 0.21 | 3.2 ± 0.19 |
| Serum Globulin (g/dL) | 2.15 ± 0.08 | 2.64 ± 0.12 | 4.2 ± 0.18 | 3.35 ± 0.15 |
| Serum A/G ratio | 0.823 | 1.3 | 0.595 | 0.955 |
| KFT | | | | |
| Urea (mg/dL) | 47.68 ± 10.8 | 50.9 ± 7.6 | 58.3 ± 9.2 | 60.1 ± 12.36 |
| Serum Creatinine (mg/dL) | 0.80 ± 0.06 | 0.83 ± 0.02 | 1.01 ± 0.30 | 0.88 ± 0.21 |
| Uric Acid | 2.39 ± 0.12 | 2.26 ± 0.08 | 3.0 ± 0.81 | 3.1 ± 0.56 |
| Electrolytes | | | | |
| Sodium (mEq/L) | 140.6 ± 11 | 144 ± 10 | 200 ± 26 | 198 ± 45.5 |
| Phosphorous (mEq/L) | 4.5 ± 1.01 | 4.4 ± 1.1 | 6.5 ± 1.3 | 6.2 ± 0.95 |
| Chloride (mEq/L) | 102.8 ± 12 | 101 ± 17 | 165 ± 23 | 119 ± 26 |
| Cataract Formation | (−) | (−) | (+) | (+) |
| Adipose Tissue | Normal | Normal | Decreased | Decreased |
| Body Weight and Appearance | (+++) | (+++) | (+) | (++) |

TABLE 2

Effects of Treatments on the metabolic parameters of blood in fat-fed/streptozotocin-diabetic rats

| | 1 week | | | | | 2 week | | | | |
|---|---|---|---|---|---|---|---|---|---|---|
| Group | BGL (mg/dL) | Rat Insulin (μU/ml) | FFA (mmol/L) | TG (mmol/L) | B W | BGL (mg/dL) | Rat Insulin (μU/ml) | FFA (mmol/L) | TG (mmol/L) | B W |
| Control | 107 | 20.5 ± 1.95 | 0.87 ± 0.10 | 0.48 ± 0.17 | 253 | 98 | 19.5 ± 1.5 | 0.89 ± 0.10 | 0.49 ± 0.17 | 260 |
| Fat fed/STZ Control | 477 | 39.48 ± 6.72 | 2.45 ± 0.07 | 0.86 ± 0.04 | 265 | 480 | 35.38 ± 10.18 | 2.55 ± 0.07 | 0.89 ± 0.04 | 271 |
| Fat fed/STZ + Insulin | 420 | 37.09 ± 4.7 | 1.9 ± 0.08 | 0.77 ± 0.05 | 261 | 401 | 37.09 ± 4.7 | 2.1 ± 0.08 | 0.75 ± 0.05 | 263 |
| Fat fed/STZ + Insulin SIA | 180 | 34.83 ± 5.96 | 1.1 ± 0.06 | 0.68 ± 0.12 | 264 | 158 | 36.96 ± 5.04 | 1.0 ± 0.06 | 0.68 ± 0.12 | 268 |
| Fat Fed/STZ + Exendin-4 SA | 157 | 31.58 ± 6.75 | 0.91 ± 0.11 | 0.51 ± 0.13 | 252 | 121 | 21.58 ± 6.75 | 0.88 ± 0.11 | 0.50 ± 0.13 | 259 |

| | 3 week | | | | | 4 week | | | | |
|---|---|---|---|---|---|---|---|---|---|---|
| Group | BGL (mg/dL) | Rat Insulin (μU/ml) | FFA (mmol/L) | TG (mmol/L) | B W | BGL (mg/dL) | Rat Insulin (μU/ml) | FFA (mmol/L) | TG (mmol/L) | B W |
| Control | 100 | 20.1 ± 0.95 | 0.86 ± 0.10 | 0.51 ± 0.17 | 265 | 98 | 20.5 ± 1.95 | 0.9 ± 0.10 | 0.47 ± 0.17 | 276 |
| Fat fed/STZ Control | 506 | 39.55 ± 6.3 | 2.56 ± 0.07 | 0.91 ± 0.04 | 256 | 511 | 40.15 ± 1.35 | 2.59 ± 0.07 | 0.94 ± 0.04 | 250 |
| Fat fed/STZ + Insulin | 390 | 37.09 ± 4.7 | 1.8 ± 0.08 | 0.73 ± 0.05 | 269 | 396 | 37.09 ± 4.7 | 2.1 ± 0.08 | 0.76 ± 0.05 | 272 |
| Fat fed/STZ + Insulin SIA | 149 | 36.96 ± 5.04 | 0.9 ± 0.06 | 0.68 ± 0.12 | 272 | 163 | 22.42 ± 8.70 | 1.1 ± 0.06 | 0.68 ± 0.12 | 276 |
| Fat fed/STZ + Exendin-4 SA | 119 | 19.40 ± 4.86 | 0.87 ± 0.11 | 0.48 ± 0.13 | 265 | 158 | 23.40 ± 4.86 | 0.98 ± 0.11 | 0.65 ± 0.13 | 272 |

What is claimed is:

1. A method for treating metabolic disorders selected from the group consisting of type 1 diabetes mellitus, type 2 diabetes mellitus and complications thereof, wherein said method comprising administering to a subject in need thereof a therapeutically effective amount of the pharmaceutical composition comprising an isolated and stable supramolecular insulin assembly (SIA), wherein said assembly comprises insoluble and aggregated oligomeric form of insulin and wherein said assembly is protease resistant, exhibits no binding to Congo Red, has both α-helical and β-sheet components, and releases biologically active insulin monomers in vitro or in vivo, which is effective for the alleviation of said disorder.

2. The method of claim 1, wherein said assembly shows a sharp peak at 1647-1645 cm$^{-1}$ in Fourier Transform infrared spectroscopy (FTIR).

3. The method of claim 1, wherein said insulin is recombinant human insulin, bovine insulin, pig insulin, or a therapeutically-active mutant or analog of insulin.

4. The method of claim 1, wherein said assembly releases insulin at a rate ranging from 0.1 to 5.4 ng/ml for about 7 to 180 days, in vivo.

5. The method of claim 1, wherein said assembly releases insulin at a rate ranging from 4-5.4 ng/ml for at least 7-10 days.

6. The method of claim 1, wherein said assembly releases insulin at a rate ranging from 0.5-1.8 ng/ml for at least 160 days.

7. The method of claim 1, wherein said assembly upon administration to a diabetic subject maintains near-normoglycemic level (120±30 mg/dl) for at least 160 days in said subject.

8. The method of claim 1, wherein a single dose of said assembly in the range of 0.125 to 3.75 mg/kg body weight to a diabetic subject maintains near-normoglycemic level (120±30 mg/dl) for at least 7 to 180 days in said subject.

9. The method of claim 1, wherein a single dose of said assembly in the range of 0.75 to 1.25 mg/kg body weight to a diabetic subject maintains near-normoglycemic level (120±30 mg/dl) for at least 160 days in said subject.

10. The method of claim 1, wherein a single dose of said assembly to a diabetic subject maintains near-normoglycemic level (120±30 mg/dl) for at least 7 to 180 days in said subject, wherein concentration of the assembly in the dose is in the range of 25 to 750 μg.

11. The method of claim 1, wherein a single dose of said assembly to a diabetic subject maintains near-normoglycemic level (120±30 mg/dl) for at least 160 days in said subject, wherein concentration of the assembly in the dose is in the range of 150 to 250 μg.

12. The method of claim 1, wherein the pharmaceutical composition further comprises pharmaceutically acceptable carriers, additives or diluents.

* * * * *